(12) United States Patent
Schwendeman et al.

(10) Patent No.: US 11,642,419 B2
(45) Date of Patent: *May 9, 2023

(54) COMPOSITIONS AND METHODS FOR TREATING CARDIOVASCULAR RELATED DISORDERS

(71) Applicant: The Regents of the University of Michigan, Ann Arbor, MI (US)

(72) Inventors: Anna A. Schwendeman, Ann Arbor, MI (US); Yuqing Eugene Chen, Superior Township, MI (US); Yanhong Guo, Ann Arbor, MI (US); Jifeng Zhang, Ann Arbor, MI (US); Wenmin Yuan, Ann Arbor, MI (US); Emily Morin, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 629 days.

This patent is subject to a terminal disclaimer.

(21) Appl. No.: 15/561,372

(22) PCT Filed: Mar. 25, 2016

(86) PCT No.: PCT/US2016/024230
§ 371 (c)(1),
(2) Date: Sep. 25, 2017

(87) PCT Pub. No.: WO2016/154542
PCT Pub. Date: Sep. 29, 2016

(65) Prior Publication Data
US 2018/0250419 A1 Sep. 6, 2018

Related U.S. Application Data
(60) Provisional application No. 62/138,193, filed on Mar. 25, 2015.

(51) Int. Cl.
| | | |
|---|---|---|
| *A61K 47/69* | (2017.01) |
| *A61K 49/00* | (2006.01) |
| *A61K 9/51* | (2006.01) |
| *A61P 9/00* | (2006.01) |
| *A61K 45/06* | (2006.01) |
| *A61K 47/02* | (2006.01) |
| *A61K 9/00* | (2006.01) |
| *A61K 38/49* | (2006.01) |
| *A61K 31/145* | (2006.01) |
| *A61K 31/192* | (2006.01) |
| *A61K 31/4439* | (2006.01) |

(52) U.S. Cl.
CPC ........ *A61K 47/6917* (2017.08); *A61K 9/5169* (2013.01); *A61K 45/06* (2013.01); *A61K 49/008* (2013.01); *A61K 49/0032* (2013.01); *A61P 9/00* (2018.01); *A61K 9/0019* (2013.01); *A61K 31/145* (2013.01); *A61K 31/192* (2013.01); *A61K 31/4439* (2013.01); *A61K 38/49* (2013.01); *A61K 47/02* (2013.01); *A61K 2300/00* (2013.01)

(58) Field of Classification Search
CPC .............. A61K 2300/00; A61K 31/145; A61K 31/192; A61K 31/4439; A61K 38/49; A61K 45/06; A61K 47/02; A61K 47/6917; A61K 49/0032; A61K 49/008; A61K 9/0019; A61K 9/5169; A61P 9/00
See application file for complete search history.

(56) References Cited

U.S. PATENT DOCUMENTS

| | | | |
|---|---|---|---|
| 6,004,925 A * | 12/1999 | Dasseux | A61P 3/06 514/21.3 |
| 6,287,590 B1 | 9/2001 | Dasseux | |
| 6,514,523 B1 * | 2/2003 | Sparks | A61K 9/1275 264/4.1 |
| 2009/0110739 A1 | 4/2009 | Lacko et al. | |
| 2011/0256224 A1 | 10/2011 | Sigalov | |
| 2012/0232005 A1 | 9/2012 | Dasseux et al. | |

FOREIGN PATENT DOCUMENTS

| | | | | |
|---|---|---|---|---|
| EP | 2673296 B1 * | 10/2018 | ............. | A61K 47/50 |
| WO | WO-9917740 A1 * | 4/1999 | ............... | A61K 9/19 |

OTHER PUBLICATIONS

Zhihong Zhang, HDL-Mimicking Peptide-Lipid Nanoparticles with Improved Tumor Targeting, small 2010, 6, No. 3, 430-437.*
Di Bartolo, B. A.; et al., "The apolipoprotein A-I mimetic peptide ETC-642 exhibits anti-inflammatory properties that are comparable to high density lipoproteins" Atherosclerosis 2011, 217 (2), 395-400.

(Continued)

*Primary Examiner* — Julie Ha
*Assistant Examiner* — Erinne R Dabkowski
(74) *Attorney, Agent, or Firm* — Casimir Jones, SC; Robert A. Goetz

(57) ABSTRACT

The present invention relates to nanoparticles complexed with therapeutic agents configured for treating cardiovascular related disorders, and methods of synthesizing the same. In particular, the present invention is directed to compositions comprising synthetic HDL (sHDL) nanoparticles carrying therapeutic agents configured for treating cardiovascular related disorders, methods for synthesizing such sHDL nanoparticles, as well as systems and methods utilizing such sHDL nanoparticles (e.g., in diagnostic and/or therapeutic settings (e.g., for the delivery of therapeutic agents, imaging agents, and/or targeting agents (e.g., in cardiovascular disease diagnosis and/or therapy, etc.))).

13 Claims, 23 Drawing Sheets
Specification includes a Sequence Listing.

(56) References Cited

OTHER PUBLICATIONS

Gandhi, CXZ et al. "Liver X Receptor and Retinoid X Receptor Agonists Inhibit Inflammatory Responses of Microglia and Astrocytes" Journal of NeuroImmunology. Dec. 18, 2006; vol. 183, No. 1-2, pp. 1-18.
International Search Report and Written Opinion, International Patent Application No. PCT/US2016/024230, dated Sep. 22, 2016.
Marrache, S. et al. "Biodegradable Synthetic High-Density Lipoprotein Nanoparticles for Atherosclerosis." Proceedings of the National Academy of Sciences. May 13, 2013; vol. 110, No. 23; pp. 9445-9450.

* cited by examiner

HUVECs were treated with 1.0 mg/mL HDL (22A:DPPC, 1:2 w/w) containing different concentrations of S1P and released Nitric Oxide was measured in supernatants by ozone chemiluminescence. Blank 22A:DPPC HDL (1.0 mg/mL) and PBS were used as controls.

TO901317-encapsulated sHDL particles upregulated ABCA1 expression in macrophages T0901317-encapsulated sHDL particles enhance cholesterol efflux in macrophages

FIG. 8A

| C57BI/6 mice, one-LP injection (24 h) | |
|---|---|
| DMSO n=3 | |
| TO901317 n=3 | 0.5mg/kg |
| TO901317 n=3 | 1.5mg/kg |
| TO901317 n=3 | 10mg/kg |
| sHDL n=3 | 50mg/kg 22A |
| sHDL/TO n=3 | 50mg/kg 22A 0.5mg/kg |
| sHDL/TO n=3 | 50mg/kg 22A 1.5mg/kg |
| sHDL/TO n=3 | 50mg/kg 22A 3mg/kg |

Serum: HDL, LDL, TG
Liver: expression of lipogenesis related genes (SREBP1c, FAS, SCD1)

FIG. 8B

C57bl/6 mice treated with sHDL and/or LXR agonist

IP injection lipid profile 24 hours after injection

| Group | Tot chol | HDL | trigly | LDL |
|---|---|---|---|---|
| DMSO | 77 | 46 | 76 | 13 |
| TO 0.5 | 110 | 46 | 94 | 7 |
| TO 1.5 | 83 | 35 | 103 | 12 |
| TO 10 | 116 | 34 | 110 | 7 |
| sHDL | 90 | 51 | 73 | 13 |
| sHDL TO 0.5 | 80 | 44 | 76 | 12 |
| sHDL TO 1.5 | 90 | 43 | 73 | 14 |
| sHDL TO 3 | 89 | 48 | 72 | 10 |

FIG. 11
Effects on the expression of LXR target genes in monocytes isolated from blood
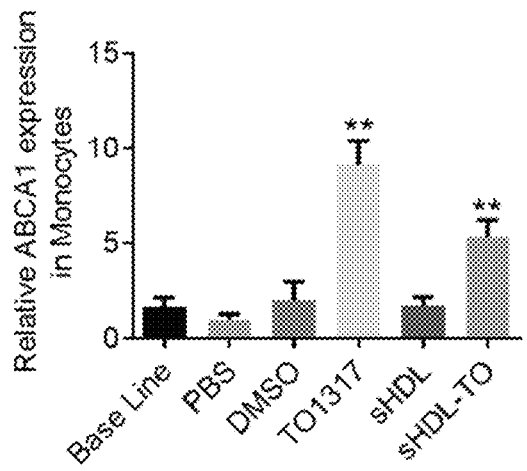
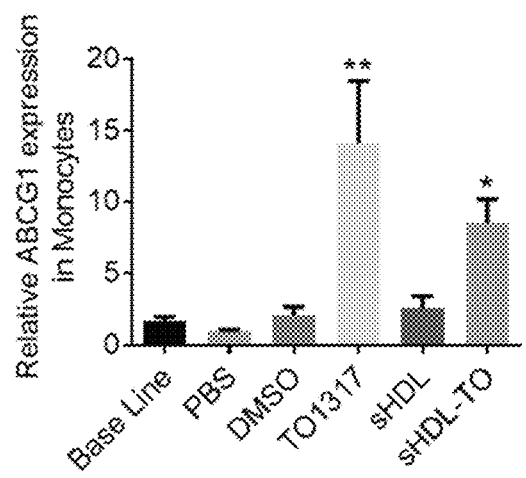

Free TO1317 increased liver TG accumulation

FIG. 13
sHDL-TO less potent than free TO in lipogenic gene induction in the liver
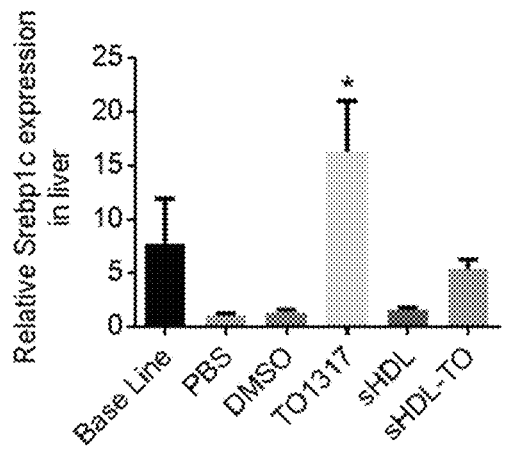
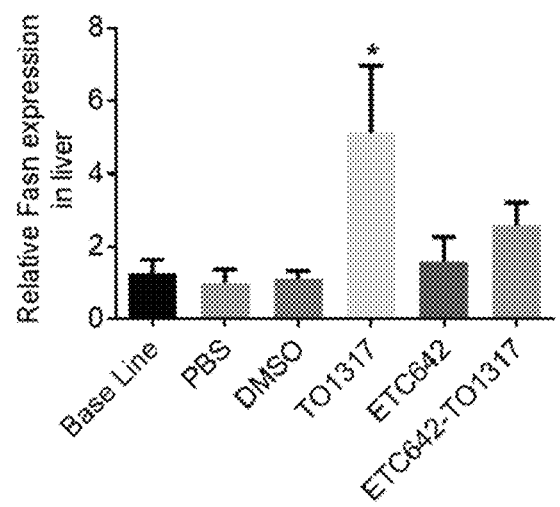

FIG. 16

Effects on ABCA1 expression in human macrophages (fold change)

|              | DMSO | Free compound | sHDL | sHDL-compound |
|--------------|------|---------------|------|---------------|
| TO901317     | 1    | 3.2           | 1    | 8.1           |
| Rosiglitazone| 1    | 2             | 1    | 2.9           |
| CD3254       | 1    | 3.9           | 1    | 34.7          |

FIG. 17

Effects on ABCG1 expression in human macrophages (fold change)

|              | DMSO | Free compound | sHDL | sHDL-compound |
|--------------|------|---------------|------|---------------|
| TO901317     | 1    | 54.4          | 1    | 441           |
| Rosiglitazone| 1    | 3.4           | 1    | 2.6           |
| CD3254       | 1    | 20.9          | 1    | 141.5         |

FIG. 18

Effects on SR-BI expression in human macrophages (fold change)

|              | DMSO | Free compound | sHDL | sHDL-compound |
|--------------|------|---------------|------|---------------|
| TO901317     | 1    | 1.3           | 1    | 4.5           |
| Rosiglitazone| 1    | 2.2           | 1    | 3.5           |
| CD3254       | 1    | 1.9           | 1    | 4.6           |

FIG. 19
Effects on cholesterol efflux in macrophages
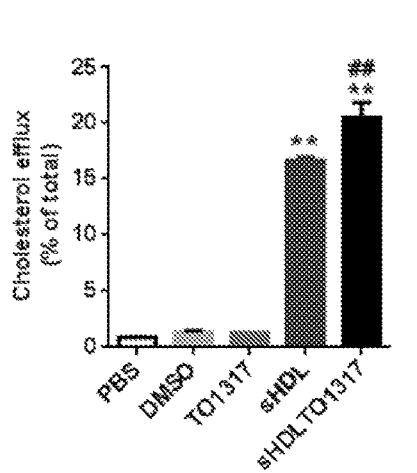
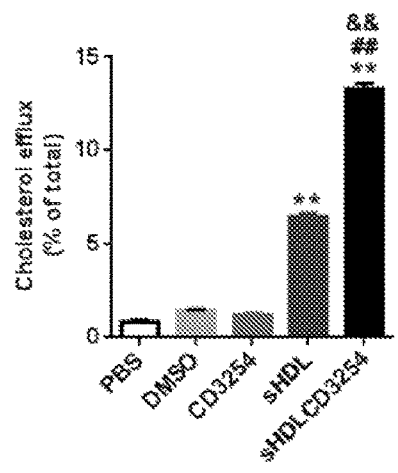

Effects of LXR agonists on atherosclerosis progression

Effects of RXR agonists on atherosclerosis progression

Effects of LXR agonists on lipid profile in apoE-deficient mice

Effects of RXR agonist on lipid profile in apoE-deficient mice

COMPOSITIONS AND METHODS FOR TREATING CARDIOVASCULAR RELATED DISORDERS

STATEMENT REGARDING FEDERALLY SPONSORED RESEARCH OR DEVELOPMENT

This invention was made with government support under GM008353, HL068878 and HL117491 awarded by the National Institutes of Health. The government has certain rights in the invention.

CROSS REFERENCE TO RELATED APPLICATIONS

The present invention is a national stage of International (PCT) Patent Application Serial No. PCT/US2016/024230, filed Mar. 25, 2016, which claims the priority benefit of U.S. Provisional Patent Application 62/138,193, filed Mar. 25, 2015, which are incorporated by reference in their entireties.

FIELD OF THE INVENTION

The present invention relates to nanoparticles complexed with therapeutic agents configured for treating cardiovascular related disorders, and methods of synthesizing the same. In particular, the present invention is directed to compositions comprising synthetic HDL (sHDL) nanoparticles carrying therapeutic agents configured for treating cardiovascular related disorders, methods for synthesizing such sHDL nanoparticles, as well as systems and methods utilizing such sHDL nanoparticles (e.g., in diagnostic and/or therapeutic settings (e.g., for the delivery of therapeutic agents, imaging agents, and/or targeting agents (e.g., in cardiovascular disease diagnosis and/or therapy, etc.))).

BACKGROUND OF THE INVENTION

The target of action on many cardiovascular medicines or preventive substances is in the vascular wall. Increase of cholesterol efflux, reduction of inflammation, reduction of oxidation and thrombosis at the vascular wall prevent or alleviate many pathologies (e.g., atherosclerosis, thrombosis, vascular disease) and will reduce heart attacks, strokes and other acute disease manifestation. Yet, there are only select vehicles or particles that accumulate at the vascular wall, enter through endothelial cell layer and are capable of delivery drugs/nutrients to the local vascular areas where they are needed.

Improved compositions and techniques for delivering therapeutic agents targeting vascular regions for therapeutic purposes are needed.

SUMMARY

Experiments conducted during the course of developing embodiments for the present invention demonstrated that sHDL nanoparticles selectively accumulate at specific vascular tissue regions (e.g., macrophages associated with atheromatous plaque regions), and improve the efficacy of therapeutic agents delivered to such vascular tissue regions with such sHDL nanoparticles. For example, increased sphingosine-1-phosphate (S1P) related nitric oxide release was demonstrated through its delivery within sHDL nanoparticices (see, Examples I and II). LXR, RXR, and PPARγ agonist-encapsulated sHDL nanoparticles were shown to induce significant upregulation of ABC transporters, resulting in increased cholesterol efflux in macrophage (see, Examples XVI, XVII, XVIII and XIX). RXR and LXR agonist-encapsulated sHDL nanoparticles were shown to attenuate atherosclerosis development in vivo at a low dosage (Examples XX and XXI). In addition, LXR agonist-encapsulated sHDL nanoparticles were shown to induce in vivo atherosclerosis regression while avoiding liver toxicity (e.g., hepatic steatosis) (Examples III and IV).

Accordingly, the present invention relates to nanoparticles complexed with therapeutic agents configured for treating cardiovascular related disorders, and methods of synthesizing the same. In particular, the present invention is directed to compositions comprising synthetic HDL (sHDL) nanoparticles carrying therapeutic agents configured for treating cardiovascular related disorders, methods for synthesizing such sHDL nanoparticles, as well as systems and methods utilizing such sHDL nanoparticles (e.g., in diagnostic and/or therapeutic settings (e.g., for the delivery of therapeutic agents, imaging agents, and/or targeting agents (e.g., in cardiovascular disease diagnosis and/or therapy, etc.))).

In certain embodiments, the present invention provides methods for preparing a synthetic HDL-therapeutic agent nanoparticle (sHDL-TA). The present invention is not limited to particular methods for preparing a sHDL-TA. In some embodiments, such methods comprise combining at least one phospholipid having a transition temperature, at least one therapeutic agent, and at least one HDL apolipoprotein in a solvent to produce a mixture; lyophilizing the mixture to produce a dried mixture; hydrating the dried mixture in an aqueous buffer to produce an aqueous mixture; and heating (e.g., thermocycling or incubating) the aqueous mixture above and below the phospholipid transition temperature to produce a sHDL-TA. In some embodiments, the therapeutic agent is configured to treat a cardiovascular disorder. In some embodiments, the HDL apolipoprotein is an HDL apolipoprotein mimetic.

In some embodiments, the solvent is glacial acetic acid. In some embodiments, the aqueous buffer PBS. In some embodiments, the heating is thermocycling. In some embodiments, the thermocycling occurs between 25 and 50° C.

The sHDL-TA nanoparticles are not limited to a particular size. In some embodiments, the average particle size of the sHDL-TA nanoparticle is between 6-20 nm (e.g., 6-14) (e.g., 8-10 nm).

Such methods are not limited to a particular HDL apolipoprotein. For example, in some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, pre-proApoA-I, proApoA-I, ApoA-I, preproApoA-II, proApoA-II, ApoA-II, preproApoA-1V, proApoA-1V, ApoA-IV, ApoA-V, preproApoE, proApoE, ApoE, preproApoA-1Milano, proApoA-IMilano ApoA-1Milano preproApoA-IParis , proApoA-IParis, and ApoA-IParis and peptide mimetics of these proteins mixtures thereof.

In some embodiments, the HDL apolipoprotein mimetic is an ApoA-I mimetic as described in Srinivasa, et al., 2014 Curr. Opinion Lipidology Vol. 25(4): 304-308, U.S. Pat. No. 6,743,778, 7,566,695, and/or U.S. Patent Application Publication Nos. 2003/0171277, 2006/0069030, 2009/0081293, 20110046056, 20130231459. In some embodiments, the the ApoA-I mimetic is described by any of SEQ ID NOs: 1-336. In some embodiments, the ApoA-I mimetic is an ApoA-I mimetic having the following amino acid sequence (PVLD-LFRELLNELLEALKQKLK) (SEQ ID NO: 4) (the "22A" ApoA-I mimetic).

Such methods are not limited to a particular phospholipid. In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

Such methods are not limited to a particular therapeutic agent. In some embodiments, the therapeutic agent is selected from the group consisting of a liver X receptor agonist, retinoid X receptor agonist, sphingosine-1-phosphate (S1P), angiotensin-converting enzyme (ACE) inhibitors (e.g., benazepril, enalapril, Lisinopril, perindopril, Ramipril), adenosine, alpha blockers (alpha adrenergic antagonist medications) (e.g., clonidine, guanabenz, labetalol, phenoxybenzamine, terazosin, doxazosin, guanfacine, methyldopa, prazosin), angtiotensin II receptor blockers (ARBs) (e.g., candesartan, irbesartan, olmesartan medoxomil, telmisartan, eprosartan, losartan, tasosartan, valsartan), antiocoagulants (e.g., heparin fondaparinux, warfarin, ardeparin, enoxaparin, reviparin, dalteparin, nadroparin, tinzaparin), antiplatelet agents (e.g., abciximab, clopidogrel, eptifibatide, ticlopidine, cilostazol, dipyridamole, sulfinpyrazone, tirofiban), beta blockers (e.g., acebutolol, betaxolol, carteolol, metoprolol, penbutolol, propranolol, atenolol, bisoprolol, esmolol, nadolol, pindolol, timolol), calcium channel blockers (e.g., amlopidine, felodipine, isradipine, nifedipine, verapamil, diltiazem, nicardipine, nimodipine, nisoldipine), diuretics, aldosterone blockers, loop diuretics (e.g., bumetanide, furosemide, ethacrynic acid, torsemide), potassium-sparing diuretics, thiazide diuretics (e.g., chlorothiazide, chlorthalidone, hydrochlorothiazide, hydroflumethiazide, methyclothiazide, metolazone, polythiazide, quinethazone, trichlormethiazide), inoptropics, bile acid sequestrants (e.g., cholestyramine, coletipol, colesevelam), fibrates (e.g., clofibrate, gemfibrozil, fenofibrate), statins (e.g., atorvastatinm, lovastatin, simvastatin, fluvastatin, pravastatin), selective cholesterol absorption inhibitors (e.g., ezetimibe), potassium channel blockers (e.g., amidarone, ibutilide, dofetilide), sodium channel blockers (e.g., disopyramide, mexiletine, procainamide, quinidine, flecainide, moricizine, propafenone), thrombolytic agents (e.g., alteplase, reteplase, tenecteplase, anistreplase, streptokinase, urokinase), vasoconstrictors, vasodilators (e.g., hydralazine, minoxidil, mecamylamine, isorbide dintrate, isorbide mononitrate, nitroglycerin).

In some embodiments, the liver X receptor agonist is selected from TO901317, ATI-111, LXR-623, XL-652, hypocholamide, GW3965, N,N-dimethyl-3beta-hydroxy-cholenamide (DMHCA), 22(R)-hydroxycholesterol, 24(S)-hydroxycholesterol, (−)anthrabenzoxocinone and (−)bis-chloroanthrabenzoxocinone ((−)-BABX).

In some embodiments, the retinoid X receptor agonist is selected from Bexarotene, CD3254, Docosahexaenoic acid, fluorobexarotene, isotretinoin, retinoic acid, SR11237, fenretinide, HX630, liarozole dihydrochloride, LG100754 and LG101506.

In some embodiments, the combined LXR and RXR agonists are selected from TO901317, ATI-111, LXR-623, XL-652, hypocholamide, GW3965, N,N-dimethyl-3beta-hydroxy-cholenamide (DMHCA), 22(R)-hydroxycholesterol, 24(S)-hydroxycholesterol, (−)anthrabenzoxocinone, (−)bischloroanthrabenzoxocinone ((−)-BABX), Bexarotene, CD3254, Docosahexaenoic acid, fluorobexarotene, isotretinoin, retinoic acid, SR11237, fenretinide, HX630, liarozole dihydrochloride, LG100754 and LG101506.

In some embodiments, the methods further comprise combining an imaging agent (e.g., a lipophilic near infrared fluorescent dye or a nuclear imaging agent) with the combining of at least one phospholipid having a transition temperature, at least one therapeutic agent, and at least one HDL apolipoprotein in a solvent to produce a mixture. In some embodiments, the lipophilic near infrared fluorescent dye is DiD.

In certain embodiments, the present invention provides compositions comprising a synthetic HDL-therapeutic agent nanoparticle (sHDL-TA). In some embodiments, the sHDL-TA comprises a mixture of at least one phospholipid, at least one therapeutic agent, and at least one HDL apolipoprotein. In some embodiments, the therapeutic agent is configured to treat a cardiovascular disorder. In some embodiments, the HDL apolipoprotein is an HDL apolipoprotein mimetic.

Such compositions are not limited to a particular HDL apolipoprotein. In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, preproApoA-I, proApoA-I, ApoA-I, preproApoA-II, proApoA-II, ApoA-II, preproApoA-1V, proApoA-1V, ApoA-IV, ApoA-V, preproApoE, proApoE, ApoE, preproApoA-1Milano, proApoA-IMilano ApoA-1Milano preproApoA-IParis, proApoA-IParis, and ApoA-IParis and peptide mimetics of these proteins mixtures thereof.

Such compositions are not limited to a particular phospholipid. In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramidel], 1,2-dihexadecanoyl-sn-glycero-3-phosphoethanolamine-N-[4-(p-maleimidophenyl)butyramidel], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the HDL apolipoprotein mimetic is an ApoA-I mimetic. In some embodiments, the ApoA-I mimetic is 22A ApoA-I mimetic. In some embodiments, the ApoA-I mimetic is described by any of SEQ ID NOs: 1-336.

Such compositions are not limited to a therapeutic agent. For example, in some embodiments, the therapeutic agent is as disclosed herein. In some embodiments, the therapeutic agent is a liver X receptor agonist (e.g., TO901317, ATI-111, LXR-623, XL-652, hypocholamide, GW3965, N,N-dimethyl-3beta-hydroxy-cholenamide (DMHCA), 22(R)-hydroxycholesterol, 24(S)-hydroxycholesterol, (−)anthrabenzoxocinone and (−)bischloroanthrabenzoxocinone ((−)-BABX). In some embodiments, the therapeutic agent is a liver X receptor agonist (e.g., CD3254, Bexarotene, Docosahexaenoic acid, fluorobexarotene, isotretinoin, retinoic acid, SR11237, fenretinide, HX630, liarozole dihydrochloride, LG100754 and LG101506). In some embodiments, the therapeutic agent is a combination of LXR and RXR agonists.

The sHDL-TA nanoparticles are not limited to a particular size. In some embodiments, the average particle size of the sHDL-TA nanoparticle is between 6-20 nm (e.g., 6-14) (e.g., 8-10 nm).

In some embodiments, an imaging agent (e.g., a lipophilic near infrared fluorescent dye or a nuclear imaging agent) is contained within the sHDL-TA mixture of at least one phospholipid, at least one therapeutic agent, and at least one HDL apolipoprotein. In some embodiments, the lipophilic near infrared fluorescent dye is DiD.

In certain embodiments, the present invention provides methods of treating a subject having a cardiovascular related disorder, comprising administering to the subject a therapeutically effective amount of a composition comprising a synthetic HDL-therapeutic agent nanoparticle (sHDL-TA), wherein the sHDL-TA comprises a mixture of at least one phospholipid, at least one therapeutic agent, and at least one HDL apolipoprotein, wherein the therapeutic agent is configured to treat a cardiovascular disorder, wherein the HDL apolipoprotein is an HDL apolipoprotein mimetic.

Such methods are not limited to treating a particular cardiovascular related disorder. In some embodiments, the cardiovascular related disorder is one or more disorders selected from the group consisting of atherosclerosis, coronary artery disease, cardiomyopathy, hypertensive heart disease, heart failure, pulmonary heart disease, cardiac dysrhythmias, inflammatory heart disease (e.g., endocarditis, inflammatory cardiomegaly, myocarditis), vulvular heart disease, cerebrovascular disease, peripheral arterial disease, congenital heart disease, and rheumatic heart disease.

In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, preproApoA-I, proApoA-I, ApoA-I, preproApoA-II, proApoA-II, ApoA-II, preproApoA-1V, proApoA-1V, ApoA-IV, ApoA-V, preproApoE, proApoE, ApoE, preproApoA-1Milano, proApoA-IMilano ApoA-1Milano preproApoA-IParis , proApoA-IParis, and ApoA-IParis and peptide mimetics of these proteins mixtures thereof.

In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl) butyramide], 1,2-dihexadecanoyl-sn-glycero-3-phosphoethanolamine-N-[4-(p-maleimidomethyl) cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the HDL apolipoprotein mimetic is an ApoA-I mimetic. In some embodiments, the ApoA-I mimetic is 22A ApoA-I mimetic.

In some embodiments, the average particle size of the sHDL-TA nanoparticle is between 6-20 nm (e.g., 8-10 nm).

Such methods are not limited to a therapeutic agent. For example, in some embodiments, the therapeutic agent is as disclosed herein. In some embodiments, the therapeutic agents are liver X receptor agonists (e.g., TO901317) and/or retinoid X receptor agonists (e.g., CD3254).

In some embodiments, the methods further comprise an imaging agent (e.g., a lipophilic near infrared fluorescent dye or a nuclear imaging agent) within the sHDL-TA mixture of at least one phospholipid, at least one therapeutic agent, and at least one HDL apolipoprotein. In some embodiments, the lipophilic near infrared fluorescent dye is DiD.

In certain embodiments, the present invention provides methods of targeting a therapeutic agent to an atheromatous plaque region within a biological sample comprising producing a therapeutic agent encapsulated within a synthetic HDL (sHDL) nanoparticle, wherein the sHDL nanoparticle accumulates at atheromatous plaque regions, and exposing the therapeutic agent encapsulated within the sHDL nanoparticle to the biological sample such that the therapeutic agent encapsulated within the sHDL nanoparticle accumulates at atheromatous plaque regions within the biological sample.

Such methods are not limited to a particular manner of producing the therapeutic agent encapsulated within a synthetic HDL (sHDL) nanoparticle. In some embodiments, such producing comprises combining at least one phospholipid having a transition temperature, at least one therapeutic agent, and at least one HDL apolipoprotein in a solvent to produce a mixture; lyophilizing the mixture to produce a dried mixture; hydrating the dried mixture in an aqueous buffer to produce an aqueous mixture; heating (e.g., thermocycling or incubating) the aqueous mixture above and below the phospholipid transition temperature to produce a therapeutic agent encapsulated within a sHDL nanoparticle. In some embodiments, the solvent is glacial acetic acid. In some embodiments, the aqueous buffer PBS. In some embodiments, the heating is thermocycling. In some embodiments, the thermocycling occurs between 25 and 50° C. In some embodiments, the average particle size of the therapeutic agent encapsulated within the sHDL nanoparticle is between 6-20 nm (e.g., 6-14) (e.g., 8-10 nm). In some embodiments, the producing further comprises combining an imaging agent (e.g., a lipophilic near infrared fluorescent dye or a nuclear imaging agent) with the combining of at least one phospholipid having a transition temperature, at least one therapeutic agent, and at least one HDL apolipoprotein in a solvent to produce a mixture. In some embodiments, the lipophilic near infrared fluorescent dye is DiD.

Such methods are not limited to a particular therapeutic agent. In some embodiments, the therapeutic agent is configured to treat a cardiovascular disorder. In some embodiments, the therapeutic agent is as disclosed herein. In some embodiments, the therapeutic agents are liver X receptor agonists (e.g., TO901317) and/or retinoid X receptor agonists (e.g., CD3254).

Such methods are not limited to a particular HDL apolipoprotein. In some embodiments, the HDL apolipoprotein is an HDL apolipoprotein mimetic the HDL apolipoprotein is selected from the group consisting of apolipoprotein A-I (apo apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, preproApoA-I, proApoA-I, ApoA-I, preproApoA-II, proApoA-II, ApoA-II, preproApoA-1V, proApoA-1V, ApoA-IV, ApoA-V, preproApoE, proApoE, ApoE, preproApoA-1Milano, proApoA-IMilano ApoA-1Milano preproApoA-IParis , proApoA-IParis, and ApoA-IParis and peptide mimetics of these proteins mixtures thereof. In some embodiments, the HDL apolipoprotein mimetic is an ApoA-I mimetic. In some embodiments, the ApoA-I mimetic is 22A ApoA-I mimetic. In some embodiments, the ApoA-I mimetic is described by any of SEQ ID NOs: 1-336.

Such methods are not limited to a particular type of phospholipid. In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

Such methods are not limited a particular type of biological sample. In some embodiments, the biological sample is an in vivo, in vitro or an ex vivo sample. In some embodiments, the biological sample is a living mammal.

In certain embodiments, the present invention provides methods of upregulating ABCA1 and ABCG1 expression within a biological sample, comprising exposing a composition comprising a synthetic HDL-TA nanoparticle to the biological sample, wherein the exposing results in upregulation of ABCA1 and ABCG1 expression within the biological sample. In some embodiments, the sHDL-TA nanoparticle comprises a mixture of at least one phospholipid, at least one therapeutic agent, and at least one HDL apolipoprotein. In some embodiments, the therapeutic agent is a liver X receptor agonist and/or a retinoid X receptor agonist. In some embodiments, the HDL apolipoprotein is an HDL apolipoprotein mimetic. In some embodiments, the therapeutic agents are liver X receptor agonists (e.g., TO901317) and retinoid X receptor agonists (e.g., CD3254).

Such methods are not limited a particular type of biological sample. In some embodiments, the biological sample is an in vivo, in vitro or an ex vivo sample. In some embodiments, the biological sample is a living mammal.

Such methods are not limited to a particular HDL apolipoprotein. In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, preproApoA-I, proApoA-I, ApoA-I, preproApoA-II, proApoA-II, ApoA-II, preproApoA-1V, proApoA-1V, ApoA-IV, ApoA-V, preproApoE, proApoE, ApoE, preproApoA-1Milano, proApoA-IMilano ApoA-1Milano preproApoA-IParis , proApoA-IParis, and ApoA-IParis and peptide mimetics of these proteins mixtures thereof. In some embodiments, the HDL apolipoprotein mimetic is an ApoA-I mimetic. In some embodiments, the ApoA-I mimetic is 22A ApoA-I mimetic.

Such methods are not limited to a particular phospholipid. In some embodiments, the phospholipid is selected from the group consisting of dipalmitoylphosphatidylcholine (DPPC), phosphatidylcholine, phosphatidylinositol, phosphatidylserine, phosphatidylethanolamine, and combinations thereof.

In some embodiments, the average particle size of the sHDL-TA nanoparticle is between 6-20 nm (e.g., 6-14) (e.g., 8-10 nm).

In some embodiments, the methods further comprise an imaging agent (e.g., a lipophilic near infrared fluorescent dye or a nuclear imaging agent) within the sHDL-TA mixture of at least one phospholipid, at least one liver X receptor agonist, at least one retinoid X receptor agonist, and at least one HDL apolipoprotein. In some embodiments, the lipophilic near infrared fluorescent dye is DiD.

In some embodiments, the upregulation of ABCA1 and ABCG1 expression within the biological sample occurs within macrophages associated with atheromatous plaque regions within the biological sample. In some embodiments, the upregulation of ABCA1 and ABCG1 expression further induces cholesterol efflux from the macrophages associated with atheromatous plaque regions within the biological sample.

In certain embodiments, the present invention provides methods of inducing cholesterol efflux within a biological sample, comprising exposing a composition comprising a synthetic HDL-TA nanoparticle to the biological sample, wherein the biological sample comprises cells comprising macrophages, wherein the exposing results in cholesterol efflux from the macrophages within the biological sample, wherein the sHDL-TA nanoparticle comprises a mixture of at least one phospholipid, at least one therapeutic agent, and at least one HDL apolipoprotein, wherein the therapeutic agent is a liver X receptor agonist;

wherein the HDL apolipoprotein is an HDL apolipoprotein mimetic.

In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, preproApoA-I, proApoA-I, ApoA-I, preproApoA-II, proApoA-II, ApoA-II, preproApoA-1V, proApoA-1V, ApoA-IV, ApoA-V, preproApoE, proApoE, ApoE, preproApoA-1Milano, proApoA-IMilano ApoA-1Milano preproApoA-IParis, proApoA-IParis, and ApoA-IParis and peptide mimetics of these proteins mixtures thereof.

In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the HDL apolipoprotein mimetic is an ApoA-I mimetic. In some embodiments, the ApoA-I mimetic is 22A ApoA-I mimetic. In some embodiments, the ApoA-I mimetic is described by any of SEQ ID NOs: 1-336.

In some embodiments, the average particle size of the sHDL-TA nanoparticle is between 6-20 nm (e.g., 6-14) (e.g., 8-10 nm).

In some embodiments, the liver X receptor agonist is TO901317.

In some embodiments, the retinoid X receptor agonist is CD3254.

In some embodiments, the methods further comprise an imaging agent (e.g., a lipophilic near infrared fluorescent dye or a nuclear imaging agent) within the sHDL-TA mixture of at least one phospholipid, at least one liver X receptor agonist, at least one retinoid X receptor agonist, and at least one HDL apolipoprotein. In some embodiments, the lipophilic near infrared fluorescent dye is DiD.

In some embodiments, the cholesterol efflux from the macrophages within the biological sample occurs within macrophages associated with atheromatous plaque regions within the biological sample. In some embodiments, the cholesterol efflux coincides with upregulation of ABCA1 and ABCG1 expression within the macrophages associated with atheromatous plaque regions within the biological sample.

Such methods are not limited a particular type of biological sample. In some embodiments, the biological sample is an in vivo, in vitro or an ex vivo sample. In some embodiments, the biological sample is a living mammal.

In certain embodiments, the present invention provides methods for treating atherosclerotic lesions within a subject, comprising administering to the subject a composition comprising a therapeutically effective amount of a composition comprising a synthetic HDL-therapeutic agent nanoparticle (sHDL-TA), wherein the sHDL-TA comprises a mixture of at least one phospholipid, at least one liver X receptor agonist, at least one retinoid X receptor, and at least one HDL apolipoprotein, wherein the HDL apolipoprotein is an HDL apolipoprotein mimetic, wherein the administering results in accumulation of the sHDL-TA at atherosclerotic lesions within the subject, wherein accumulation of the sHDL-TA at the atherosclerotic lesions within the subject results in cholesterol efflux from macrophages at the atherosclerotic lesions. In some embodiments, the Liver X Receptor agonist is TO901317. In some embodiments, the retinoid X receptor agonist is CD3254.

In some embodiments, administering the composition comprising a sHDL-TA nanoparticle results in reduced liver related lipogenesis in comparison to administration of a liver X receptor agonist not encapsulated within a sHDL nanoparticle. In some embodiments, the liver related lipogenesis is measured by SREBP1c expression.

In some embodiments, the cholesterol efflux from macrophages at the atherosclerotic lesions further involves upregulation of ABCA1 and ABCG1 expression within the macrophages.

Such methods are not limited to a particular HDL apolipoprotein. In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, preproApoA-I, proApoA-I, ApoA-I, preproApoA-II, proApoA-II, ApoA-II, pre-proApoA-1V, proApoA-1V, ApoA-IV, ApoA-V, pre-proApoE, proApoE, ApoE, preproApoA-1Milano, proApoA-IMilano ApoA-1Milano preproApoA-IParis, proApoA-IParis, and ApoA-IParis and peptide mimetics of these proteins mixtures thereof. In some embodiments, the HDL apolipoprotein mimetic is an ApoA-I mimetic. In some embodiments, the ApoA-I mimetic is 22A ApoA-I mimetic. In some embodiments, the ApoA-I mimetic is described by any of SEQ ID NOs: 1-336.

Such methods are not limited to a particular phospholipid. In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the average particle size of the sHDL-TA nanoparticle is between 6-20 nm (e.g., 6-14) (e.g., 8-10 nm).

In some embodiments, the methods further comprise an imaging agent (e.g., a lipophilic near infrared fluorescent dye or a nuclear imaging agent) within the sHDL-TA mixture of at least one phospholipid, at least one liver X receptor agonist, at least one retinoid X receptor agonist, and at least one HDL apolipoprotein. In some embodiments, the lipophilic near infrared fluorescent dye is DiD.

In certain embodiments, the present invention provides methods of inducing nitric oxide efflux within a biological sample, comprising exposing a composition comprising a synthetic HDL-TA nanoparticle to the biological sample, wherein the biological sample comprises cells comprising endothelial cells, wherein the exposing results in nitric oxide efflux from the endothelial cells within the biological sample, wherein the sHDL-TA nanoparticle comprises a mixture of at least one phospholipid, at least one therapeutic agent, and at least one HDL apolipoprotein, wherein the therapeutic agent is sphingosine-1-phosphate; wherein the HDL apolipoprotein is an HDL apolipoprotein mimetic.

Such methods are not limited to a particular HDL apolipoprotein. In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, preproApoA-I, proApoA-I, ApoA-I, preproApoA-II, proApoA-II, ApoA-II, pre-proApoA-1V, proApoA-1V, ApoA-IV, ApoA-V, pre-proApoE, proApoE, ApoE, preproApoA-1Milano, proApoA-IMilano ApoA-1Milano preproApoA-IParis, proApoA-IParis, and ApoA-IParis and peptide mimetics of these proteins mixtures thereof. In some embodiments, the HDL apolipoprotein mimetic is an ApoA-I mimetic. In some embodiments, the ApoA-I mimetic is 22A ApoA-I mimetic.

Such methods are not limited to a particular phospholipid. In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)

butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the average particle size of the sHDL-TA nanoparticle is between 6-20 nm (e.g., 6-14) (e.g., 8-10 nm).

In some embodiments, the methods further comprise an imaging agent (e.g., a lipophilic near infrared fluorescent dye or a nuclear imaging agent) within the sHDL-TA mixture of at least one phospholipid, at least one liver X receptor agonist, at least one retinoid X receptor agonist, and at least one HDL apolipoprotein. In some embodiments, the lipophilic near infrared fluorescent dye is DiD.

Such methods are not limited a particular type of biological sample. In some embodiments, the biological sample is an in vivo, in vitro or an ex vivo sample. In some embodiments, the biological sample is a living mammal.

In certain embodiments, the present invention provides methods of detecting the presence of atherosclerotic lesions in a subject, comprising administering to the subject compositions comprising synthetic HDL-imaging agent (sHDL-IA) nanoparticles, wherein the synthetic HDL-IA nanoparticles are known to accumulate at atherosclerotic lesions, wherein the sHDL-IA nanoparticles comprise a mixture of at least one phospholipid, at least one imaging agent, and at least one HDL apolipoprotein, imaging the amount and location of the sHDL-IA within the subject, wherein determination of imaging within vascular regions indicates the presence of atherosclerotic lesions within the subject, wherein the HDL apolipoprotein is selected from the group consisting of apolipoprotein A-I (apo apolipoprotein A-II (apo A-II), apolipoprotein A4 (apo A4), apolipoprotein Cs (apo Cs), and apolipoprotein E (apo E), wherein the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the HDL apolipoprotein mimetic is an ApoA-I mimetic. In some embodiments, the ApoA-I mimetic is 22A ApoA-I mimetic. In some embodiments, the ApoA-I mimetic is described by any of SEQ ID NOs: 1-336. In some embodiments, the average particle size of the sHDL-IA nanoparticle is between 6-20 nm (e.g., 6-14) (e.g., 8-10 nm).

In some embodiments, the methods further comprise combining a therapeutic agent with the mixture of at least one phospholipid, at least one imaging agent, and at least one HDL apolipoprotein. In some embodiments, the therapeutic agent is as disclosed herein.

In some embodiments, the imaging agent is a lipophilic near infrared fluorescent dye. In some embodiments, the lipophilic near infrared fluorescent dye is DiD.

In certain embodiments, the present invention provides kits comprising at least one phospholipid, at least one therapeutic agent, and at least one HDL apolipoprotein. In some embodiments, the kits further comprise at least one imaging agent.

In some embodiments, the therapeutic agent is as disclosed herein.

In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, preproApoA-I, proApoA-I, ApoA-I, preproApoA-II, proApoA-II, ApoA-II, preproApoA-1V, proApoA-1V, ApoA-IV, ApoA-V, preproApoE, proApoE, ApoE, preproApoA-1Milano, proApoA-IMilano ApoA-1Milano preproApoA-IParis , proApoA-IParis, and ApoA-IParis and peptide mimetics of these proteins mixtures thereof. In some embodiments, the HDL apolipoprotein mimetic is an ApoA-I mimetic. In some embodiments, the ApoA-I mimetic is 22A ApoA-I mimetic. In some embodiments, the ApoA-I mimetic is described by any of SEQ ID NOs: 1-336.

In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In certain embodiments, the present invention provides methods for preparing a synthetic HDL-therapeutic agent nanoparticle (sHDL-TA) comprising combining at least one phospholipid having a transition temperature, at least one therapeutic agent, and at least one HDL apolipoprotein in a solvent to produce a mixture; lyophilizing the mixture to produce a dried mixture; hydrating the dried mixture in an aqueous buffer to produce an aqueous mixture; incubating the aqueous mixture above and below the phospholipid transition temperature to produce a sHDL-TA; wherein the therapeutic agent is configured to treat a cardiovascular disorder; wherein the HDL apolipoprotein is an HDL apolipoprotein mimetic.

In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein mimetic is an ApoA-I mimetic. In some embodiments, the ApoA-I mimetic is described by any of SEQ ID NOs: 1-336.

In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3- phosphoethanolamine-N-[4-(p-maleimidomethyl) cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the therapeutic agent is as disclosed herein.

In some embodiments, the solvent is organic solvent. In some embodiments, the aqueous buffer PBS. In some embodiments, the incubating occurs between 35 and 55° C.

In some embodiments, the average particle size of the sHDL-TA nanoparticle is between 6-20 nm (e.g., 6-14) (e.g., 8-10 nm).

In some embodiments, the methods further comprise combining an imaging agent with the combining of at least one phospholipid having a transition temperature, at least one therapeutic agent, and at least one HDL apolipoprotein in a solvent to produce a mixture. In some embodiments, the imaging agent is a lipophilic near infrared fluorescent dye or a nuclear imaging agent.

In certain embodiments, the present invention provides compositions comprising a synthetic HDL-therapeutic agent nanoparticle (sHDL-TA), wherein the sHDL comprises at least one HDL apolipoprotein and at least one phospholipid, wherein the sHDL-TA has a therapeutic agent to sHDL ratio of 0.1-10% wt/wt, 60-66% wt/wt, or 30/33% wt/wt.

In certain embodiments, the present invention provides compositions comprising a synthetic HDL-therapeutic agent/imaging agent nanoparticle (sHDL-TA/IA), wherein the sHDL comprises at least one HDL apolipoprotein and at least one phospholipid, wherein the sHDL-TA/IA has a (therapeutic agent/imaging agent) to (sHDL) ratio of 0.1-10% wt/wt, 60-66% wt/wt, or 30/33% wt/wt.

In certain embodiments, the present invention provides compositions comprising a synthetic HDL-therapeutic agent nanoparticle (sHDL-TA), wherein the sHDL comprises at least one HDL apolipoprotein and at least one phospholipid, wherein the therapeutic agent is between 0.01-20% by weight of the sHDL-TA, wherein the sHDL is between 80-99.99% by weight of the sHDL-TA. In some embodiments, the therapeutic agent is between 1-10% by weight of the sHDL-TA.

In certain embodiments, the present invention provides compositions comprising a synthetic HDL-therapeutic agent-imaging agent nanoparticle (sHDL-TA/IA), wherein the sHDL comprises at least one HDL apolipoprotein and at least one phospholipid, wherein the therapeutic agent-imaging agent is between 0.01-20% by weight of the sHDL-TA/IA, wherein the sHDL is between 80-99.99% by weight of the sHDL-TA/IA. In some embodiments, the therapeutic agent-imaging agent is between 1-10% by weight of the sHDL-TA/IA.

Additional embodiments will be apparent to persons skilled in the relevant art based on the teachings contained herein.

BRIEF DESCRIPTION OF THE DRAWINGS

FIG. 8A and 8B shows the effects of TO901317-encapsulated sHDL particles on plasma lipids in C57BL/6J Mice.

FIG. 11 shows TO901317-encapsulated sHDL nanoparticles can activate ABCA1 and ABCG1 expression in monocytes in vivo.

FIG. 13 shows TO901317-encapsulated sHDL nanoparticles induced less SREBP-1c and FAS expression in the liver.

FIG. 16 shows compound-encapsulated sHDL nanoparticles can enhance ABCA1 expression compared to sHDL nanoparticle-treated and free compound-treated macrophages.

FIG. 17 shows compound-encapsulated sHDL nanoparticles can enhance ABCG1 expression compared to sHDL nanoparticle-treated and free compound-treated macrophages.

FIG. 18 shows compound-encapsulated sHDL nanoparticles can enhance SR-BI expression compared to sHDL nanoparticle-treated and free compound-treated macrophages.

FIG. 19 shows compound-encapsulated sHDL nanoparticles can enhance cholesterol efflux compared to sHDL nanoparticle-treated and free compound-treated macrophages.

DEFINITIONS

Figure 1:
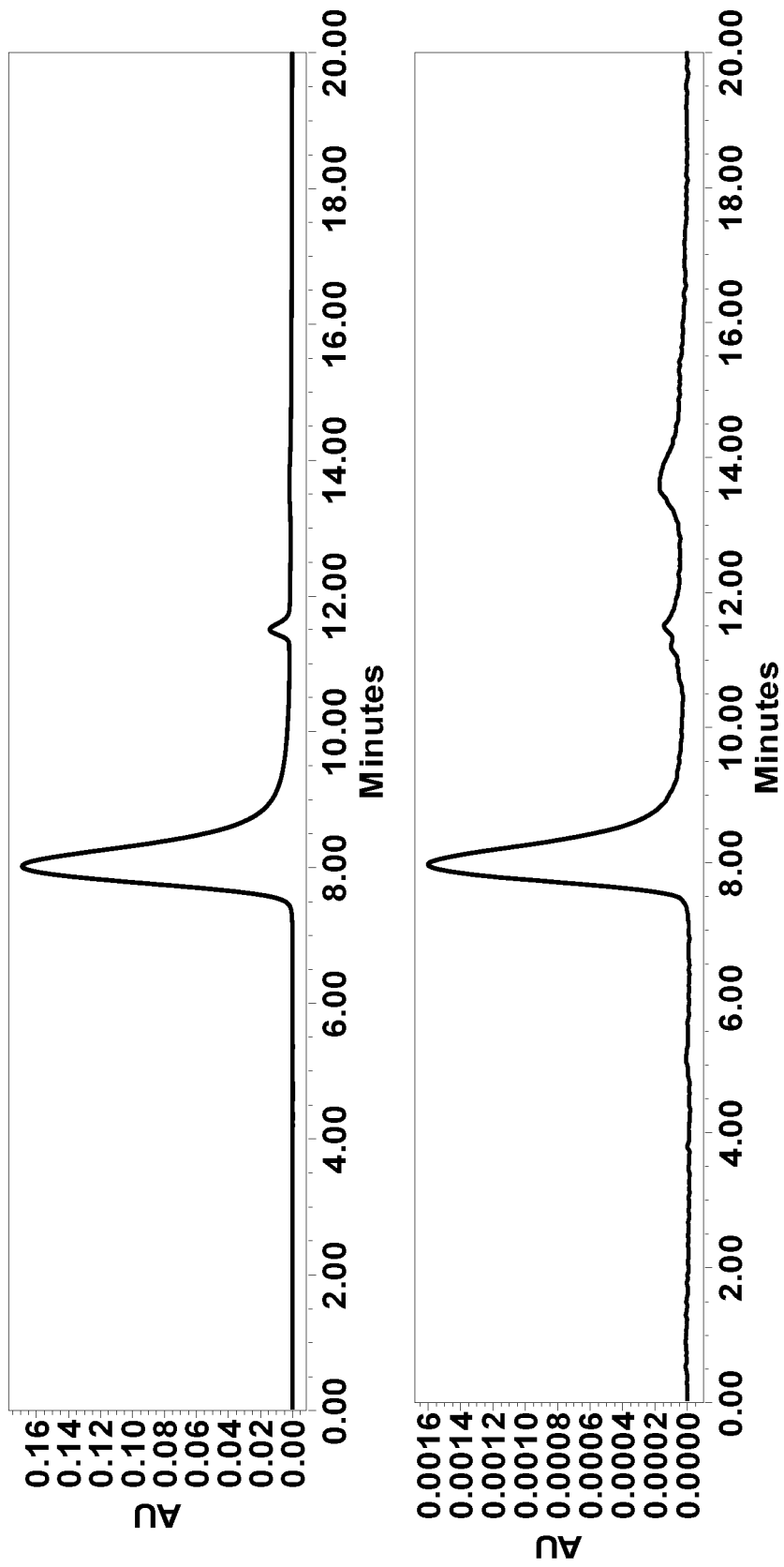
FIG. 1: GPC analysis of S1P-HDL—22A:DPPC containing 10 nmol S1P; detection wavelength of A) 220 nm and B) 280 nm; peak at 8.12 minutes corresponds to HDL particle (Example 1).

To facilitate an understanding of the present invention, a number of terms and phrases are defined below:

As used here, the term "lipids" refer to fatty substances that are insoluble in water and include fats, oils, waxes, and related compounds. They may be either made in the blood (endogenous) or ingested in the diet (exogenous). Lipids are essential for normal body function and whether produced from an exogenous or endogenous source, they must be transported and then released for use by the cells. The production, transportation and release of lipids for use by the cells is referred to as lipid metabolism. While there are several classes of lipids, two major classes are cholesterol and triglycerides. Cholesterol may be ingested in the diet and manufactured by the cells of most organs and tissues in the body, primarily in the liver. Cholesterol can be found in its free form or, more often, combined with fatty acids as what is called cholesterol esters.

As used herein the term, "lipoproteins" refer to spherical compounds that are structured so that water-insoluble lipids are contained in a partially water-soluble shell. Depending on the type of lipoprotein, the contents include varying amounts of free and esterified cholesterol, triglycerides and apoproteins or apolipoproteins. There are five major types of lipoproteins, which differ in function and in their lipid and apoprotein content and are classified according to increasing density: (i) chylomicrons and chylomicron remnants, (ii) very low density lipoproteins ("VLDL"), (iii) intermediate-density lipoproteins ("IDL"), (iv) low-density lipoproteins ("LDL"), and (v) high-density lipoproteins ("HDL"). Cholesterol circulates in the bloodstream as particles associated with lipoproteins.

As used herein, the term "HDL" or "high density lipoprotein" refers to high-density lipoprotein. HDL comprises a complex of lipids and proteins in approximately equal amounts that functions as a transporter of cholesterol in the blood. HDL is mainly synthesized in and secreted from the liver and epithelial cells of the small intestine. Immediately after secretion, HDL is in a form of a discoidal particle containing apolipoprotein A-I (also called apoA-I) and phospholipid as its major constituents, and also called nascent HDL. This nascent HDL receives, in blood, free cholesterol from cell membranes of peripheral cells or produced in the hydrolysis course of other lipoproteins, and forms mature spherical HDL while holding, at its hydrophobic center, cholesterol ester converted from said cholesterol by the action of LCAT (lecithin cholesterol acyltransferase). HDL plays an extremely important role in a lipid metabolism process called "reverse cholesterol transport", which takes, in blood, cholesterol out of peripheral tissues and transports it to the liver. High levels of HDL are associated with a decreased risk of atherosclerosis and coronary heart disease (CHD) as the reverse cholesterol transport is considered one of the major mechanisms for HDL's prophylactic action on atherosclerosis.

As used herein, the terms "synthetic HDL," "sHDL," "reconstituted HDL", or "rHDL" refer to a particle structurally analogous to native HDL, composed of a lipid or lipids in association with at least one of the proteins of HDL, preferably Apo A-I or a mimetic thereof, and which exhibits all of the known physiological functions of HDL. Typically, the components of sHDL may be derived from blood, or produced by recombinant technology.

As used herein, the term "atherosclerosis" refers to a cardiovascular related disorder. Generally, atherosclerosis begins with an injury to the inner wall of an artery (endothelium or endothelial cells). Once the inner wall is damaged, a combination of biological processes can lead to the accumulation of the plaque. In response to the injury, macrophages accumulate at the site and migrate beneath the inner layer. The macrophages then begin to absorb fatty substances from the blood and become foam cells. An accumulation of foam cells and other substances, such as proliferating smooth muscle cells, contribute to the formation of plaque and eventually forms bulges in the artery wall. Over time, as the bulges continue to absorb fatty substances, plaque accumulations (atheromatous plaque regions or atherosclerotic plaques) narrow the vessel lumen and occlude the blood flow. Further, plaque accumulation may cause blood vessel walls to harden and lose their elasticity, which can increase resistance to blood flow and raise blood pressure. As a result, vascular diseases are considered a progressive illness with symptoms often not evident until people are middle aged or older.

As used herein, the term "atheroma," "atheromatous plaque region," "atherosclerotic plaque," or "atherosclerotic lesin" refers to an accumulation of degenerative material in the tunica intima (inner layer) of artery walls. The material consists of (mostly) macrophage cells, or debris, containing lipids (cholesterol and fatty acids), calcium and a variable amount of fibrous connective tissue. The accumulated material forms a swelling in the artery wall, which may intrude into the channel of the artery, narrowing it and restricting blood flow. Atheroma occurs in atherosclerosis.

As used herein, the term "liver X receptor" or "LXR" refers to a member of the nuclear receptor family of transcription factors and is closely related to nuclear receptors such as the PPARs, FXR and RXR. Liver X receptors (LXRs) are important regulators of cholesterol, fatty acid, and glucose homeostasis.

As used herein, the term "retinoid X receptors" or "RXR" refers to members of the nuclear receptor family of transcription factors and and are common binding partners to many other nuclear receptors, including PPARs, LXRs and FXR. RXR heterodimers act as ligand-dependent transcriptional regulators and increase the DNA-binding efficiency of its partner.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "drug" or "therapeutic agent" is meant to include any molecule, molecular complex or substance administered to an organism for diagnostic or therapeutic purposes, including medical imaging, monitoring, contraceptive, cosmetic, nutraceutical, pharmaceutical and prophylactic applications. The term "drug" is further meant to include any such molecule, molecular complex or substance that is chemically modified and/or operatively attached to a biologic or biocompatible structure.

As used herein, the term "solvent" refers to a medium in which a reaction is conducted. Solvents may be liquid but are not limited to liquid form. Solvent categories include but are not limited to nonpolar, polar, protic, and aprotic.

DETAILED DESCRIPTION OF THE INVENTION

Experiments conducted during the course of developing embodiments for the present invention demonstrated that sHDL nanoparticles selectively accumulate at specific vascular tissue regions (e.g., macrophages associated with atheromatous plaque regions), and improve the efficacy of therapeutic agents delivered to such vascular tissue regions with such sHDL nanoparticles. For example, increased sphingosine-1-phosphate (S1P) related nitric oxide release was demonstrated through its delivery within sHDL nanoparticices (see, Examples I and II). In addition, LXR agonist-encapsulated sHDL nanoparticles were shown to induce in vivo atherosclerosis regression while avoiding liver toxicity (e.g., hepatic steatosis) (Examples III and IV). In addition, LXR agonist-encapsulated sHDL nanoparticles and RXR agonist-encapsulated sHDL nanoparticles were shown to attenuate in vivo atherosclerosis development (Example VI).

Accordingly, the present invention relates to nanoparticles complexed with therapeutic agents configured for treating cardiovascular related disorders, and methods of synthesizing the same. In particular, the present invention is directed to compositions comprising synthetic HDL (sHDL) nanoparticles carrying therapeutic agents configured for treating cardiovascular related disorders, methods for synthesizing such sHDL nanoparticles, as well as systems and methods utilizing such sHDL nanoparticles (e.g., in diagnostic and/or therapeutic settings (e.g., for the delivery of therapeutic agents, imaging agents, and/or targeting agents (e.g., in cardiovascular disease diagnosis and/or therapy, etc.))).

The present invention is not limited to specific types or kinds of sHDL nanoparticles carrying a therapeutic agent (e.g., sHDL-TA nanoparticles). Generally, sHDL-TA nanoparticles are composed of a mixture of HDL apolipoprotein, an amphipathic lipid, and a therapeutic agent.

HDL apolipoproteins include, for example apolipoprotein A-I (apo apolipoprotein A-II (apo A-II), apolipoprotein A4 (apo A4), apolipoprotein Cs (apo Cs), and apolipoprotein E (apo E). Preferably, the carrier particles are composed of Apo A-I or Apo A-II, however the use of other lipoproteins including apolipoprotein A4, apolipoprotein Cs or apolipoprotein E may be used alone or in combination to formulate carrier particle mixtures for delivery of therapeutic agents. In some embodiments, the HDL apolipoprotein is selected from preproapoliprotein, preproApoA-I, proApoA-I, ApoA-I, preproApoA-II, proApoA-II, ApoA-II, preproApoA-1V, proApoA-1V, ApoA-IV, ApoA-V, preproApoE, proApoE, ApoE, preproApoA-1Milano, proApoA-IMilano ApoA-1Milano preproApoA-IParis , proApoA-IParis, and ApoA-IParis and peptide mimetics of these proteins mixtures thereof. In some embodiments, mimetics of such HDL apolipoproteins are used.

ApoA-I is synthesized by the liver and small intestine as preproapolipoprotein which is secreted as a proprotein that is rapidly cleaved to generate a mature polypeptide having 243 amino acid residues. ApoA-I consists mainly of 6 to 8 different 22 amino acid repeats spaced by a linker moiety which is often proline, and in some cases consists of a stretch made up of several residues. ApoA-I forms three types of stable complexes with lipids: small, lipid-poor complexes referred to as pre-beta-1 HDL; flattened discoidal particles containing polar lipids (phospholipid and cholesterol) referred to as pre-beta-2 HDL; and spherical particles containing both polar and nonpolar lipids, referred to as spherical or mature HDL ($HDL_3$ and $HDL_2$). Most HDL particles in the circulating population contain both ApoA-I and ApoA-II (the second major HDL protein). However, the fraction of HDL containing only ApoA-I (referred to herein as the AI-HDL fraction) is more effective in reverse cholesterol transport.

In some embodiments, ApoA-I agonists or mimetics are provided. In some embodiments, such ApoA-I mimetics are capable of forming amphipathic α-helices that mimic the activity of ApoA-I, and have specific activities approaching or exceeding that of the native molecule. In some, the ApoA-I mimetics are peptides or peptide analogues that: form amphipathic helices (in the presence of lipids), bind lipids, form pre-β-like or HDL-like complexes, activate lecithin:cholesterol acyltransferase (LCAT), increase serum levels of HDL fractions, and promote cholesterol efflux.

The present invention is not limited to use of a particular ApoA-I mimetic. In some embodiments, any of the ApoA-I mimetics described in Srinivasa, et al., 2014 Curr. Opinion Lipidology Vol. 25(4): 304-308 are utilized. In some embodiments, any of the ApoA-I mimetics described in U.S. Patent Application Publication Nos. 20110046056 and 20130231459 are utilized.

In some embodiments, the "22A" ApoA-I mimetic is used (PVLDLFRELLNELLEALKQKLK) (SEQ ID NO: 4) (see, Examples I-IV) (see, e.g., U.S. Pat. No. 7,566,695). In some embodiments, any of the following ApoA-I mimetics shown in Table 1 as described in U.S. Pat. No. 7,566,695 are utilized:

TABLE 1

ApoA-I mimetics

| SEQ ID NO | AMINO ACID SEQUENCE |
|---|---|
| (SEQ ID NO: 1) | PVLDLFRELLNELLEZLKQKLK |
| (SEQ ID NO: 2) | GVLDLFRELLNELLEALKQKLKK |
| (SEQ ID NO: 3) | PVLDLFRELLNELLEWLKQKLK |
| (SEQ ID NO: 4) | PVLDLFRELLNELLEALKQKLK |
| (SEQ ID NO: 5) | pVLDLFRELLNELLEALKQKLKK |
| (SEQ ID NO: 6) | PVLDLFRELLNEXLEALKQKLK |
| (SEQ ID NO: 7) | PVLDLFKELLNELLEALKQKLK |
| (SEQ ID NO: 8) | PVLDLFRELLNEGLEALKQKLK |
| (SEQ ID NO: 9) | PVLDLFRELGNELLEALKQKLK |
| (SEQ ID NO: 10) | PVLDLFRELLNELLEAZKQKLK |
| (SEQ ID NO: 11) | PVLDLFKELLQELLEALKQKLK |
| (SEQ ID NO: 12) | PVLDLFRELLNELLEAGKQKLK |
| (SEQ ID NO: 13) | GVLDLFRELLNEGLEALKQKLK |
| (SEQ ID NO: 14) | PVLDLFRELLNELLEALOQOLO |
| (SEQ ID NO: 15) | PVLDLFRELWNELLEALKQKLK |
| (SEQ ID NO: 16) | PVLDLRELLNELLEALKQKLK |
| (SEQ ID NO: 17) | PVLELFKELLQELLEALKQKLK |
| (SEQ ID NO: 18) | GVLDLFRELLNELLEALKQKLK |
| (SEQ ID NO: 19) | pVLDLFRELLNEGLEALKQKLK |
| (SEQ ID NO: 20) | PVLDLFREGLNELLEALKQKLK |
| (SEQ ID NO: 21) | pVLDLFRELLNELLEALKQKLK |
| (SEQ ID NO: 22) | PVLDLFRELLNELLEGLKQKLK |
| (SEQ ID NO: 23) | PLLELFKELLQELLEALKQKLK |
| (SEQ ID NO: 24) | PVLDLFRELLNELLEALQKKLK |
| (SEQ ID NO: 25) | PVLDFFRELLNEXLEALKQKLK |
| (SEQ ID NO: 26) | PVLDLFRELLNELLELLKQKLK |
| (SEQ ID NO: 27) | PVLDLFRELLNELZEALKQKLK |
| (SEQ ID NO: 28) | PVLDLFRELLNELWEALKQKLK |
| (SEQ ID NO: 29) | AVLDLFRELLNELLEALKQKLK |
| (SEQ ID NO: 30) | PVLDLPRELLNELLEALKQKLK[1] |
| (SEQ ID NO: 31) | PVLDLFLELLNEXLEALKQKLK |
| (SEQ ID NO: 32) | XVLDLFRELLNELLEALKQKLK |
| (SEQ ID NO: 33) | PVLDLFREKLNELLEALKQKLK |
| (SEQ ID NO: 34) | PVLDZFRELLNELLEALKQKLK |
| (SEQ ID NO: 35) | PVLDWFRELLNELLEALKQKLK |
| (SEQ ID NO: 36) | PLLELLKELLQELLEALKQKLK |
| (SEQ ID NO: 37) | PVLDLFREWLNELLEALKQKLK |
| (SEQ ID NO: 38) | PVLDLFRELLNEXLEAWKQKLK |
| (SEQ ID NO: 39) | PVLDLFRELLEELLKALKKKLK |
| (SEQ ID NO: 40) | PVLDLFNELLRELLEALQKKLK |
| (SEQ ID NO: 41) | PVLDLWRELLNEXLEALKQKLK |
| (SEQ ID NO: 42) | PVLDEFREKLNEXWEALKQKLK |
| (SEQ ID NO: 43) | PVLDEFREKLWEXLEALKQKLK |
| (SEQ ID NO: 44) | pvldefreklneXlealkqklk |
| (SEQ ID NO: 45) | PVLDEFREKLNEXLEALKQKLK |
| (SEQ ID NO: 46) | PVLDLFREKLNEXLEALKQKLK |
| (SEQ ID NO: 47) | ~VLDLFRELLNEGLEALKQKLK |
| (SEQ ID NO: 48) | pVLDLFRELLNELLEALKQKLK |
| (SEQ ID NO: 49) | PVLDLFRNLLEKLLEALEQKLK |
| (SEQ ID NO: 50) | PVLDLFRELLWEXLEALKQKLK |
| (SEQ ID NO: 51) | PVLDLFWELLNEXLEALKQKLK |
| (SEQ ID NO: 52) | PVWDEFREKLNEXLEALKQKLK |
| (SEQ ID NO: 53) | WLDLFRELLNELLEALKQKLK |
| (SEQ ID NO: 54) | PVLDLFRELLNEWLEALKQKLK |
| (SEQ ID NO: 55) | P~~~LFRELLNELLEALKQKLK |
| (SEQ ID NO: 56) | PVLDLFRELLNELLEALKQKKK |
| (SEQ ID NO: 57) | PVLDLFRNLLEELLKALEQKLK |
| (SEQ ID NO: 58) | PVLDEFREKLNEXLEALKQKL~ |
| (SEQ ID NO: 59) | LVLDLFRELLNELLEALKQKLK |
| (SEQ ID NO: 60) | PVLDLFRELLNELLEALKQ~~~ |
| (SEQ ID NO: 61) | PVLDEFRWKLNEXLEALKQKLK |
| (SEQ ID NO: 62) | PVLDEWREKLNEXLEALKQKLK |
| (SEQ ID NO: 63) | PVLDFFREKLNEXLEALKQKLK |
| (SEQ ID NO: 64) | PWLDEFREKLNEXLEALKQKLK |
| (SEQ ID NO: 65) | ~VLDEFREKLNEXLEALKQKLK |
| (SEQ ID NO: 66) | PVLDLFRNLLEELLEALQKKLK |
| (SEQ ID NO: 67) | ~VLDLFRELLNELLEALKQKLK |
| (SEQ ID NO: 68) | PVLDEFRELLKEXLEALKQKLK |
| (SEQ ID NO: 69) | PVLDEFRKKLNEXLEALKQKLK |
| (SEQ ID NO: 70) | PVLDEFRELLYEXLEALKQKLK |
| (SEQ ID NO: 71) | PVLDEFREKLNELXEALKQKLK |
| (SEQ ID NO: 72) | PVLDLFRELLNEXLWALKQKLK |
| (SEQ ID NO: 73) | PVLDEFWEKLNEXLEALKQKLK |
| (SEQ ID NO: 74) | PVLDKFREKLNEXLEALKQKLK |
| (SEQ ID NO: 75) | PVLDEFREKLNEELEALKQKLK |
| (SEQ ID NO: 76) | PVLDEFRELLFEXLEALKQKLK |

TABLE 1-continued

ApoA-I mimetics

| SEQ ID NO | AMINO ACID SEQUENCE |
|---|---|
| (SEQ ID NO: 77) | PVLDEFREKLNKXLEALKQKLK |
| (SEQ ID NO: 78) | PVLDEFRDKLNEXLEALKQKLK |
| (SEQ ID NO: 79) | PVLDEFRELLNELLEALKQKLK |
| (SEQ ID NO: 80) | PVLDLFERLLNELLEALQKKLK |
| (SEQ ID NO: 81) | PVLDEFREKLNWXLEALKQKLK |
| (SEQ ID NO: 82) | ~~LDEFREKLNEXLEALKQKLK |
| (SEQ ID NO: 83) | PVLDEFREKLNEXLEALWQKLK |
| (SEQ ID NO: 84) | PVLDEFREKLNELLEALKQKLK |
| (SEQ ID NO: 85) | P~LDLFRELLNELLEALKQKLK |
| (SEQ ID NO: 86) | PVLELFERLLDELLNALQKKLK |
| (SEQ ID NO: 87) | pllellkellqellealkqklk |
| (SEQ ID NO: 88) | PVLDKFRELLNEXLEALKQKLK |
| (SEQ ID NO: 89) | PVLDEFREKLNEXLWALKQKLK |
| (SEQ ID NO: 90) | ~~~DEFREKLNEXLEALKQKLK |
| (SEQ ID NO: 91) | PVLDEFRELLNEXLEALKQKLK |
| (SEQ ID NO: 92) | PVLDEFRELYNEXLEALKQKLK |
| (SEQ ID NO: 93) | PVLDEFREKLNEXLKALKQKLK |
| (SEQ ID NO: 94) | PVLDEFREKLNEALEALKQKLK |
| (SEQ ID NO: 95) | PVLDLFRELLNLXLEALKQKLK |
| (SEQ ID NO: 96) | pvldlfrellneXlealkqklk |
| (SEQ ID NO: 97) | PVLDLFRELLNELLE~~~~~~~ |
| (SEQ ID NO: 98) | PVLDLFRELLNEELEALKQKLK |
| (SEQ ID NO: 99) | KLKQKLAELLENLLERFLDLVP |
| (SEQ ID NO: 100) | pvldlfrellnellealkqklk |
| (SEQ ID NO: 101) | PVLDLFRELLNWXLEALKQKLK |
| (SEQ ID NO: 102) | PVLDLFRELLNLXLEALKEKLK |
| (SEQ ID NO: 103) | PVLDEFRELLNEELEALKQKLK |
| (SEQ ID NO: 104) | P~~~~~~~LLNELLEALKQKLK |
| (SEQ ID NO: 105) | PAADAFREAANEAAEAAKQKAK |
| (SEQ ID NO: 106) | PVLDLFREKLNEELEALKQKLK |
| (SEQ ID NO: 107) | klkqklaellenllerfldlvp |
| (SEQ ID NO: 108) | PVLDLFRWLLNEXLEALKQKLK |
| (SEQ ID NO: 109) | PVLDEFREKLNERLEALKQKLK |
| (SEQ ID NO: 110) | PVLDEFREKLNDOKEALKQKLK |
| (SEQ ID NO: 111) | PVLDEFREKLWEXWEALKQKLK |
| (SEQ ID NO: 112) | PVLDEFREKLNEXSEALKQKLK |
| (SEQ ID NO: 113) | PVLDEFREKLNEPLEALKQKLK |
| (SEQ ID NO: 114) | PVLDEFREKLNEXMEALKQKLK |
| (SEQ ID NO: 115) | PKLDEFREKLNEXLEALKQKLK |
| (SEQ ID NO: 116) | PHLDEFREKLNEXLEALKQKLK |
| (SEQ ID NO: 117) | PELDEFREKLNEXLEALKQKLK |
| (SEQ ID NO: 118) | PVLDEFREKLNEXLEALEQKLK |
| (SEQ ID NO: 119) | PVLDEFREKLNEELEAXKQKLK |
| (SEQ ID NO: 120) | PVLDEFREKLNEELEXLKQKLK |
| (SEQ ID NO: 121) | PVLDEFREKLNEELEALWQKLK |
| (SEQ ID NO: 122) | PVLDEFREKLNEELEWLKQKLK |
| (SEQ ID NO: 123) | QVLDLFRELLNELLEALKQKLK |
| (SEQ ID NO: 124) | PVLDLFOELLNELLEALOQOLO |
| (SEQ ID NO: 125) | NVLDLFRELLNELLEALKQKLK |
| (SEQ ID NO: 126) | PVLDLFRELLNELGEALKQKLK |
| (SEQ ID NO: 127) | PVLDLFRELLNELLELLKQKLK |
| (SEQ ID NO: 128) | PVLDLFRELLNELLEFLKQKLK |
| (SEQ ID NO: 129) | PVLELFNDLLRELLEALQKKLK |
| (SEQ ID NO: 130) | PVLELFNDLLRELLEALKQKLK |
| (SEQ ID NO: 131) | PVLELFKELLNELLDALRQKLK |
| (SEQ ID NO: 132) | PVLDLFRELLENLLEALQKKLK |
| (SEQ ID NO: 133) | PVLELFERLLEDLLQALNKKLK |
| (SEQ ID NO: 134) | PVLELFERLLEDLLKALNOKLK |
| (SEQ ID NO: 135) | DVLDLFRELLNELLEALKQKLK |
| (SEQ ID NO: 136) | PALELFKDLLQELLEALKQKLK |
| (SEQ ID NO: 137) | PVLDLFRELLNEGLEAZKQKLK |
| (SEQ ID NO: 138) | PVLDLFRELLNEGLEWLKQKLK |
| (SEQ ID NO: 139) | PVLDLFRELWNEGLEALKQKLK |
| (SEQ ID NO: 140) | PVLDLFRELLNEGLEALOQOLO |
| (SEQ ID NO: 141) | PVLDFFRELLNEGLEALKQKLK |
| (SEQ ID NO: 142) | PVLELFRELLNEGLEALKQKLK |
| (SEQ ID NO: 143) | PVLDLFRELLNEGLEALKQKLK* |
| (SEQ ID NO: 144) | pVLELFENLLERLLDALQKKLK |
| (SEQ ID NO: 145) | GVLELFENLLERLLDALQKKLK |
| (SEQ ID NO: 146) | PVLELFENLLERLLDALQKKLK |
| (SEQ ID NO: 147) | PVLELFENLLERLFDALQKKLK |
| (SEQ ID NO: 148) | PVLELFENLLERLGDALQKKLK |
| (SEQ ID NO: 149) | PVLELFENLWERLLDALQKKLK |
| (SEQ ID NO: 150) | PLLELFENLLERLLDALQKKLK |
| (SEQ ID NO: 151) | PVLELFENLGERLLDALQKKLK |
| (SEQ ID NO: 152) | PVFELFENLLERLLDALQKKLK |

TABLE 1-continued

ApoA-I mimetics

| SEQ ID NO | AMINO ACID SEQUENCE |
|---|---|
| (SEQ ID NO: 153) | AVLELFENLLERLLDALQKKLK |
| (SEQ ID NO: 154) | PVLELFENLLERGLDALQKKLK |
| (SEQ ID NO: 155) | PVLELFLNLWERLLDALQKKLK |
| (SEQ ID NO: 156) | PVLELFLNLLERLLDALQKKLK |
| (SEQ ID NO: 157) | PVLEFFENLLERLLDALQKKLK |
| (SEQ ID NO: 158) | PVLELFLNLLERLLDWLQKKLK |
| (SEQ ID NO: 159) | PVLDLFENLLERLLDALQKKLK |
| (SEQ ID NO: 160) | PVLELFENLLERLLDWLQKKLK |
| (SEQ ID NO: 161) | PVLELFENLLERLLEALQKKLK |
| (SEQ ID NO: 162) | PVLELFENWLERLLDALQKKLK |
| (SEQ ID NO: 163) | PVLELFENLLERLWDALQKKLK |
| (SEQ ID NO: 164) | PVLELFENLLERLLDAWQKKLK |
| (SEQ ID NO: 165) | PVLELFENLLERLLDLLQKKLK |
| (SEQ ID NO: 166) | PVLELFLNLLEKLLDALQKKLK |
| (SEQ ID NO: 167) | PVLELFENGLERLLDALQKKLK |
| (SEQ ID NO: 168) | PVLELFEQLLEKLLDALQKKLK |
| (SEQ ID NO: 169) | PVLELFENLLEKLLDALQKKLK |
| (SEQ ID NO: 170) | PVLELFENLLEOLLDALQOOLO |
| (SEQ ID NO: 171) | PVLELFENLLEKLLDLLQKKLK |
| (SEQ ID NO: 172) | PVLELFLNLLERLGDALQKKLK |
| (SEQ ID NO: 173) | PVLDLFDNLLDRLLDLLNKKLK |
| (SEQ ID NO: 174) | pvlelfenllerlldalqkklk |
| (SEQ ID NO: 175) | PVLELFENLLERLLELLNKKLK |
| (SEQ ID NO: 176) | PVLELWENLLERLLDALQKKLK |
| (SEQ ID NO: 177) | GVLELFLNLLERLLDALQKKLK |
| (SEQ ID NO: 178) | PVLELFDNLLEKLLEALQKKLR |
| (SEQ ID NO: 179) | PVLELFDNLLERLLDALQKKLK |
| (SEQ ID NO: 180) | PVLELFDNLLDKLLDALQKKLR |
| (SEQ ID NO: 181) | PVLELFENLLERWLDALQKKLK |
| (SEQ ID NO: 182) | PVLELFENLLEKLLEALQKKLK |
| (SEQ ID NO: 183) | PLLELFENLLEKLLDALQKKLK |
| (SEQ ID NO: 184) | PVLELFLNLLERLLDAWQKKLK |
| (SEQ ID NO: 185) | PVLELFENLLERLLDALQOOLO |
| (SEQ ID NO: 186) | PVLELFEQLLERLLDALQKKLK |
| (SEQ ID NO: 187) | PVLELFENLLERLLDALNKKLK |
| (SEQ ID NO: 188) | PVLELFENLLDRLLDALQKKLK |
| (SEQ ID NO: 189) | DVLELFENLLERLLDALQKKLK |
| (SEQ ID NO: 190) | PVLEFWDNLLDKLLDALQKKLR |
| (SEQ ID NO: 191) | PVLDLLRELLEELKQKLK* |
| (SEQ ID NO: 192) | PVLDLFKELLEELKQKLK* |
| (SEQ ID NO: 193) | PVLDLFRELLEELKQKLK* |
| (SEQ ID NO: 194) | PVLELFRELLEELKQKLK* |
| (SEQ ID NO: 195) | PVLELFKELLEELKQKLK* |
| (SEQ ID NO: 196) | PVLDLFRELLEELKNKLK* |
| (SEQ ID NO: 197) | PLLDLFRELLEELKQKLK* |
| (SEQ ID NO: 198) | GVLDLFRELLEELKQKLK* |
| (SEQ ID NO: 199) | PVLDLFRELWEELKQKLK* |
| (SEQ ID NO: 200) | NVLDLFRELLEELKQKLK* |
| (SEQ ID NO: 201) | PLLDLFKELLEELKQKLK* |
| (SEQ ID NO: 202) | PALELFKDLLEELRQKLR* |
| (SEQ ID NO: 203) | AVLDLFRELLEELKQKLK* |
| (SEQ ID NO: 204) | PVLDFFRELLEELKQKLK* |
| (SEQ ID NO: 205) | PVLDLFREWLEELKQKLK* |
| (SEQ ID NO: 206) | PLLELLKELLEELKQKLK* |
| (SEQ ID NO: 207) | PVLELLKELLEELKQKLK* |
| (SEQ ID NO: 208) | PALELFKDLLEELRQRLK* |
| (SEQ ID NO: 209) | PVLDLFRELLNELLQKLK |
| (SEQ ID NO: 210) | PVLDLFRELLEELKQKLK |
| (SEQ ID NO: 211) | PVLDLFRELLEELOQOLO* |
| (SEQ ID NO: 212) | PVLDLFOELLEELOQOLK* |
| (SEQ ID NO: 213) | PALELFKDLLEEFRQRLK* |
| (SEQ ID NO: 214) | pVLDLFRELLEELKQKLK* |
| (SEQ ID NO: 215) | PVLDLFRELLEEWKQKLK* |
| (SEQ ID NO: 216) | PVLELFKELLEELKQKLK |
| (SEQ ID NO: 217) | PVLDLFRELLELLKQKLK |
| (SEQ ID NO: 218) | PVLDLFRELLNELLQKLK* |
| (SEQ ID NO: 219) | PVLDLFRELLNELWQKLK |
| (SEQ ID NO: 220) | PVLDLFRELLEELQKKLK |
| (SEQ ID NO: 221) | DVLDLFRELLEELKQKLK* |
| (SEQ ID NO: 222) | PVLDAFRELLEALLQLKK |
| (SEQ ID NO: 223) | PVLDAFRELLEALAQLKK |
| (SEQ ID NO: 224) | PVLDLFREGWEELKQKLK |
| (SEQ ID NO: 225) | PVLDAFRELAEALAQLKK |
| (SEQ ID NO: 226) | PVLDAFRELGEALLQLKK |
| (SEQ ID NO: 227) | PVLDLFRELGEELKQKLK* |
| (SEQ ID NO: 228) | PVLDLFREGLEELKQKLK* |

TABLE 1-continued

ApoA-I mimetics

| SEQ ID NO | AMINO ACID SEQUENCE |
|---|---|
| (SEQ ID NO: 229) | PVLDLFRELLEEGKQKLK* |
| (SEQ ID NO: 230) | PVLELFERLLEDLQKKLK |
| (SEQ ID NO: 231) | PVLDLFRELLEKLEQKLK |
| (SEQ ID NO: 232) | PLLELFKELLEELKQKLK* |
| (SEQ ID NO: 233) | LDDLLQKWAEAFNQLLKK |
| (SEQ ID NO: 234) | EWLKAFYEKVLEKLKELF* |
| (SEQ ID NO: 235) | EWLEAFYKKVLEKLKELF* |
| (SEQ ID NO: 236) | DWLKAFYDKVAEKLKEAF* |
| (SEQ ID NO: 237) | DWFKAFYDKVFEKFKEFF |
| (SEQ ID NO: 238) | GIKKFLGSIWKFIKAFVG |
| (SEQ ID NO: 239) | DWFKAFYDKVAEKFKEAF |
| (SEQ ID NO: 240) | DWLKAFYDKVAEKLKEAF |
| (SEQ ID NO: 241) | DWLKAFYDKVFEKFKEFF |
| (SEQ ID NO: 242) | EWLEAFYKKVLEKLKELP |
| (SEQ ID NO: 243) | DWFKAFYDKFFEKFKEFF |
| (SEQ ID NO: 244) | EWLKAFYEKVLEKLKELF |
| (SEQ ID NO: 245) | EWLKAEYEKVEEKLKELF* |
| (SEQ ID NO: 246) | EWLKAEYEKVLEKLKELF* |
| (SEQ ID NO: 247) | EWLKAFYKKVLEKLKELF* |
| (SEQ ID NO: 248) | PVLDLFRELLEQKLK* |
| (SEQ ID NO: 249) | PVLDLFRELLEELKQK* |
| (SEQ ID NO: 250) | PVLDLFRELLEKLKQK* |
| (SEQ ID NO: 251) | PVLDLFRELLEKLQK* |
| (SEQ ID NO: 252) | PVLDLFRELLEALKQK* |
| (SEQ ID NO: 253) | PVLDLFENLLERLKQK* |
| (SEQ ID NO: 254) | PVLDLFRELLNELKQK* |

*indicates peptides that are N-terminal acetylated and C-terminal amidated; indicates peptides that are N-terminal dansylated, sp indicates peptides that exhibited solubility problems under the experimental conditions; X is Aib, Z is Nal; O is Orn, He (%) designates percent helicity, mics designates micelles; and - indicates deleted amino acids.

In some embodiments, an ApoA-I mimetic having the following sequence as described in U.S. Pat. No. 6,743,778 is utilized: Asp Trp Leu Lys Ala Phe Tyr Asp Lys Val Ala Glu Lys Leu Lys Glu Ala Phe (SEQ ID NO: 256).

In some embodiments, any of the following ApoA-I mimetics shown in Table 2 as described in U.S. Patent Application Publication No. 2003/0171277 are utilized:

| | |
|---|---|
| (SEQ ID NO: 256) | D-W-L-K-A-F-Y-D-K-V-A-E-K-L-K-E-A-F |
| (SEQ ID NO: 257) | Ac-D-W-L-K-A-F-Y-D-K-V-A-E-K-L-K-E-A-F-NH$_2$ |
| (SEQ ID NO: 258) | Ac-D-W-F-K-A-F-Y-D-K-V-A-E-K-L-K-E-A-F-NH$_2$ |
| (SEQ ID NO: 259) | Ac-D-W-L-K-A-F-Y-D-K-V-A-E-K-F-K-E-A-F-NH$_2$ |
| (SEQ ID NO: 260) | Ac-D-W-F-K-A-F-Y-D-K-V-A-E-K-L-K-E-A-F-NH$_2$ |
| (SEQ ID NO: 261) | Ac-D-W-L-K-A-F-Y-D-K-V-F-E-K-L-K-E-F-F-NH$_2$ |
| (SEQ ID NO: 262) | Ac-D-W-L-K-A-F-Y-D-K-F-F-E-K-F-K-E-F-F-NH$_2$ |
| (SEQ ID NO: 263) | Ac-D-W-F-K-A-F-Y-D-K-F-F-E-K-F-K-E-F-F-NH$_2$ |
| (SEQ ID NO: 264) | Ac-D-W-L-K-A-F-Y-D-K-V-A-E-K-L-K-E-F-F-NH$_2$ |
| (SEQ ID NO: 265) | Ac-D-W-L-K-A-F-Y-D-K-V-F-E-K-F-K-E-A-F-NH$_2$ |
| (SEQ ID NO: 266) | Ac-D-W-L-K-A-F-Y-D-K-V-F-E-K-L-K-E-F-F-NH$_2$ |
| (SEQ ID NO: 267) | Ac-D-W-L-K-A-F-Y-D-K-V-A-E-K-F-K-E-F-F-NH$_2$ |
| (SEQ ID NO: 268) | Ac-D-W-L-K-A-F-Y-D-K-V-F-E-K-F-K-E-F-F-NH$_2$ |
| (SEQ ID NO: 269) | Ac-E-W-L-K-L-F-Y-E-K-V-L-E-K-F-K-E-A-F-NH$_2$ |
| (SEQ ID NO: 270) | Ac-E-W-L-K-A-F-Y-D-K-V-A-E-K-F-K-E-A-F-NH$_2$ |
| (SEQ ID NO: 271) | Ac-E-W-L-K-A-F-Y-D-K-V-A-E-K-L-K-E-F-F-NH$_2$ |
| (SEQ ID NO: 272) | Ac-E-W-L-K-A-F-Y-D-K-V-F-E-K-F-K-E-A-F-NH$_2$ |
| (SEQ ID NO: 273) | Ac-E-W-L-K-A-F-Y-D-K-V-F-E-K-L-K-E-F-F-NH$_2$ |
| (SEQ ID NO: 274) | Ac-E-W-L-K-A-F-Y-D-K-V-A-E-K-F-K-E-F-F-NH$_2$ |
| (SEQ ID NO: 275) | Ac-E-W-L-K-A-F-Y-D-K-V-F-E-K-F-K-E-F-F-NH$_2$ |

| | |
|---|---|
| (SEQ ID NO: 276) | Ac-A-F-Y-D-K-V-A-E-K-L-K-E-A-F-NH$_2$ |
| (SEQ ID NO: 277) | Ac-A-F-Y-D-K-V-A-E-K-F-K-E-A-F-NH$_2$ |
| (SEQ ID NO: 278) | Ac-A-F-Y-D-K-V-A-E-K-L-K-E-A-F-NH$_2$ |
| (SEQ ID NO: 279) | Ac-A-F-Y-D-K-F-F-E-K-F-K-E-F-F-NH$_2$ |
| (SEQ ID NO: 280) | Ac-A-F-Y-D-K-F-F-E-K-F-K-E-F-F-NH$_2$ |
| (SEQ ID NO: 281) | Ac-A-F-Y-D-K-V-A-E-K-F-K-E-A-F-NH$_2$ |
| (SEQ ID NO: 282) | Ac-A-F-Y-D-K-V-A-E-K-L-K-E-F-F-NH$_2$ |
| (SEQ ID NO: 283) | Ac-A-F-Y-D-K-V-F-E-K-F-K-E-A-F-NH$_2$ |
| (SEQ ID NO: 284) | Ac-A-F-Y-D-K-V-F-E-K-L-K-E-F-F-NH$_2$ |
| (SEQ ID NO: 285) | Ac-A-F-Y-D-K-V-A-E-K-F-K-E-F-F-NH$_2$ |
| (SEQ ID NO: 286) | Ac-K-A-F-Y-D-K-V-F-E-K-F-K-E-F-NH$_2$ |
| (SEQ ID NO: 287) | Ac-L-F-Y-E-K-V-L-E-K-F-K-E-A-F-NH$_2$ |
| (SEQ ID NO: 288) | Ac-A-F-Y-D-K-V-A-E-K-F-K-E-A-F-NH$_2$ |
| (SEQ ID NO: 289) | Ac-A-F-Y-D-K-V-A-E-K-L-K-E-F-F-NH$_2$ |
| (SEQ ID NO: 290) | Ac-A-F-Y-D-K-V-F-E-K-F-K-E-A-F-NH$_2$ |
| (SEQ ID NO: 291) | Ac-A-F-Y-D-K-V-F-E-K-L-K-E-F-F-NH$_2$ |
| (SEQ ID NO: 292) | Ac-A-F-Y-D-K-V-A-E-K-F-K-E-F-F-NH$_2$ |
| (SEQ ID NO: 293) | Ac-A-F-Y-D-K-V-F-E-K-F-K-E-F-F-NH$_2$ |
| (SEQ ID NO: 294) | Ac-D-W-L-K-A-L-Y-D-K-V-A-E-K-L-K-E-A-L-NH$_2$ |
| (SEQ ID NO: 295) | Ac-D-W-F-K-A-F-Y-E-K-V-A-E-K-L-K-E-F-F-NH$_2$ |
| (SEQ ID NO: 296) | Ac-D-W-F-K-A-F-Y-E-K-F-F-E-K-F-K-E-F-F-NH$_2$ |
| (SEQ ID NO: 297) | Ac-E-W-L-K-A-L-Y-E-K-V-A-E-K-L-K-E-A-L-NH$_2$ |
| (SEQ ID NO: 298) | Ac-E-W-L-K-A-F-Y-E-K-V-A-E-K-L-K-E-A-F-NH$_2$ |
| (SEQ ID NO: 299) | Ac-E-W-F-K-A-F-Y-E-K-V-A-E-K-L-K-E-F-F-NH$_2$ |
| (SEQ ID NO: 300) | Ac-E-W-L-K-A-F-Y-E-K-V-F-E-K-F-K-E-F-F-NH$_2$ |
| (SEQ ID NO: 301) | Ac-E-W-L-K-A-F-Y-E-K-F-F-E-K-F-K-E-F-F-NH$_2$ |
| (SEQ ID NO: 302) | Ac-E-W-F-K-A-F-Y-E-K-F-F-E-K-F-K-E-F-F-NH$_2$ |
| (SEQ ID NO: 303) | Ac-D-F-L-K-A-W-Y-D-K-V-A-E-K-L-K-E-A-W-NH$_2$ |
| (SEQ ID NO: 304) | Ac-E-F-L-K-A-W-Y-E-K-V-A-E-K-L-K-E-A-W-NH$_2$ |
| (SEQ ID NO: 305) | Ac-D-F-W-K-A-W-Y-D-K-V-A-E-K-L-K-E-W-W-NH$_2$ |
| (SEQ ID NO: 306) | Ac-E-F-W-K-A-W-Y-E-K-V-A-E-K-L-K-E-W-W-NH$_2$ |
| (SEQ ID NO: 307) | Ac-D-K-L-K-A-F-Y-D-K-V-F-E-W-A-K-E-A-F-NH$_2$ |
| (SEQ ID NO: 308) | Ac-D-K-W-K-A-V-Y-D-K-F-A-E-A-F-K-E-F-L-NH$_2$ |
| (SEQ ID NO: 309) | Ac-E-K-L-K-A-F-Y-E-K-V-F-E-W-A-K-E-A-F-NH$_2$ |
| (SEQ ID NO: 310) | Ac-E-K-W-K-A-V-Y-E-K-F-A-E-A-F-K-E-F-L-NH$_2$ |
| (SEQ ID NO: 311) | Ac-D-W-L-K-A-F-V-D-K-F-A-E-K-F-K-E-A-Y-NH$_2$ |
| (SEQ ID NO: 312) | Ac-E-K-W-K-A-V-Y-E-K-F-A-E-A-F-K-E-F-L-NH$_2$ |
| (SEQ ID NO: 313) | Ac-D-W-L-K-A-F-V-Y-D-K-V-F-K-L-K-E-F-F-NH$_2$ |
| (SEQ ID NO: 314) | Ac-E-W-L-K-A-F-V-Y-E-K-V-F-K-L-K-E-F-F-NH$_2$ |
| (SEQ ID NO: 315) | Ac-D-W-L-R-A-F-Y-D-K-V-A-E-K-L-K-E-A-F-NH$_2$ |

```
(SEQ ID NO: 316)    Ac-E-W-L-R-A-F-Y-E-K-V-A-E-K-L-K-E-A-F-NH2

(SEQ ID NO: 317)    Ac-D-W-L-K-A-F-Y-D-R-V-A-E-K-L-K-E-A-F-NH2

(SEQ ID NO: 318)    Ac-E-W-L-K-A-F-Y-E-R-V-A-E-K-L-K-E-A-F-NH2

(SEQ ID NO: 319)    Ac-D-W-L-K-A-F-Y-D-K-V-A-E-R-L-K-E-A-F-NH2

(SEQ ID NO: 320)    Ac-E-W-L-K-A-F-Y-E-K-V-A-E-R-L-K-E-A-F-NH2

(SEQ ID NO: 321)    Ac-D-W-L-K-A-F-Y-D-K-V-A-E-K-L-R-E-A-F-NH2

(SEQ ID NO: 322)    Ac-E-W-L-K-A-F-Y-E-K-V-A-E-K-L-R-E-A-F-NH2

(SEQ ID NO: 323)    Ac-D-W-L-K-A-F-Y-D-R-V-A-E-R-L-K-E-A-F-NH2

(SEQ ID NO: 324)    Ac-E-W-L-K-A-F-Y-E-R-V-A-E-R-L-K-E-A-F-NH2

(SEQ ID NO: 325)    Ac-D-W-L-R-A-F-Y-D-K-V-A-E-K-L-R-E-A-F-NH2

(SEQ ID NO: 326)    Ac-E-W-L-R-A-F-Y-E-K-V-A-E-K-L-R-E-A-F-NH2

(SEQ ID NO: 327)    Ac-D-W-L-R-A-F-Y-D-R-V-A-E-K-L-K-E-A-F-NH2

(SEQ ID NO: 328)    Ac-E-W-L-R-A-F-Y-E-R-V-A-E-K-L-K-E-A-F-NH2

(SEQ ID NO: 329)    Ac-D-W-L-K-A-F-Y-D-K-V-A-E-R-L-R-E-A-F-NH2

(SEQ ID NO: 330)    Ac-E-W-L-K-A-F-Y-E-K-V-A-E-R-L-R-E-A-F-NH2

(SEQ ID NO: 331)    Ac-D-W-L-R-A-F-Y-D-K-V-A-E-R-L-K-E-A-F-NH2

(SEQ ID NO: 332)    Ac-E-W-L-R-A-F-Y-E-K-V-A-E-R-L-K-E-A-F-NH2
```

In some embodiments, an ApoA-I mimetic having the following sequence as described in U.S. Patent Application Publication No. 2006/0069030 is utilized:

```
                                        (SEQ ID NO: 333)
F-A-E-K-F-K-E-A-V-K-D-Y-F-A-K-F-W-D.
```

In some embodiments, an ApoA-I mimetic having the following sequence as described in U.S. Patent Application Publication No. 2009/0081293 is utilized:

```
                        (SEQ ID NO: 334)
DWFKAFYDKVAEKFKEAF;

(SEQ ID NO: 335)
DWLKAFYDKVAEKLKEAF;

(SEQ ID NO: 336)
PALEDLRQGLLPVLESFKVFLSALEEYTKKLNTQ.
```

Amphipathic lipids include, for example, any lipid molecule which has both a hydrophobic and a hydrophilic moiety. Examples include phospholipids or glycolipids. Examples of phospholipids which may be used in the sHDL-TA nanoparticles include but are not limited to dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl) butyramide], 1,2-dihexadecanoyl-sn-glycero-3-phosphoethanolamine-N-[4-(p-maleimidophenyl) butyramide], 1,2-dihexadecanoyl-sn-glycero-3-phosphoethanolamine-N-[4-(p-maleimidomethyl) butyramide], 1,2-di-(9Z-octadecenoyl)-sn-glycero-3-phosphoethanolamine-N-[4-(p-maleimidomethyl) cyclohexane-carboxamide], phosphatidylcholine, phosphatidylinositol, phosphatidylserine, phosphatidylethanolamine, and combinations thereof.

In some embodiments, exemplary phospholipids include, but are not limited to, small alkyl chain phospholipids, egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, phosphatidylglycerols, diphosphatidylglycerols such as dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, egg sphingomyelin, milk sphingomyelin, palmitoyl sphingomyelin, phytosphingomyelin, dipalmitoylsphingomyelin, distearoylsphingomyelin, dipalmitoylphosphatidylglycerol salt, phosphatidic acid, galactocerebroside, gangliosides, cerebrosides, dilaurylphosphatidylcholine, (1,3)-D-mannosyl-(1,3)diglyceride, aminophenylglycoside, 3-cholesteryl-6'-(glycosylthio)hexyl ether glycolipids, and cholesterol and its derivatives. Phospholipid fractions including SM and palmitoylsphingomyelin can optionally include small quantities of any type of lipid, including but not limited to lysophospholipids, sphingomyelins other than palmitoylsphingomyelin, galactocerebroside, gangliosides, cerebrosides, glycerides, triglycerides, and cholesterol and its derivatives.

In some embodiments, the sHDL nanoparticles have a molar ratio of phospholipid/

Attorney HDL apolipoprotein from 2 to 250 (e.g., 10 to 200, 20 to 100, 20 to 50, 30 to 40).

Therapeutic agents include drugs and/or medicaments known to be useful in treating and/or preventing cardiovascular related disorders (e.g., atherosclerosis, heart failure, arrhythmia, atrial fibrillation, hypertension, coronary artery disease, angina pectoris, etc.). Examples of therapeutic agents known to be useful in treating and/or preventing cardiovascular related disorders include, angiotensin-converting enzyme (ACE) inhibitors (e.g., benazepril, enalapril, Lisinopril, perindopril, Ramipril), adenosine, alpha blockers (alpha adrenergic antagonist medications) (e.g., clonidine, guanabenz, labetalol, phenoxybenzamine, terazosin, doxazosin, guanfacine, methyldopa, prazosin), angtiotensin II receptor blockers (ARBs) (e.g., candesartan, irbesartan, olmesartan medoxomil, telmisartan, eprosartan, losartan, tasosartan, valsartan), antiocoagulants (e.g., heparin fondaparinux, warfarin, ardeparin, enoxaparin, reviparin, dalteparin, nadroparin, tinzaparin), antiplatelet agents (e.g., abciximab, clopidogrel, eptifibatide, ticlopidine, cilostazol, dipyridamole, sulfinpyrazone, tirofiban), beta blockers (e.g., acebutolol, betaxolol, carteolol, metoprolol, penbutolol, propranolol, atenolol, bisoprolol, esmolol, nadolol, pindolol, timolol), calcium channel blockers (e.g., amlopidine, felodipine, isradipine, nifedipine, verapamil, diltiazem, nicardipine, nimodipine, nisoldipine), diuretics, aldosterone blockers, loop diuretics (e.g., bumetanide, furosemide, ethacrynic acid, torsemide), potassium-sparing diuretics, thiazide diuretics (e.g., chlorothiazide, chlorthalidone, hydrochlorothiazide, hydroflumethiazide, methyclothiazide, metolazone, polythiazide, quinethazone, trichlormethiazide), inoptropics, bile acid sequestrants (e.g., cholestyramine, coletipol, colesevelam), fibrates (e.g., clofibrate, gemfibrozil, fenofibrate), statins (e.g., atorvastatinm, lovastatin, simvastatin, fluvastatin, pravastatin), selective cholesterol absorption inhibitors (e.g., ezetimibe), potassium channel blockers (e.g., amidarone, ibutilide, dofetilide), sodium channel blockers (e.g., disopyramide, mexiletine, procainamide, quinidine, flecainide, moricizine, propafenone), thrombolytic agents (e.g., alteplase, reteplase, tenecteplase, anistreplase, streptokinase, urokinase), vasoconstrictors, vasodilators (e.g., hydralazine, minoxidil, mecamylamine, isorbide dintrate, isorbide mononitrate, nitroglycerin), cholesteryl ester transfer protein inhibitors (e.g., anacetrapib, evacetrapib), PPAR agonists (e.g., K-877, CER-002, DSP-8658, INT131, GFT505), and apoA-I activators (e.g., RVX-208).

In some embodiments, the therapeutic agent is sphingosine-1-phosphate (S1P) (see, Examples I and II). In some embodiments, the therapeutic agent is a SP receptor agonist. In some embodiments, the therapeutic agent is a SW analogue.

In some embodiments, the retinoid X receptor agonist is selected from Bexarotene, CD3254, Docosahexaenoic acid, fluorobexarotene, isotretinoin, retinoic acid, SR11237, fenretinide, HX630, liarozole dihydrochloride, LG100754 and LG101506.

In some embodiments, the combined LXR and RXR agonists are selected from TO901317, ATI-111, LXR-623, XL-652, hypocholamide, GW3965, N,N-dimethyl-3beta-hydroxy-cholenamide (DMHCA), 22(R)-hydroxycholesterol, 24(S)-hydroxycholesterol, (−)anthrabenzoxocinone, (−)bischloroanthrabenzoxocinone ((−)-BABX), Bexarotene, CD3254, Docosahexaenoic acid, fluorobexarotene, isotretinoin, retinoic acid, SR11237, fenretinide, HX630, liarozole dihydrochloride, LG100754 and LG101506.

In some embodiments, the therapeutic agent is a liver X receptor (LXR) agonist (see, Examples III and IV). Generally, during the development of atherosclerosis, cholesterol deposited in macrophages at sites of atherosclerotic plaques (e.g., atheromatous plaque regions) converts the macrophages into foam cells, which account for the major fraction of lesion deposited cholesterol (see, e.g., Tangirala, R. K.; et al., Proceedings of the National Academy of Sciences of the United States of America 2002, 99 (18), 11896-11901; Rader, D. J.; et al., Cell Metabolism 2005, 1 (4), 223-230; Witztum, J. L.; et al., Journal of Clinical Investigation 1991, 88 (6), 1785-1792). In addition, macrophages produce proteolytic enzymes that can digest extracellular matrix, leading to plaque rupture, resulting in the recruitment of inflammatory cells (see, e.g., Libby, P.; et al., Nature 2011, 473 (7347), 317-325; Vanderwal, A. C.; et al., Circulation 1994, 89 (1), 36-44; Weber, C.; et al., Nature Medicine 2011, 17 (11), 1410-1422). Therefore, both promoting reverse cholesterol transport (RCT) and inhibiting inflammation at the plaque area have been widely pursued as therapeutic strategies for atherosclerosis. Recently, LXR agonists have been found to inhibit the atherosclerosis by reversing the above two pathological processes (see, e.g., Im, S. S.; et al., Circulation Research 2011, 108 (8), 996-1001). Specifically, LXR agonists can up-regulate ABCA1/ABCG1 transporters on macrophages and remove cholesterol from macrophages by reverse cholesterol transport (see, e.g., Briand, F.; et al., Journal of Lipid Research 2010, 51 (4), 763-770; Cuchel, M.; et al., Circulation 2006, 113 (21), 2548-2555), which reduces the lesion cholesterol content directly and prevents the conversion of macrophages into foam cells at sites of atherosclerotic lesions (see, e.g., Tangirala, R. K.; et al., Proceedings of the National Academy of Sciences of the United States of America 2002, 99 (18), 11896-11901). In addition, LXR agonists have been reported to attenuate the inflammatory response through a series of signaling cascades (see, e.g., Ghisletti, S.; et al., Genes & Development 2009, 23 (6), 681-693; Ghisletti, S.; Huang, W.; Ogawa, S.; Pascual, G.; Lin, M. E.; Willson, T. M.; Rosenfeld, M. G.; et al., Molecular Cell 2007, 25 (1), 57-70), which can also contribute to atherosclerosis inhibition (see, e.g., Joseph, S. B.; et al., Nature Medicine 2003, 9 (2), 213-219). However, treatment of experimental atherosclerotic mice with LXR agonists leads to liver toxicity, owing to unrestrained lipogenesis (see, e.g., Repa, J. J.; et al., Genes & Development 2000, 14 (22), 2819-2830; Schultz, J. R.; et al., Genes & Development 2000, 14 (22), 2831-2838). The present invention overcomes such limitations through encapsulation of the LXR agonist within a sHDL nanoparticle thereby ensuring efficient targeting of the drug to the desired atheromatous plaque regions while avoiding liver toxicity side effects.

Previously, high-density lipoproteins (HDLs) have been used for atherosclerotic plaque imaging and delivery of several different therapeutic molecules to the plaque (see, e.g., Skajaa, T.; et al., Biomaterials 2011, 32 (1), 206-213; Cormode, D. P.; et al., Nano Letters 2008, 8 (11), 3715-3723; Luthi, A. J.; et al., Acs Nano 2012, 6 (1), 276-285). HDL is able to target the plaque through two main mechanisms (see, e.g., Kingwell, B. A.; et al., Nat Rev Drug Discov 2014, 13 (6), 445-64). Firstly, the vasculature around atherosclerosis lesions becomes leaky due severe inflammation and endothelial injury, which would facilitate the infiltration of HDL into the vascular tissue (see, e.g., Moulton, K. S.; et al., Circulation 2004, 110 (10), 1330-1336; Zhang, W. L.; et al., International Journal of Pharmaceutics 2011, 419 (1-2), 314-321). Secondly, HDL can be retained in the plaque through ingestion by macrophages and macrophage-derived foam cells, mediated by the SR-BI receptor, ABCA1 and ABCG1 receptors expressed on macrophage surfaces (see, e.g., Rader, D. J., et al., Journal of Clinical Investigation 2006, 116 (12), 3090-3100; Tall, A. R.; et al., Cell Metabolism 2008, 7 (5), 365-375). In addition to the proven safety of HDL in previous clinical trials, the above properties of HDL indicate HDL as an efficient delivery vehicle for LXR agonists to the plaque while minimizing severe side effects (e.g., liver toxicity side effects (e.g., hepatic steatosis)).

As described in Example III, experiments conducted during the course of developing embodiments for the present invention utilized synthetic HDL composed of ApoAl mimetic peptide and lipids to deliver LXR agonists to atherosclerotic plaques.

The present invention is not limited to the use of particular LXR agonists. In some embodiments, the LXR agonist is TO901317. Additional examples of LXR agonist include, but are not limited to, TO901317, ATI-111, LXR-623, XL-652, hypocholamide, GW3965, N,N-dimethyl-3beta-hydroxy-cholenamide (DMHCA), 22(R)-hydroxycholesterol, 24(S)-hydroxycholesterol, (−)anthrabenzoxocinone and (−)bischloroanthrabenzoxocinone ((−)-BABX)).

The present invention is not limited to the use of particular RXR agonists. In some embodiments, the RXR agonist is CD3254. Additional examples of RXR agonist include, but are not limited to, Bexarotene, CD3254, Docosahexaenoic acid, fluorobexarotene, isotretinoin, retinoic acid, SR11237, fenretinide, HX630, liarozole dihydrochloride, LG100754 and LG101506.

The present invention is not limited to the use of particular LXR or RXR agonists. In some embodiments, LXR and RXR agonists are combined. For example, in some embodiments, the combination of LXR and RXR agonists are from TO901317, ATI-111, LXR-623, XL-652, hypocholamide, GW3965, N,N-dimethyl-3beta-hydroxy-cholenamide (DMHCA), 22(R)-hydroxycholesterol, 24(S)-hydroxycholesterol, (−)anthrabenzoxocinone and (−)bischloroanthrabenzoxocinone ((−)-BABX)), Bexarotene, CD3254, Docosahexaenoic acid, fluorobexarotene, isotretinoin, retinoic acid, SR11237, fenretinide, HX630, liarozole dihydrochloride, LG100754 and LG101506.

The present invention is not limited to a particular manner of generating sHDL-TA nanoparticles. In some embodiments, for example, such sHDL-TA nanoparticles are formed by mixing an amphipathic lipid and the therapeutic agent in a solvent. The solvent is then removed and the dried lipid mixture is hydrated with an aqueous buffer. HDL apolipoprotein is then added and the composition is mixed vigorously to effect the formation of the sHDL-TA nanoparticles. Example I describes the formation of sHDL-TA nanoparticles wherein the therapeutic agent is sphingosine-1-phosphate (S1P). Example III describes the formation of sHDL-TA nanoparticles wherein the therapeutic agent is an LXR agonist (TO901317). As described, phospholipids, apoA-I mimetic peptide (22A) and TO901317 were hydrated in an aqueous solution and the sHDL-TA nanoparticles were formed after three cydles of thermcal cycling between 25 and 50° C.

Figure 15:
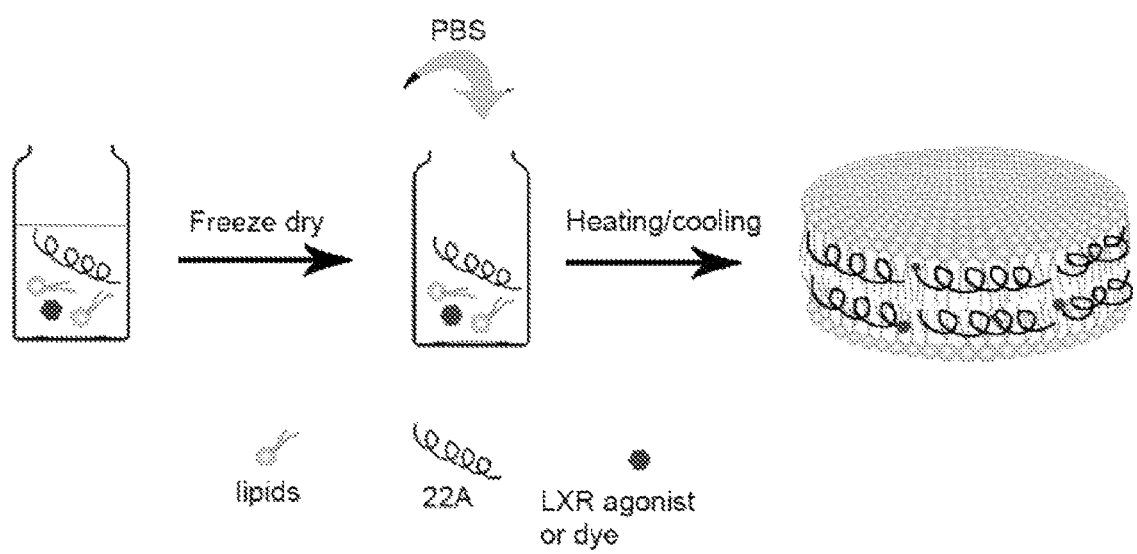
FIG. 15: Schematic for the preparation of LXR agonist-loaded sHDL using the co-lyophilization method.

In some embodiments, the sHDL-TA nanoparticles are prepared by co-lyophilization methods. For example, in some embodiments, lipids, ApoA mimetic peptides and a therapuetuic agent will be dissolved (e.g., in glacial acetic acid) and lyophilized. The obtained powder will be hydrated in PBS (e.g., pH 7.4) and thermocycled above and below the phospholipid transition temperature to form drug-loaded sHDL (see, FIG. 15 showing an LXR agonist as a therapeutic agent).

Generally, the sHDL-TA nanoparticles so formed are spherical and have a diameter of from about 5 nm to about 20 nm (e.g., 4-22 nm, 6-18 nm, 8-15 nm, 8-10 nm, etc.). In some embodiments, the sHDL-TA nanoparticles are subjected to size exclusion chromatography to yield a more homogeneous preparation.

In some embodiments, the sHDL-TA nanoparticles are prepared by a thin-film dispersion method. For example, in some embodiments, lipid (e.g., approximately 15 mg lipid) is dissolved in chloroform (e.g., approximately 2 ml chloroform) and mixed with a drug stock DMSO solution (e.g., approximately 2.5 mg/mL drug stock DMSO solution). In some embodiments, organic solvent is evaporated and buffer (50 mM acetate buffer, pH 5.0) added into the lipid/drug mixture to hydrate the film by probe sonication in intervals (e.g., 30 second intervals) using an ultrasonic processor (e.g., a VibraCell ultrasonic processor (Sonics, Newtown, Conn.)). In some embodiments, apolipoprotein is dissolved in buffer and mixed with the lipid suspension. Next, in some embodiments, the mixture is incubated in water bath (e.g., 50° C. water bath for 5 min) and cooled (e.g., cooled at room temperature for 5 min). In some embodiments, the water bath/cooling is repeated (e.g., cycled three times) to form sHDL-TA nanoparticles.

In some embodiments, the sHDL-TA nanoparticles are prepared by mixing (e.g., vortexing) (e.g., ultraturrexing) buffer with powder formulations of peptide, lipid and therapeutic agent. In some embodiments, the mixture is further incubated at or about the lipid phase transition temperature until sHDL-TA assembly is complete.

Generally, the sHDL-TA nanoparticles so formed are spherical and have a diameter of from about 5 nm to about 20 nm (e.g., 4-22 nm, 6-18 nm, 8-15 nm, 8-10 nm, etc.). In some embodiments, the sHDL-TA nanoparticles are subjected to size exclusion chromatography to yield a more homogeneous preparation.

In some embodiments, the sHDL nanoparticles further encapsulate agents useful for determining the location of administered particles. Agents useful for this purpose include fluorescent tags, radionuclides and contrast agents.

Suitable imaging agents include, but are not limited to, fluorescent molecules such as those described by Molecular Probes (Handbook of fluorescent probes and research products), such as Rhodamine, fluorescein, Texas red, Acridine Orange, Alexa Fluor (various), Allophycocyanin, 7-amino-actinomycin D, BOBO-1, BODIPY (various), Calcien, Calcium Crimson, Calcium green, Calcium Orange, 6-carboxy-rhodamine 6G, Cascade blue, Cascade yellow, DAPI, DiA, DID, Dil, DiO, DiR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3. In some embodiments, ceramides are provided as imaging agents. In some embodiments, SW agonists are provided as imaging agents.

Additionally radionuclides can be used as imaging agents. Suitable radionuclides include, but are not limited to radioactive species of Fe(III), Fe(II), Cu(II), Mg(II), Ca(II), and Zn(I1) Indium, Gallium and Technetium. Other suitable contrast agents include metal ions generally used for chelation in paramagnetic T1-type MIR contrast agents, and include di- and tri-valent cations such as copper, chromium, iron, gadolinium, manganese, erbium, europium, dysprosium and holmium. Metal ions that can be chelated and used for radionuclide imaging, include, but are not limited to metals such as gallium, germanium, cobalt, calcium, indium, iridium, rubidium, yttrium, ruthenium, yttrium, technetium, rhenium, platinum, thallium and samarium. Additionally metal ions known to be useful in neutron-capture radiation therapy include boron and other metals with large nuclear cross-sections. Also suitable are metal ions useful in ultrasound contrast, and X-ray contrast compositions.

Examples of other suitable contrast agents include gases or gas emitting compounds, which are radioopaque.

In some embodiments, the sHDL-TA nanoparticles further encapsulate a targeting agent. In some embodiments, targeting agents are used to assist in delivery of the sHDL-TA nanoparticles to desired body regions (e.g., bodily regions affected by a cardiovascular related disorder). Examples of targeting agents include, but are not limited to, an antibody, receptor ligand, hormone, vitamin, and antigen, however, the present invention is not limited by the nature of the targeting agent. In some embodiments, the antibody is specific for a disease-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid.

In some embodiments, the sHDL-TA nanoparticles further encapsulate transgenes for delivery and expression to a target cell or tissue, in vitro, ex vivo, or in vivo. In such embodiments, rather than containing the actual protein, the sHDL-TA nanoparticles encapsulate an expression vector construct containing, for example, a heterologous DNA encoding a gene of interest and the various regulatory elements that facilitate the production of the particular protein of interest in the target cells.

In some embodiments, the gene is a therapeutic gene that is used, for example, to treat cardiovascular related disorders, to replace a defective gene, or a marker or reporter gene that is used for selection or monitoring purposes. In the context of a gene therapy vector, the gene may be a heterologous piece of DNA. The heterologous DNA may be derived from more than one source (i.e., a multigene construct or a fusion protein). Further, the heterologous DNA may include a regulatory sequence derived from one source and the gene derived from a different source. Tissue-specific promoters may be used to effect transcription in specific tissues or cells so as to reduce potential toxicity or undesirable effects to non-targeted tissues. The nucleic acid may be either cDNA or genomic DNA. The nucleic acid can encode any suitable therapeutic protein.

The nucleic acid may be an antisense nucleic acid. In such embodiments, the antisense nucleic acid may be incorporated into the nanoparticle of the present invention outside of the context of an expression vector.

In some embodiments, the sHDL-TA nanoparticles of the present invention may be delivered to local sites in a patient by a medical device. Medical devices that are suitable for use in the present invention include known devices for the localized delivery of therapeutic agents. Such devices include, but are not limited to, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered; needle injection devices such as hypodermic needles and needle injection catheters; needleless injection devices such as jet injectors; coated stents, bifurcated stents, vascular grafts, stent grafts, etc.; and coated vaso-occlusive devices such as wire coils.

Exemplary devices are described in U.S. Pat. Nos. 5,935,114; 5,908,413; 5,792,105; 5,693,014; 5,674,192; 5,876,445; 5,913,894; 5,868,719; 5,851,228; 5,843,089; 5,800,519; 5,800,508; 5,800,391; 5,354,308; 5,755,722; 5,733,303; 5,866,561; 5,857,998; 5,843,003; and 5,933,145; the entire contents of which are incorporated herein by reference. Exemplary stents that are commercially available and may be used in the present application include the RADIUS (SCIMED LIFE SYSTEMS, Inc.), the SYMPHONY (Boston Scientific Corporation), the Wallstent (Schneider Inc.), the PRECEDENT II (Boston Scientific Corporation) and the NIR (Medinol Inc.). Such devices are delivered to and/or implanted at target locations within the body by known techniques.

As noted, the sHDL-TA nanoparticles of the present invention are useful in treating cardiovascular related disorders. Examples of cardiovascular related disorders include, but are not limited to, atherosclerosis, coronary artery disease, cardiomyopathy, hypertensive heart disease, heart failure, pulmonary heart disease, cardiac dysrhythmias, inflammatory heart disease (e.g., endocarditis, inflammatory cardiomegaly, myocarditis), vulvular heart disease, cerebrovascular disease, peripheral arterial disease, congenital heart disease, and rheumatic heart disease.

The present invention is not limited to a particular method or technique for treating a cardiovascular related disorder. In some embodiments, the methods involve administering to a subject (e.g., a human subject suffering from or at risk for developing a cardiovascular related disorder) a therapeutically effective amount of a composition comprising a sHDL-TA nanoparticle as described herein. The utilized therapeutic agent will depend on the type of condition being treated. For example, if the cardiovascular related disorder is atherosclerosis, the therapeutic agent (in some embodiments) is an LXR agonist (e.g., TO901317) or a RXR agonist (e.g., CD3254).

In some embodiments, the present invention also provides kits comprising sHDL-TA nanoparticles as described herein. In some embodiments, the kits comprise one or more of the reagents and tools necessary to generate sHDL-TA nanoparticles, and methods of using such sHDL-TA nanoparticles.

The sHDL-TA nanoparticles of the present invention may be characterized for size and uniformity by any suitable analytical techniques. These include, but are not limited to, atomic force microscopy (AFM), electrospray-ionization mass spectroscopy, MALDI-TOF mass spectroscopy, $^{13}C$ nuclear magentic resonance spectroscopy, high performance liquid chromatography (HPLC) size exclusion chromatography (SEC) (equipped with multi-angle laser light scattering, dual UV and refractive index detectors), capillary electrophoresis and get electrophoresis. These analytical methods assure the uniformity of the sHDL-TA nanoparticle population and are important in the production quality control for eventual use in in vivo applications.

In some embodiments, gel permeation chromatography (GPC), which can separate sHDL nanoparticles from liposomes and free ApoA-I mimetic peptide, is used to analyze the sHDL-TA nanoparticles. In some embodiments, the size distribution and zeta-potential is determined by dynamic light scattering (DLS) using, for example, a Malven Nanosizer instrument.

In some embodiments, the encapsulation efficiency of the therapeutic agent will be determined by a desalting column method. Briefly, a sHDL-TA nanoparticle will be passed through a desalting column (cut off=7000 Da) to remove any unencapsulated therapeutic agent, and an equal volume of a sHDL-TA nanoparticle that is not subject to desalting will be used as a comparison. All samples will be incubated with ethanol to break sHDL and subsequently analyzed by HPLC equipped with a C18 column[39]. In some embodiments, an equation is used to calculate encapsulation efficiency. In some embodiments, the following equation is used to calculate the encapsulation efficiency: Encapsulation efficiency (%)=(the content of drug in sHDL passed through the desalting column)/(the content of therapeutic agent in sHDL not passed through the desalting column)×100%.

In some embodiments, to learn the release profile of therapeutic agent from sHDL, sHDL-TA nanoparticles and free therapeutic agent are placed into a dialysis bag (6-8kda), which will be put in 200 ml PBS (pH 7.4) containing 0.1% Tween 80[4o]. The release media will be put in a 37° C. air bath shaker at 100 rpm. In some embodiments, at predetermined time points, 2 ml of the medium will be sampled and replaced with an equal volume of fresh release media. The amount of therapeutic agent in the media will be quantified by reverse-phase HPLC.

In some embodiments, the sHDL-TA nanoparticles of the present invention are configured such that they are readily cleared from a subject (e.g., so that there is little to no detectable toxicity at efficacious doses).

Where clinical applications are contemplated, in some embodiments of the present invention, the sHDL-TA nanoparticles are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight sHDL-TA nanoparticle formulation may be administered using one or more of the routes described herein.

In preferred embodiments, the sHDL-TA nanoparticles are used in conjunction with appropriate salts and buffers to render delivery of the compositions in a stable manner to allow for uptake by target cells. Buffers also are employed when the sHDL-TA nanoparticles are introduced into a patient. Aqueous compositions comprise an effective amount of the sHDL-TA nanoparticles to cells dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The active sHDL-TA nanoparticles may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some embodiments, a therapeutic agent is released from the sHDL-TA nanoparticles within a target cell (e.g., within a vascular region) (e.g., within an atheroscleroma).

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active sHDL-TA nanoparticles in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, sHDL-TA nanoparticles are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%-2%. Vaginal suppositories or pessaries are usually globular or oviform and weighing about 5 g each. Vaginal medications are available in a variety of physical forms, e.g., creams, gels or liquids, which depart from the classical concept of suppositories. The sHDL-TA nanoparticles also may be formulated as inhalants.

The present invention also includes methods involving co-administration of the sHDL-TA nanoparticles as described herein with one or more additional active agents. Indeed, it is a further aspect of this invention to provide methods for enhancing prior art therapies and/or pharmaceutical compositions by co-administering the sHDL-TA nanoparticles of this invention. In co-administration procedures, the agents may be administered concurrently or sequentially. In some embodiments, the sHDL-TA nanoparticles described herein are administered prior to the other active agent(s). The agent or agents to be co-administered depends on the type of condition being treated. For example, when the condition being treated is a cardiovascular related disorder, the additional agent includes angiotensin-converting enzyme (ACE) inhibitors (e.g., benazepril, enalapril, Lisinopril, perindopril, Ramipril), adenosine, alpha blockers (alpha adrenergic antagonist medications) (e.g., clonidine, guanabenz, labetalol, phenoxybenzamine, terazosin, doxazosin, guanfacine, methyldopa, prazosin), angtiotensin II receptor blockers (ARBs) (e.g., candesartan, irbesartan, olmesartan medoxomil, telmisartan, eprosartan, losartan, tasosartan, valsartan), anticoagulants (e.g., heparin fondaparinux, warfarin, ardeparin, enoxaparin, reviparin, dalteparin, nadroparin, tinzaparin), antiplatelet agents (e.g., abciximab, clopidogrel, eptifibatide, ticlopidine, cilostazol, dipyridamole, sulfinpyrazone, tirofiban), beta blockers (e.g., acebutolol, betaxolol, carteolol, metoprolol, penbutolol, propranolol, atenolol, bisoprolol, esmolol, nadolol, pindolol, timolol), calcium channel blockers (e.g., amlopidine, felodipine, isradipine, nifedipine, verapamil, diltiazem, nicardipine, nimodipine, nisoldipine), diuretics, aldosterone blockers, loop diuretics (e.g., bumetanide, furosemide, ethacrynic acid, torsemide), potassium-sparing diuretics, thiazide diuretics (e.g., chlorothiazide, chlorthalidone, hydrochlorothiazide, hydroflumethiazide, methyclothiazide, metolazone, polythiazide, quinethazone, trichlormethiazide), inoptropics, bile acid sequestrants (e.g., cholestyramine, coletipol, colesevelam), fibrates (e.g., clofibrate, gemfibrozil, fenofibrate), statins (e.g., atorvastatinm, lovastatin, simvastatin, fluvastatin, pravastatin), selective cholesterol absorption inhibitors (e.g., ezetimibe), potassium channel blockers (e.g., amidarone, ibutilide, dofetilide), sodium channel blockers (e.g., disopyramide, mexiletine, procainamide, quinidine, flecainide, moricizine, propafenone), thrombolytic agents (e.g., alteplase, reteplase, tenecteplase, anistreplase, streptokinase, urokinase), vasoconstrictors, vasodilators (e.g., hydralazine, minoxidil, mecamylamine, isorbide dintrate, isorbide mononitrate, nitroglycerin). The additional agents to be co-administered can be any of the well-known agents in the art, including, but not limited to, those that are currently in clinical use.

Experimental

The following examples are provided in order to demonstrate and further illustrate certain preferred embodiments and aspects of the present invention and are not to be construed as limiting the scope thereof.

Example I

This example describes S1P-sHDL compositions.

Sphingosine-1-phosphate (S1P, CAS 26993-30-6) was obtained from Cayman Chemical Company (Ann Arbor, Mich.). 22A mimetic peptide (SEQ?) and dipalmitoylphosphatidylcholine (DPPC) was obtained from NOF (Japan). Cell culture reagents were obtained from Lonza (Walkersville, Md.).

SP stock solution was prepared in methanol, heating to 55° C. and using bath sonication to help dissolve. 22A mimetic peptide and DPPC were weighed and added to separate vials, followed by the addition of acidified methanol (containing 10-20% glacial acetic acid) to fully dissolve both peptide and lipid. Various amounts (1-500 nmol) of S1P was then added to DPPC solution, followed by the addition of peptide solution to create a 1:2 peptide:lipid ratio by weight. Samples were flash frozen in liquid nitrogen and lyophilized for 24 hours to remove solvents. Once the solvents evaporated, samples were removed from lyophilizer and hydrated to desired concentrations using 1× PBS (pH 7.4). The solutions were vortexed and thermocycled above and below the lipid glass transition temperature (between 25° C. and 50° C. for DPPC). Thermocycling was repeated 3 times, at which point the solution transitioned from cloudy to clear, indicating formation of HDL. Samples were adjusted to pH 7.4 with NaOH and sterile filtered with either a 0.22 or 0.45 μm syringe filter. sHDL particles containing SP weare characterized by gel permeation chromatography (GPC), as seen in FIG. 1.

Example II

This example describes a S1P-HDL in vitro assay.

Figure 2:
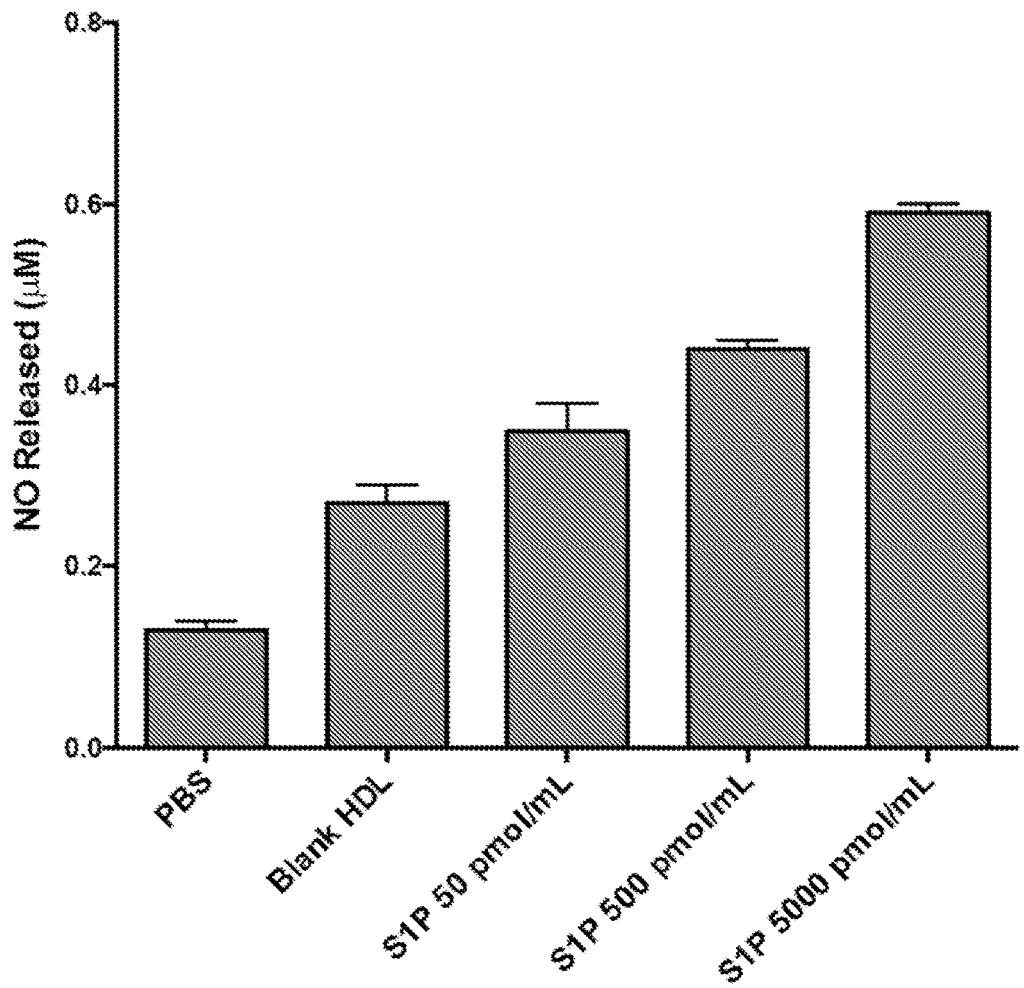
FIG. 2: HUVECs were treated with 1.0 mg/mL HDL (22A:DPPC, 1:2 w/w) containing different concentrations of S1P and released nitric oxide was measured in supernatants by ozone chemiluminescence. Blank 22A:DPPC HDL (1.0 mg/mL) and PBS were used as controls (Example 2).

Human umbilical vein endothelial cells (HUVEC) C2519A Clonetics were recovered from cryopreservation and cultured per manufacturer instruction. At passage 5 the cells were trypsinized, counted, re-plated into 12-well plates at $10^6$ cells per well and incubated for 48 hours at 37° C. and 5% $CO_2$. Media was aspirated and replaced with fresh media containing sHDL, S1P-sHDL, free 22A peptide, or PBS. Cells were placed back into incubator for 10 minutes, after which the media was collected and analyzed for nitric oxide (NO) content via ozone chemiluminescence (FIG. 2). Remaining cells were stripped with trypsin and collected for qRT-PCR analysis. FIG. 2 demonstrates increased NO release with S1P-HDL.

Example III

This example demonstrates that LXR agonist-sHDL successfully upregulated ABCA1 expression in macrophages.

Figure 3:
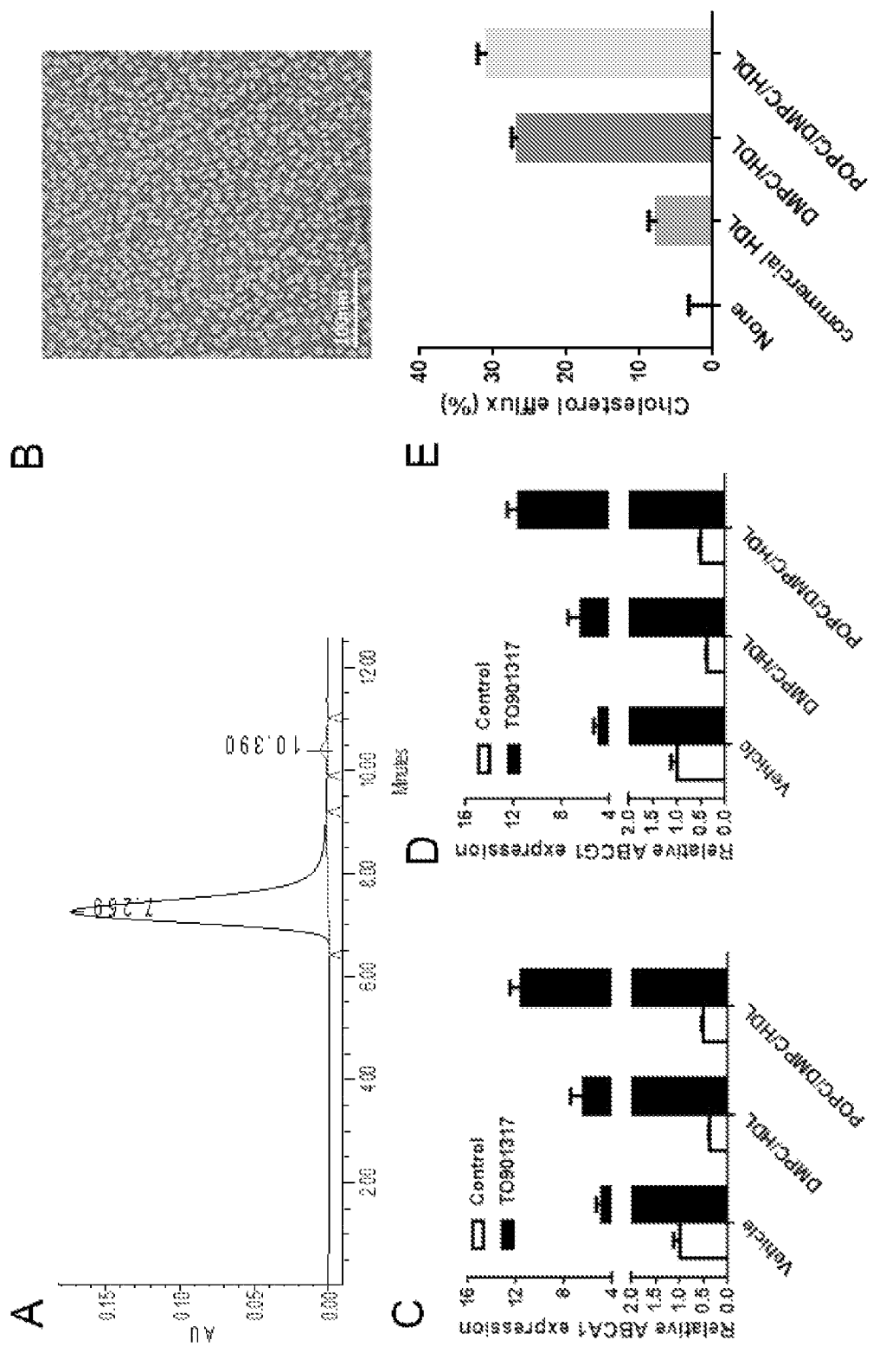
FIG. 3: (A) Homogeneous size distribution of LXR-sHDL measured by GPC; (B) SEM images of LXR-sHDL at 150,000-fold magnification; (C-D) qRT-PCR analysis of ABCA1 expression (C) and AGCG1 expression (D) in J774.1 macrophages treated with DMSO control, TO901317-LXR agonist in DMSO solution, blank sHDL made from DMPC, TO901317-sHDL made from DMPC, blank sHDL made from POPC/DMPC mixture, and TO901317-sHDL made from POPC/DMPC; (E) TO901317-DMPC-sHDL and TO901317-DMPC/POPC-sHDL induced more cholesterol efflux in macrophages compared to the blank HDL and buffer controls.

Incorporation of LXR agonist into sHDL is the first and most important step for all subsequent studies. Phospholipids, apoA-I mimetic peptide (22A) and LXR agonist TO901317 (TO) were hydrated in an aqueous solution and the sHDL nanoparticles were formed after 3 cycles of thermal cycling between 25 and 50° C. (see, e.g., Di Bartolo, B. A.; et al., Atherosclerosis 2011, 217 (2), 395-400; Dasseux, J.-L. Peptide/lipid complex formation by co-lyophilization. 2001). The homogeneity of the size distribution was confirmed by gel permeation chromatography (GPC) and scanning electron microscopy (SEM) (FIG. 3A-B). The average particle size of sHDL was 6-14 nm (e.g., 8-10 nm) as determined by dynamic light scattering using a Malvern Nanosizer. To assess the therapeutic potential and function of LXR agonist-sHDL, its effect on modulation of ABCA1 and ABCG1 levels in vitro was investigated. Free LXR agonist upregulated ABCA1 and ABCG1 in J774.1 macrophages, but increased upregulation was observed for LXR agonist-sHDL treated macrophages (FIG. 3C-D). In addition, incubation of J774.1 macrophages with LXR agonist-sHDL nanoparticles led to increased cholesterol efflux from macrophages than that of other formulations (FIG. 3E), indicating, for example, sHDL is an efficient carrier for LXR agonist delivery in vitro.

Example IV

This example shows synthetic HDL (sHDL) nanomedicines can accumulate in atherosclerotic lesions, with less side effects than free LXR agonists.

Figure 4A:
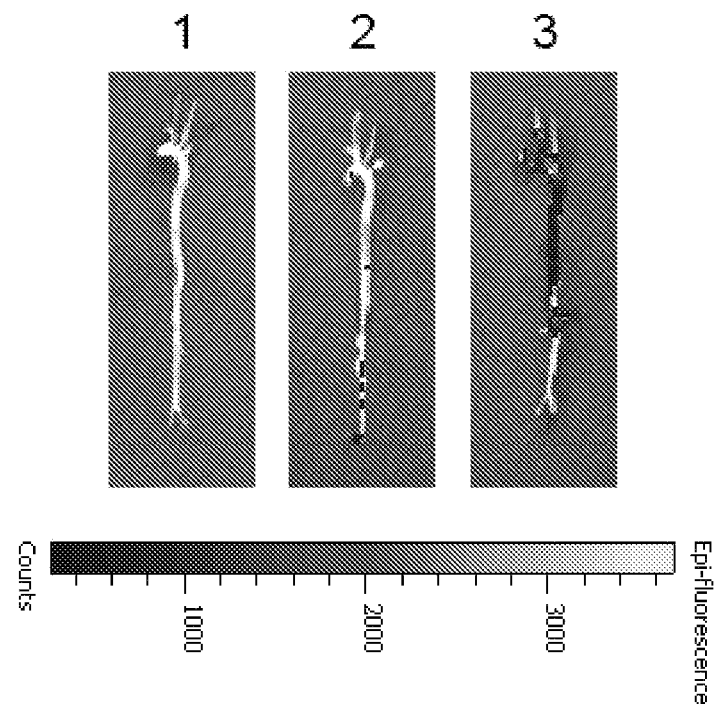
FIG. 4: (A) DiD-sHDL can accumulate in the plaque of ApoE-deficient mouse with atherosclerosis. 1=No treatment; 2=blank sHDL; 3=fluorescent labeled DiD-sHDL. (B) Quantitative RT-PCR of the liver lysate showed that LXR agonist-sHDL (sHDL-TO) had much less effects on the SREBP1c expression relative to free LXR agonist (TO) at all TO concentrations 0.5, 1.5 and 10 mg/mL.
Figure 4B:
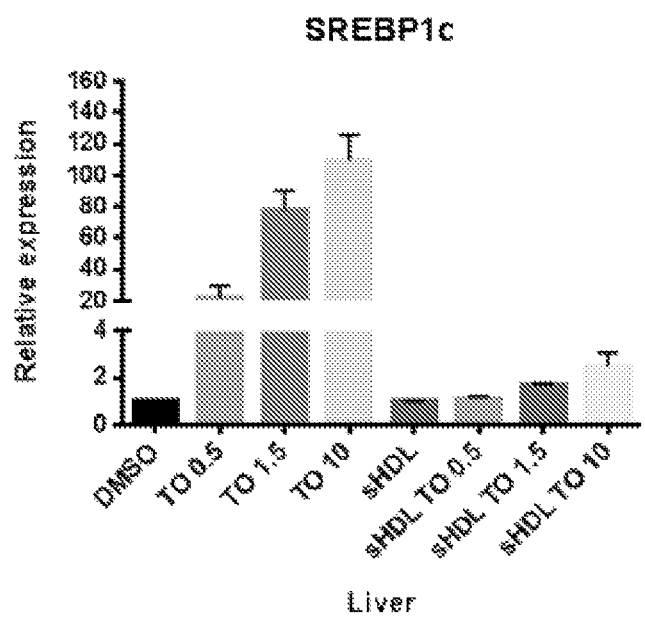

To visualize whether sHDL can deliver its cargo to the plaque efficiently, a lipophilic near-infrared fluorescent dye, DiD, was incorporated into sHDL. DiD was chosen because it exhibits little auto-fluorescence and possesses a low phototoxicity. The DiD-labeled sHDL nanoparticles were administrated by tail vein injection at a dose of 100 µg DiD and 10 mg/Kg sHDL to a murine atherosclerosis model. 24 hours post injection, animals were sacrificed and aortas were removed. DiD fluorescence associated with aortas were analyzed using the Xenogen IVIS optical imaging system. This study clearly showed that the sHDL nanoparticles accumulated in atherosclerotic lesions (FIG. 4). The side effects of different LXR agonist formulations were assessed. It turned out that the LXR agonist-sHDL formulation (sHDL-TO) induced much lower SREBP1c expression (a marker for lipogenesis in the liver) than free LXR agonist, indicating sHDL-TO had less side effects.

Figure 5:
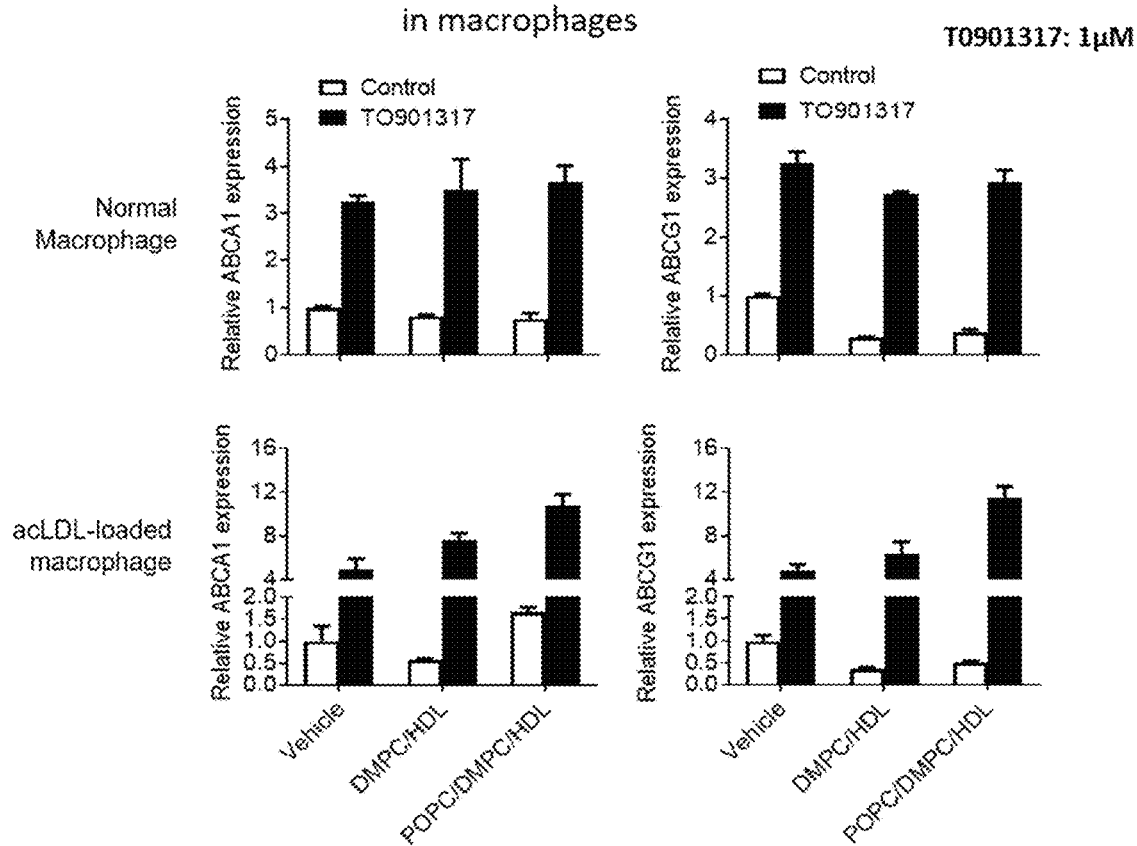
FIG. 5 shows regulation of LXR-target gene expression by TO901317-encapsulated sHDL particles in macrophages.

FIG. 5 shows regulation of LXR-target gene expression by TO901317-encapsulated sHDL particles in macrophages. In macrophages, LXRs control transcription of several genes involved in the cholesterol efflux pathway, including ABCA1 and ABCG1. To examine the ability of TO901317-encapsulated sHDL particles to activate LXR-target genes, J774.1 murine macrophage cells were incubated with sHDL blank particles or TO901317-encapsulated sHDL particles (TO901317 at $10^{-6}$M) for 4 hours and the expression of both genes were measured using quantitative real-time PCR (qRT-PCR). RNA from cells was isolated using Qiagen RNA isolation kit. Approximately 2 µg of total RNA was reverse transcribed using Superscript-II reverse transcriptase kit to generate cDNA (Invitrogen). The resulting cDNA was amplified with appropriate primers using power SYBR Green PCR Master Mix and analyzed on a CFX real-time PCR system (Bio-Rad). Reactions were run in triplicates and GAPDH was used as an internal control to normalize for the variability in expression levels. Data analysis was performed using the 2-ΔΔCT method. The results indicated that TO901317-encapsulated sHDL particles can upregulate ABCA1 and ABCG1 expression in macrophages at both baseline and lipid loaded conditions.

Figure 6:
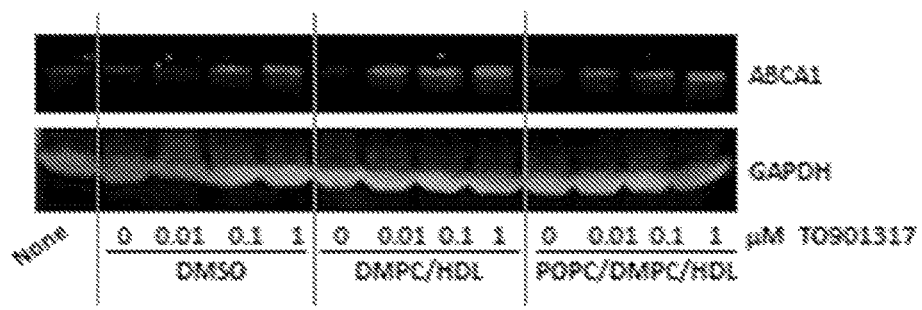
FIG. 6 shows westernblot analysis for the expression of ABCA1 in TO901317-encapsulated sHDL particles treated macrophages.

FIG. 6 shows westernblot analysis for the expression of ABCA1 in TO901317-encapsulated sHDL particles treated macrophages. J774.1 murine macrophage cells were incubated with sHDL blank particles or TO901317-encapsulated sHDL particles for 18 hours. The cells were lysed using RIPA buffer (50 mM Tris-HCl pH 7.4, 150 mM NaCl, 1% (v/v) NP-40, 0.5% (w/v) sodium deoxycholate, 10 mM sodium fluoride, 1 mM sodium orthovanadate, 1 mM PMSF, 10 mM sodium pyrophosphate, 0.1% (w/v), SDS supplemented with protease inhibitor solution (Complete, Roche). After lysis the cells were centrifuged at 14,000 rpm for 20 minutes and the proteins were quantified using Protein Assay Reagent (Thermo Scientific, Rockford, Ill.). Equal amounts of proteins were separated using SDS-PAGE and then transferred onto a Hybond nitrocellulose membrane (GE Healthcare Life Sciences, Piscataway, N.J.). The membranes were blocked using 5% milk and probed over night with appropriate dilutions of the primary antibodies (ABCA1 or GAPDH) for proteins. The blots were then washed three times with TBST and incubated with 1:10000 dilutions of secondary antibodies from LI-COR. The bands were visualized using Odyssey CLx Imager. The results indicated that TO901317-encapsulated sHDL particles can upregulate ABCA1 expression in macrophages.

Figure 7:
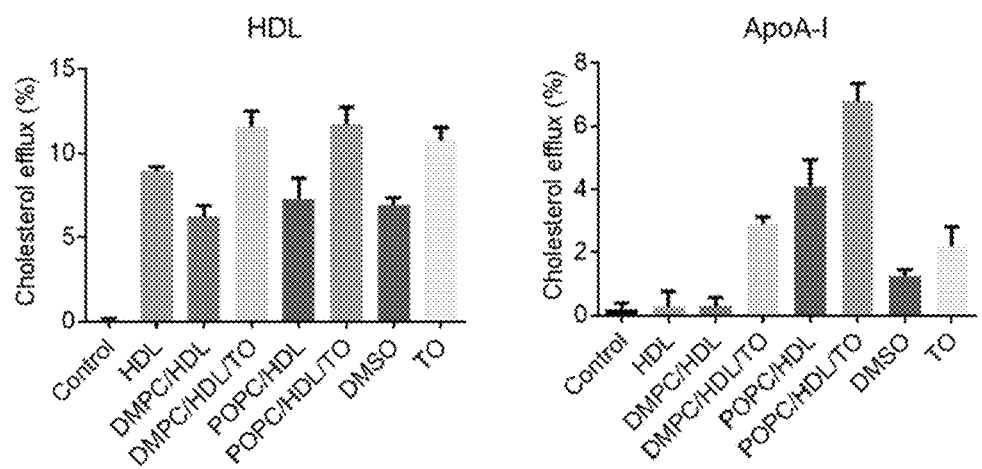
FIG. 7 shows the effects of TO901317-encapsulated sHDL particles on cholesterol efflux in macrophage.

FIG. 7 shows the effects of TO901317-encapsulated sHDL particles on cholesterol efflux in macrophage. After incubation with $^3$H-cholerstol for 24h, J774.1 cells were washed and equilibrated in serum-free medium with acyl:coenzyme A cholesterol O-acyltransferase-1 inhibitor overnight in the presence of DMSO, TO901317 at 10 uM, sHDL blank particles, and TO901317-encapsulated sHDL particles with TO901317 at 10 uM for 24 hours. The cells were incubated in DMEM/0.2% fatty acid-free BSA with 20 µg/ml apoA-I (Alfa Aesar, Mass.) or 100 µg/ml HDL (Sigma) as acceptors for 4h. Efflux capacity was quantified using liquid scintillation to measure radioactive cholesterol effluxed from the cells (medium+intracellular lipids). The results indicated that TO901317-encapsulated sHDL particles can enhance cholesterol efflux in macrophages.

FIGS. 8A and 8B show the effects of TO901317-encapsulated sHDL particles on plasma lipids in C57BL/6J Mice. C57BL/6J wild type mice were divided into 8 groups and treated with DMSO, TO901317 at 0.5 mg/kg, TO901317 at 1.5 mg/kg, TO901317 at 10 mg/kg, or sHDL blank particles, TO901317-encapsulated sHDL particles with TO901317 at 0.5 mg/kg, TO901317-encapsulated sHDL particles with TO901317 at 1.5 mg/kg, TO901317-encapsulated sHDL particles with TO901317 at 10 mg/kg via intraperitoneal injection. Twenty-four hours later, collected plasma and liver tissues were stored at −80° C. until processed. Direct LDL-cholesterol (LDL-c), direct HDL-cholesterol (HDL-c), and enzymatic-colorimetric assays used to determine plasma total cholesterol (TC) and triglycerides (TG) were carried out at the Chemistry Laboratory of the Michigan Diabetes Research and Training Center. The plasma TG levels were significantly elevated in free TO901317 treated groups as compared with control (DMSO). TO901317-encapsulated sHDL particles treated groups did not increase plasma TG levels compared to free TO901317 treated groups at equivalent TO901317 dosage.

Figure 9:
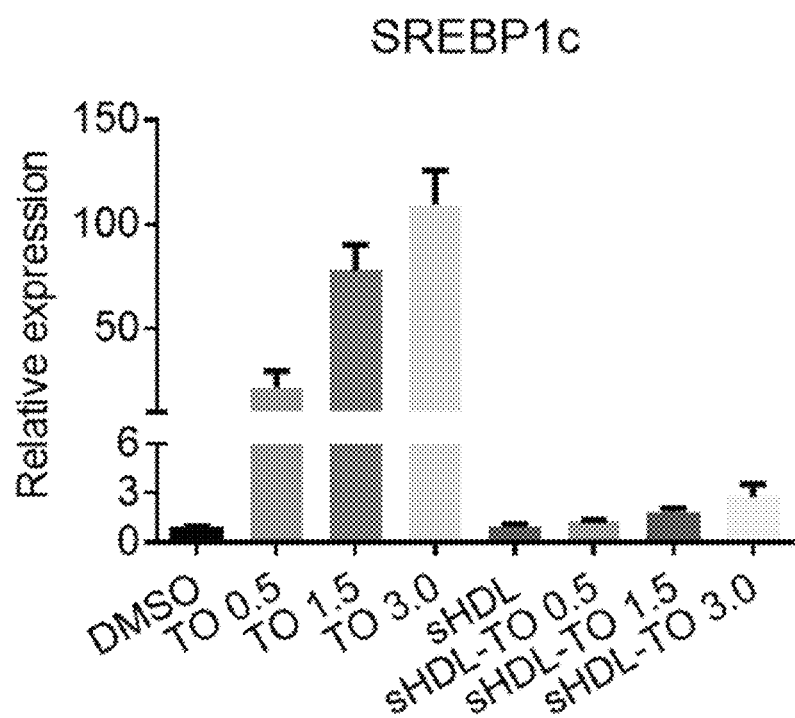
FIG. 9 shows an RT-PCR analysis for the expression of SREBP1c in the liver.

FIG. 9 shows an RT-PCR analysis for the expression of SREBP1c in the liver. LXR ligands have been implicated in triggering induction of the lipogenic pathway via activation of sterol regulatory element-binding transcription factor 1

(SREBP1c) in the liver, which leads to the adverse effects of steatosis and hypertriglyceridemia. The liver tissues from FIG. 8 were used to detect the expression of SREBP1c using qRT-PCR as described in FIG. 5. The results indicated that TO901317 activated SREBP1c in the liver, but TO901317-encapsulated sHDL particles did not significantly activate the expression of SREBP1c in the liver.

Figure 10:
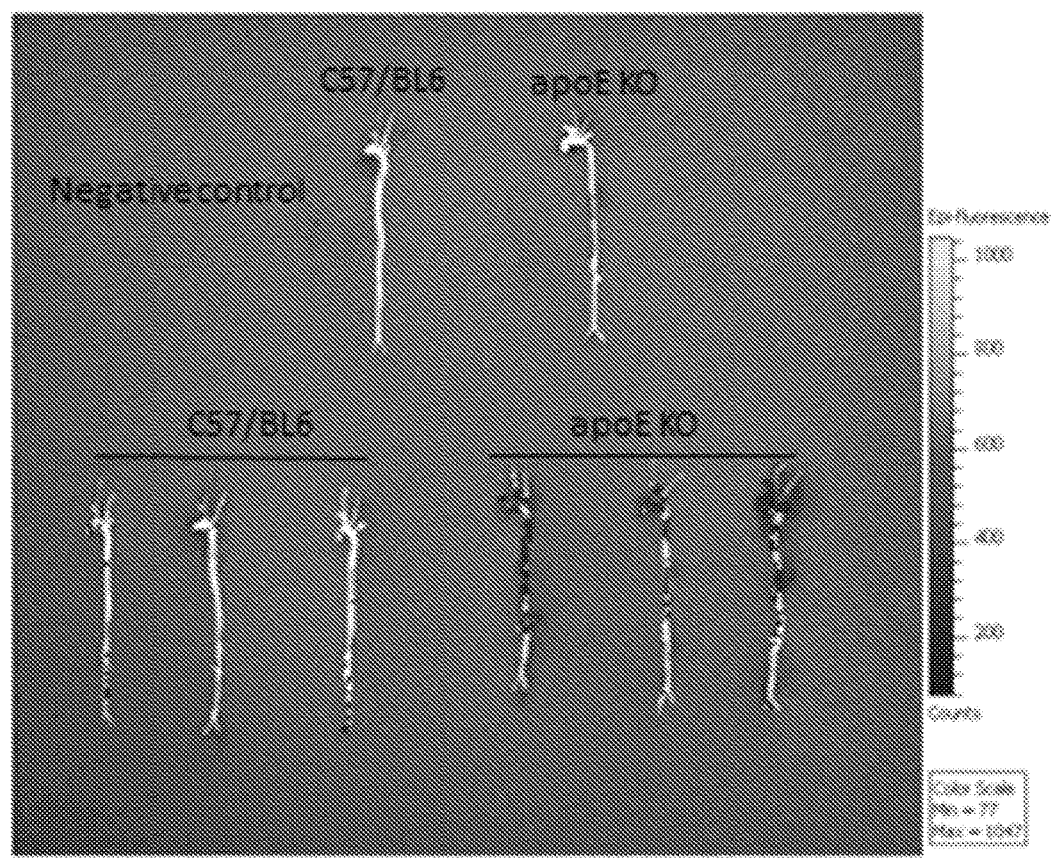
FIG. 10 shows sHDL nanoparticle can deliver compound to atherosclerotic lesions.

FIG. 10 shows sHDL nanoparticle can deliver compound to atherosclerotic lesions. Six-week-old male apoE$^{-/-}$ mice were place on atherogenic high fat diet (HFD) for 12 weeks to induce atherosclerotic lesion formation. In order to characterize whether sHDL nanoparticle can delivery compound to atherosclerotic lesions, we employed ex vivo imaging of aorta trees from apoE$^{-/-}$ mice and normal C57BL/6J mice administered with fluorescently labeled HDL particles using a Xenogen IVIS Spectrum Imaging System. Two hours after intravenous injection of DiD-sHDL, we observed the fluorescence signal accumulation in the aortic tree of apoE$^{-/-}$ mice and the fluorescence signal kept for at least for 6 days, but not in the aorta from the normal C57BL/6J mice. This figure shows the representative image at 24 h after injection.

FIG. 11 shows TO901317-encapsulated sHDL nanoparticles can activate ABCA1 and ABCG1 expression in monocytes in vivo. The effect of TO901317-encapsulated sHDL on target gene expression in monocytes from apoE$^{-/-}$ mice was also investigated. Six-week-old male apoE$^{-/-}$ mice were place on atherogenic high fat diet (HFD) for 12 weeks to induce atherosclerotic lesion formation. Mice were randomly divided into five groups, and each group was treated with intraperitoneal injections of the following regimens with an equivalent dose of 1.5 mg/kg entrapped TO901317: 1) PBS, 2) DMSO, 3) TO901317 dissolved in dimethyl sulfoxide (DMSO) (free TO901317), 4) sHDL nanoparticles, or 5) TO901317-encapsulated sHDL particles. The mice were treated for 6 weeks (three times per week, on Monday, Wednesday and Friday). The monocytes from the blood were isolated and the expression of ABCA1 and ABCG1 was detected by qRT-PCR as described in FIG. 5. Both the free TO901317 and TO901317-encapsulated sHDL activated the expression of ABCA1 and ABCG1 in monocytes.

Figure 12:
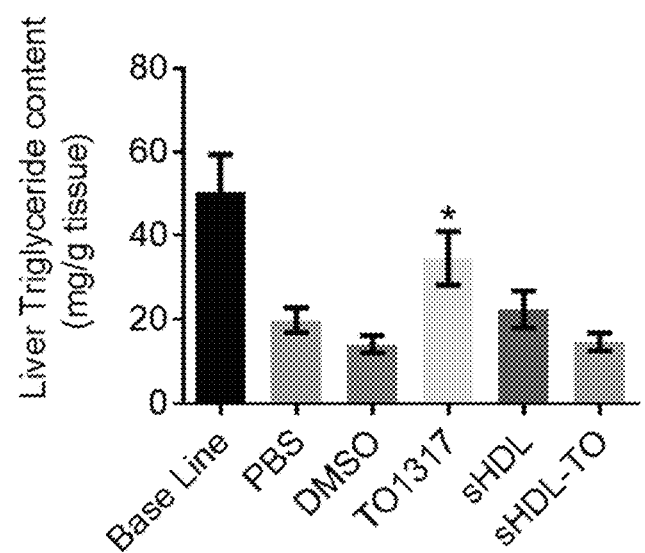
FIG. 12 shows TO901317-encapsulated sHDL nanoparticles induced less triglyceride accumulation in the liver.

FIG. 12 shows TO901317-encapsulated sHDL nanoparticles induced less triglyceride accumulation in the liver. Six-week-old male apoE$^{-/-}$ mice were place on atherogenic high fat diet (HFD) for 12 weeks to induce atherosclerotic lesion formation. Mice were randomly divided into five groups, and each group was treated with intraperitoneal injections of the following regimens with an equivalent dose of 1.5 mg/kg entrapped TO901317: 1) PBS, 2) DMSO, 3) TO901317 dissolved in dimethyl sulfoxide (DMSO) (free TO901317), 4) sHDL nanoparticles, or 5) TO901317-encapsulated sHDL particles. The mice were treated for 6 weeks (three times per week, on Monday, Wednesday and Friday). Liver tissue triglyceride concentrations were measured using a Triglyceride Quantification Kit (Cayman). Fifty mg of liver was homogenized in a 5% NP-40 buffer, and assay was performed according to manufacturer's directions. In the liver, free TO901317 significantly induced the accumulation of triglyceride. TO901317-encapsulated sHDL particles protected against the induction of triglyceride accumulation.

FIG. 13 shows TO901317-encapsulated sHDL nanoparticles induced less SREBP-1c and FAS expression in the liver. LXR ligands have been implicated in triggering induction of the lipogenic pathway via activation of SREBP-1c in the liver, which leads to the adverse effects of steatosis and hypertriglyceridemia. The liver tissues from FIG. 12 were used to detect the expression of SREBP1c and Fatty acid synthase (FAS) using qRT-PCR as described in FIG. 5. The results indicated that TO901317 activated SREBP1c in the liver, but TO901317-encapsulated sHDL particles did not significantly activate the expression of SREBP1c in the liver.

Figure 14:
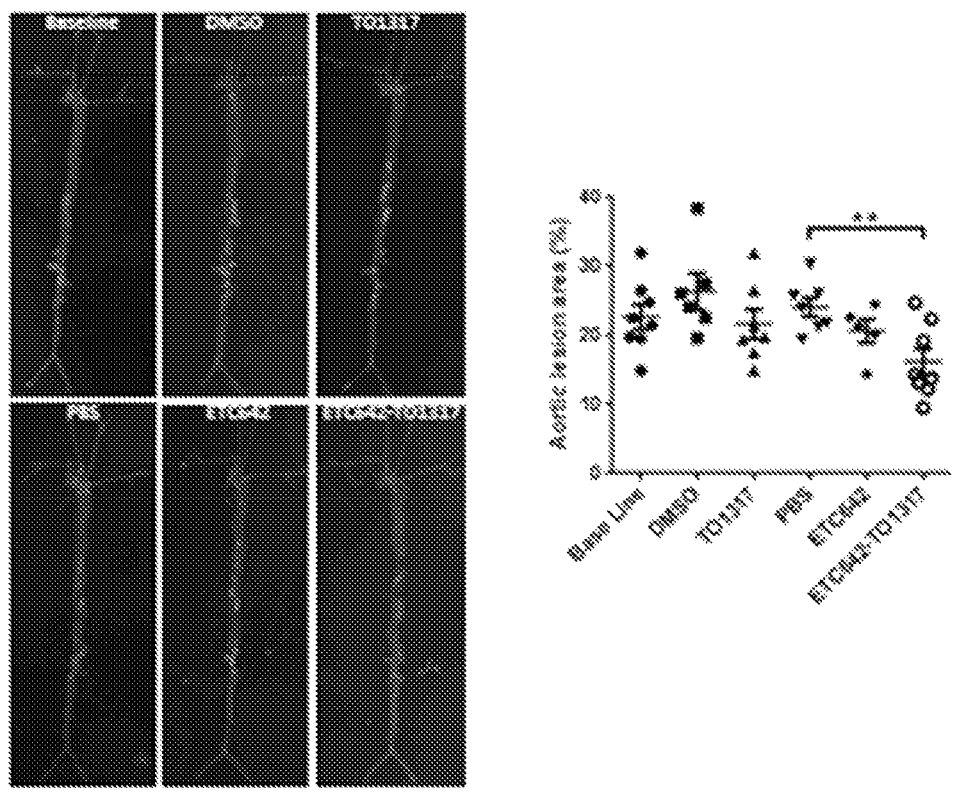
FIG. 14 shows that TO901317-encapsulated sHDL nanoparticles induces atherosclerosis regression in vivo.

FIG. 14 shows that TO901317-encapsulated sHDL nanoparticles induces atherosclerosis regression in vivo. Six-week-old male apoE$^{-/-}$ mice were place on HFD for 14 weeks to induce atherosclerotic lesion formation. Then the atherogenic diet was switched to a regular cholesterol-free chow diet containing 4.3% fat and no added cholesterol, at which point mice were either sacrificed (baseline) or switched to chow diet for 6 weeks. Coincident with the switch to chow diet, mice were randomized into 5 groups and received intraperitoneal injection with 1) PBS, 2) DMSO, 3) TO901317 dissolved in dimethyl sulfoxide (DMSO) (free TO901317, at 1.5 mg/kg), 4) sHDL nanoparticles, or 5) TO901317-encapsulated sHDL particles with a dose of 1.5 mg/kg of TO901317. The mice were treated for 6 weeks (three times per week, on Monday, Wednesday and Friday). For the en face analysis of atheromatous plaques, the adventitia of the whole aorta was removed and aortas were opened longitudinally, stained with Oil red O (Sigma) and pinned flat onto a black-wax plate. The percentage of the plaque area stained by oil red O with respect to the total luminal surface area was quantified. TO901317-encapsulated sHDL particles induced atherosclerosis regression.

Example V

This example describes the materials and methods used in conducting the experiments described in Example 6.
Preparation of Drug-Loaded sHDL Nanoparticles
Drug-loaded sHDL nanoparticles were prepared by a co-lyophilization method. Briefly, lipids, ApoA mimetic peptides and a therapeutic agent (TO901317, Rosiglitazone, or CD3254) were dissolved in glacial acetic acid and lyophilized. The obtained powder was hydrated in PBS (pH 7.4) and thermocycled above and below the phospholipid transition temperature to form drug-loaded sHDL nanoparticles.
Characterization of Drug-Loaded sHDL Nanoparticles
Size and Morphology
The drug-loaded sHDL nanoparticles were characterized for purity by gel permeation chromatography (GPC), which can separate sHDL nanoparticles from liposomes and free ApoA-I mimetic peptide. The size distribution and zeta-potential were determined by dynamic light scattering (DLS) using a Malven Nanosizer instrument after proper dilution of samples.

To observe the morphology of drug-loaded sHDL nanoparticles, they were further characterized by transmission electron microscopy (TEM). Briefly, 3 μL of the sample solution was deposited on carbon film-coated 400 mesh copper grids (Electron Microscopy Sciences) and dried for 1 minute. The samples were then negatively-stained with 5 droplets of 1% uranyl acetate solution, excessive solutions on the grid were blotted and the grid was dried before TEM observation.

Encapsulation efficiency
The encapsulation efficiency of the therapeutic agent was determined by a desalting column method. Briefly, drug-loaded sHDL was passed through a desalting column (MWCO=7000 Da) to remove any unencapsulated drug, and an equal vole of a sHDL-TA nanoparticle not passed through the desalting column was used as a control to calculate the total amount of unencapsulated and encapsulated drug. All samples were incubated with ethanol to break sHDL and subsequently analyzed by HPLC equipped with a C18 column.

The following equation was used to calculate the encapsulation efficiency: Encapsulation efficiency (%)=(the content of drug in sHDL passed through the desalting column)/(the content of therapeutic agent in sHDL not passed through the desalting column)×100%.

Drug Release from sHDL Nanoparticles

To learn the release profile of therapeutic agent from sHDL, drug-loaded sHDL nanoparticles or free therapeutic agent was placed into a dialysis bag (6-8 kda), which was put in 200 ml PBS (pH 7.4) containing 0.1% Tween 80. The release medium was put in a 37° C. air bath shaker at 100 rpm. At predetermined time points, 2 ml of the medium was sampled and an equal volume of fresh release medium was added back. The amount of therapeutic agent in the release medium was quantified by reverse-phase HPLC.

Example VI

This example demonstrates the successful encapsulation of six compounds and fatty acids in sHDL nanoparticles. For example, the average particle sizes of sHDL and sHDL-TO (TO901317, Rosiglitazone, or CD3254) nanoparticles 8-12 nm measured by transmission electron microscopy. The sHDL-TO encapsulation efficiency was more than 85%. Four of those compounds were shown to have the ability to upregulate the expression of ABC transporters, which predominately control cholesterol efflux activity in macrophages. sHDL-compound nanoparticle treatment can significantly increase the upregulative effects of those compounds.

FIG. 16 shows compound-encapsulated sHDL nanoparticles can enhance ABCA1 expression compared to sHDL nanoparticle-treated and free compound-treated macrophages. THP-1-differentiated macrophages were incubated with DMSO, free compound, sHDL blank particles or compound-encapsulated sHDL particles (compound concentration at $10^{-6}$M) for 16 hours and the expression of indicated genes were measured using quantitative real-time PCR (qRT-PCR). RNA from cells was isolated using Qiagen RNA isolation kit. Approximately 2 µg of total RNA was reverse transcribed using Superscript-II reverse transcriptase kit to generate cDNA (Invitrogen). The resulting cDNA was amplified with appropriate primers using power SYBR Green PCR Master Mix and analyzed on a CFX real-time PCR system (Bio-Rad). Reactions were run in triplicates and GAPDH was used as an internal control to normalize for the variability in expression levels. Data analysis was performed using the $2^{-\Delta\Delta CT}$ method. The results indicated that compound-encapsulated sHDL particles can significantely upregulate ABCA1 expression in human macrophages compared to free compound-treated cells and sHDL-treated cells.

FIG. 17 shows compound-encapsulated sHDL nanoparticles can enhance ABCG1 expression compared to sHDL nanoparticle-treated and free compound-treated macrophages. THP-1-differentiated macrophages were incubated with DMSO, free compound, sHDL blank particles or compound-encapsulated sHDL particles (compound concentration at $10^{-6}$M) for 16 hours and the expression of indicated genes were measured using quantitative real-time PCR (qRT-PCR). RNA from cells was isolated using Qiagen RNA isolation kit. Approximately 2 µg of total RNA was reverse transcribed using Superscript-II reverse transcriptase kit to generate cDNA (Invitrogen). The resulting cDNA was amplified with appropriate primers using power SYBR Green PCR Master Mix and analyzed on a CFX real-time PCR system (Bio-Rad). Reactions were run in triplicates and GAPDH was used as an internal control to normalize for the variability in expression levels. Data analysis was performed using the $2^{-\Delta\Delta CT}$ method. The results indicated that compound-encapsulated sHDL particles can significantely upregulate ABCG1 expression in human macrophages compared to free compound-treated cells and sHDL-treated cells.

FIG. 18 shows compound-encapsulated sHDL nanoparticles can enhance SR-BI expression compared to sHDL nanoparticle-treated and free compound-treated macrophages. THP-1-differentiated macrophages were incubated with DMSO, free compound, sHDL blank particles or compound-encapsulated sHDL particles (compound concentration at $10^{-6}$M) for 16 hours and the expression of indicated genes were measured using quantitative real-time PCR (qRT-PCR). RNA from cells was isolated using Qiagen RNA isolation kit. Approximately 2 µg of total RNA was reverse transcribed using Superscript-II reverse transcriptase kit to generate cDNA (Invitrogen). The resulting cDNA was amplified with appropriate primers using power SYBR Green PCR Master Mix and analyzed on a CFX real-time PCR system (Bio-Rad). Reactions were run in triplicates and GAPDH was used as an internal control to normalize for the variability in expression levels. Data analysis was performed using the $2^{-\Delta\Delta CT}$ method. The results indicated that compound-encapsulated sHDL particles can significantely upregulate SR-BI expression in human macrophages compared to free compound-treated cells and sHDL-treated cells.

FIG. 19 shows compound-encapsulated sHDL nanoparticles can enhance cholesterol efflux compared to sHDL nanoparticle-treated and free compound-treated macrophages. THP-1-differentiated macrophages were incubated with 3H-cholerstol for 24 h, washed and equilibrated in serum-free medium with acyl:coenzyme A cholesterol O-acyltransferase-1 inhibitor overnight in the presence of DMSO, free compound at 10 uM, sHDL blank particles, and compound-encapsulated sHDL particles (compound concentration at 10 uM) for 16 hours. Efflux capacity was quantified using liquid scintillation to measure radioactive cholesterol effluxed from the cells (medium+intracellular lipids). The results indicated that compound-encapsulated sHDL particles can enhance cholesterol efflux in human monocyte-differentiated macrophages compared to free compound- and sHDL particles-treated cells.

Figure 20:
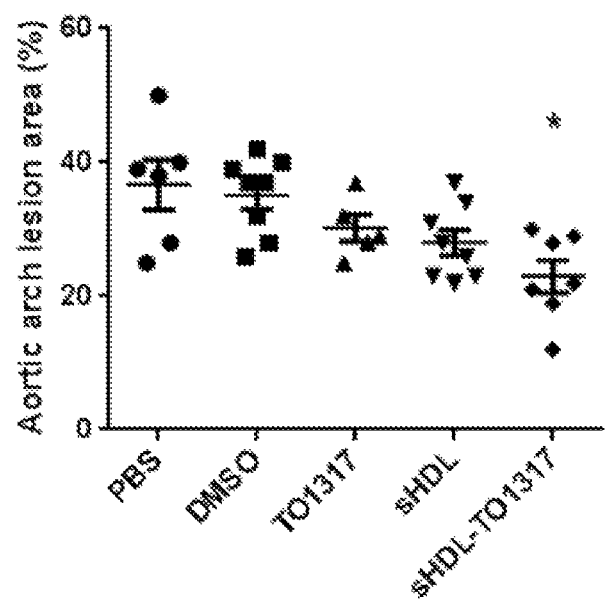
FIG. 20 shows TO901317-encapsulated sHDL nanoparticles can attenuate atherosclerotic lesion formation compared to sHDL nanoparticle-treated and TO901317-treated apoE-deficient mice.

FIG. 20 shows TO901317-encapsulated sHDL nanoparticles can attenuate atherosclerotic lesion formation compared to sHDL nanoparticle-treated and TO901317-treated apoE-deficient mice. Six-week-old male apoE$^{-/-}$ mice were place on HFD for 6 weeks to induce atherosclerotic lesion formation. Mice were randomized into 5 groups and received intraperitoneal injection with 1) PBS, 2) DMSO, 3) TO901317 dissolved in dimethyl sulfoxide (DMSO) (free TO901317, at 1.5 mg/kg), 4) sHDL nanoparticles, or 5) TO901317-encapsulated sHDL particles with a dose of 1.5 mg/kg of TO901317. The mice were treated for 6 weeks (three times per week, on Monday, Wednesday and Friday). For the en face analysis of atheromatous plaques, the adventitia of the whole aorta was removed and aortas were opened longitudinally, stained with Oil red O (Sigma) and pinned flat onto a black-wax plate. The percentage of the plaque area stained by oil red O with respect to the total luminal surface area was quantified. TO901317-encapsulated sHDL particles inhibits atherosclerosis progression.

Figure 21:
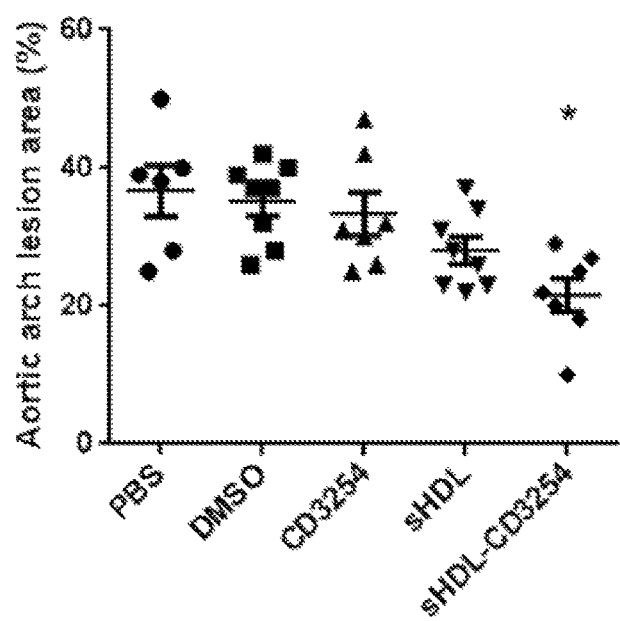
FIG. 21 shows CD3254-encapsulated sHDL nanoparticles can attenuate atherosclerotic lesion formation compared to sHDL nanoparticle-treated and CD3254-treated apoE-deficient mice.

FIG. 21 shows CD3254-encapsulated sHDL nanoparticles can attenuate atherosclerotic lesion formation compared to sHDL nanoparticle-treated and CD3254-treated apoE-deficient mice. Six-week-old male apoE$^{-/-}$ mice were place on HFD for 6 weeks to induce atherosclerotic lesion formation. Mice were randomized into 5 groups and received intraperitoneal injection with 1) PBS, 2) DMSO, 3) CD3254 dissolved in dimethyl sulfoxide (DMSO) (free CD3254, at 0.1 mg/kg), 4) sHDL nanoparticles, or 5) CD3254-encapsulated sHDL particles with a dose of 0.1 mg/kg of CD3254. The mice were treated for 6 weeks (three times per week, on Monday, Wednesday and Friday). For the en face analysis of atheromatous plaques, the adventitia of the whole aorta was removed and aortas were opened longitudinally, stained with Oil red O (Sigma) and pinned flat onto a black-wax plate. The percentage of the plaque area stained by oil red O with respect to the total luminal surface area was quantified. CD3254-encapsulated sHDL particles inhibits atherosclerosis progression.

Figure 22:
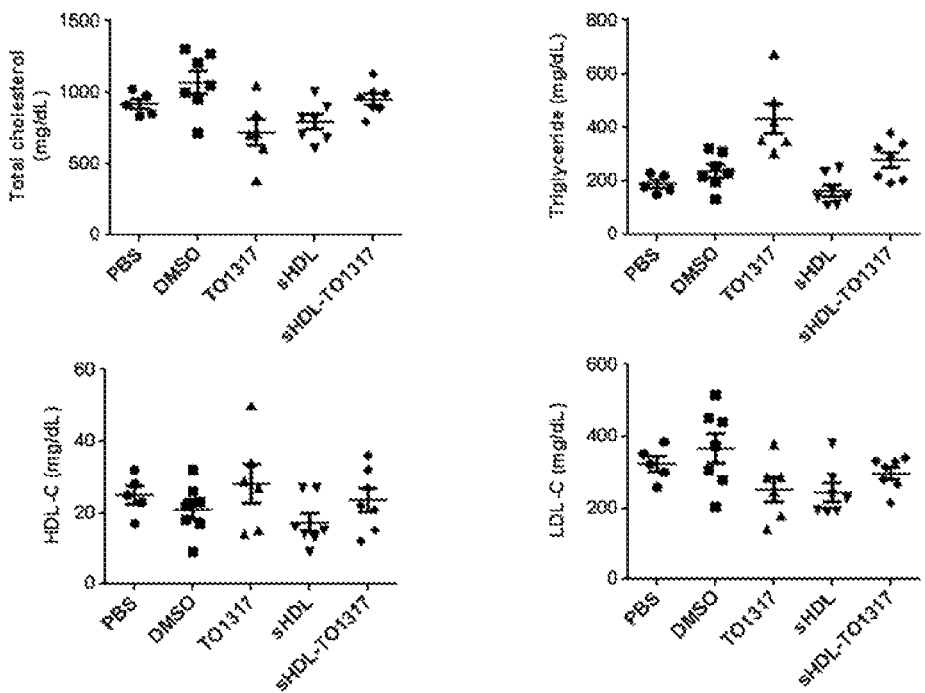
FIG. 22 shows TO901317 treatment induced increased triglyceride levels, whereas TO901317-encapsulated sHDL nanoparticles treatment did not induce triglyceride increase in apoE-deficient mice.

FIG. 22 shows TO901317 treatment induced increased triglyceride levels, whereas TO901317-encapsulated sHDL nanoparticles treatment did not induce triglyceride increase in apoE-deficient mice. Six-week-old male apoE$^{-/-}$ mice were place on HFD for 6 weeks to induce atherosclerotic lesion formation. Mice were randomized into 5 groups and received intraperitoneal injection with 1) PBS, 2) DMSO, 3) CD3254 dissolved in dimethyl sulfoxide (DMSO) (free CD3254, at 0.1 mg/kg), 4) sHDL nanoparticles, or 5) CD3254-encapsulated sHDL particles with a dose of 0.1 mg/kg of CD3254. The mice were treated for 6 weeks (three times per week, on Monday, Wednesday and Friday). Direct LDL-cholesterol (LDL-c), direct HDL-cholesterol (HDL-c), and enzymatic-colorimetric assays used to determine plasma total cholesterol (TC) and triglycerides (TG) were carried out at the Chemistry Laboratory of the Michigan Diabetes Research and Training Center. The plasma TG levels were significantly elevated in free TO901317 treated groups as compared with control (DMSO). TO901317-encapsulated sHDL particles treated groups did not increase plasma TG levels compared to free TO901317 treated groups at equivalent TO901317 dosage.

Figure 23:
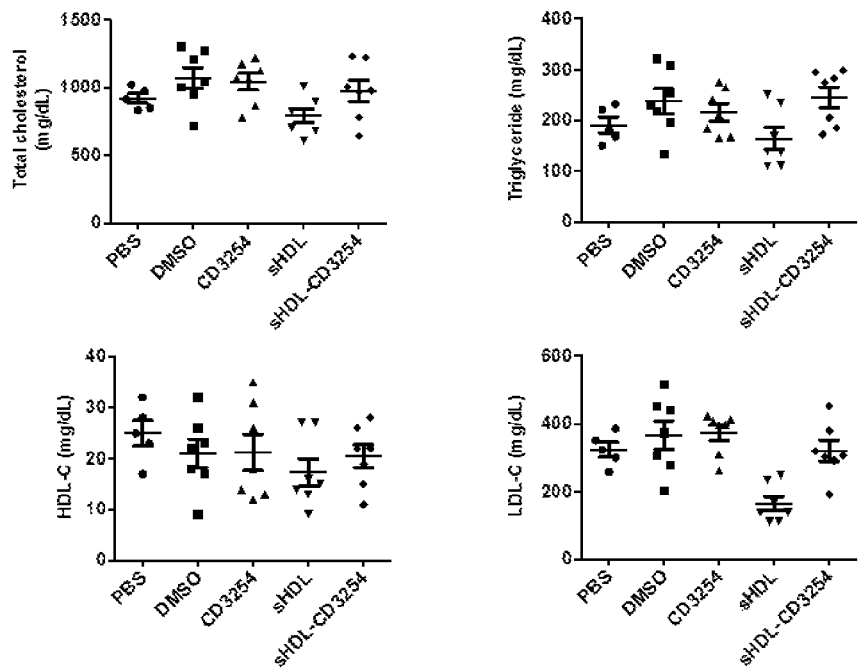
FIG. 23 shows RXR agonist treatment did not affect lipid profile in indicated groups of apoE-deficient mice.

FIG. 23 shows RXR agonist treatment did not affect lipid profile in indicated groups of apoE-deficient mice. Six-week-old male apoE$^{-/-}$ mice were place on HFD for 6 weeks to induce atherosclerotic lesion formation. Mice were randomized into 5 groups and received intraperitoneal injection with 1) PBS, 2) DMSO, 3) CD3254 dissolved in dimethyl sulfoxide (DMSO) (free CD3254, at 0.1 mg/kg), 4) sHDL nanoparticles, or 5) CD3254-encapsulated sHDL particles with a dose of 0.1 mg/kg of CD3254. The mice were treated for 6 weeks (three times per week, on Monday, Wednesday and Friday). Direct LDL-cholesterol (LDL-c), direct HDL-cholesterol (HDL-c), and enzymatic-colorimetric assays used to determine plasma total cholesterol (TC) and triglycerides (TG) were carried out at the Chemistry Laboratory of the Michigan Diabetes Research and Training Center.

Figure 24:
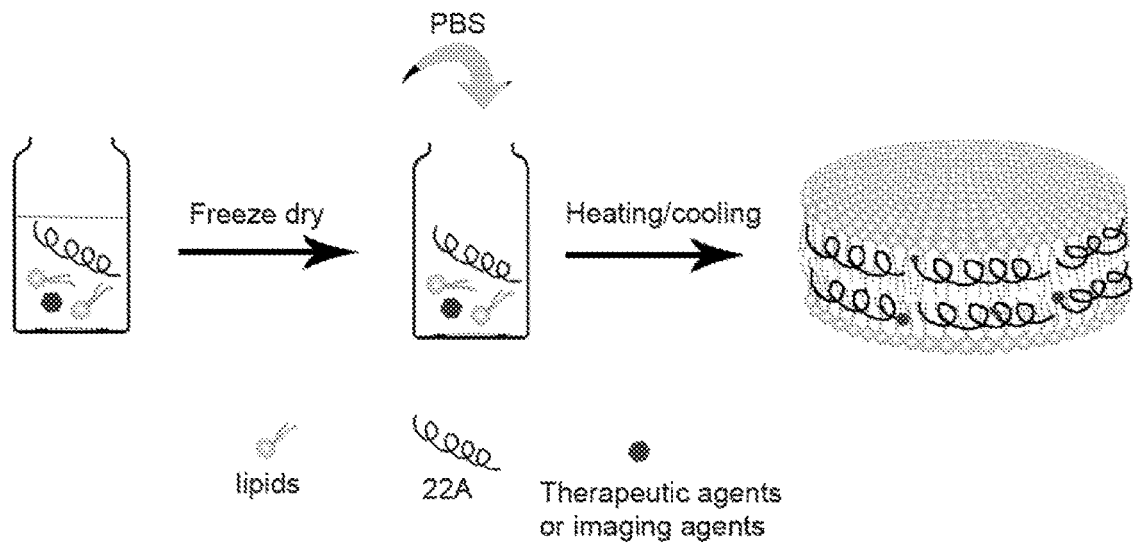
FIG. 24: Schematic for the preparation of drug-loaded sHDL. All components were dissolved in acetic acid and lyophilized, followed by hydration with PBS and thermal cycling to form drug-loaded sHDL.

FIG. 24: Schematic for the preparation of drug-loaded sHDL. All components were dissolved in acetic acid and lyophilized, followed by hydration with PBS and thermal cycling to form drug-loaded sHDL.

Figure 25:
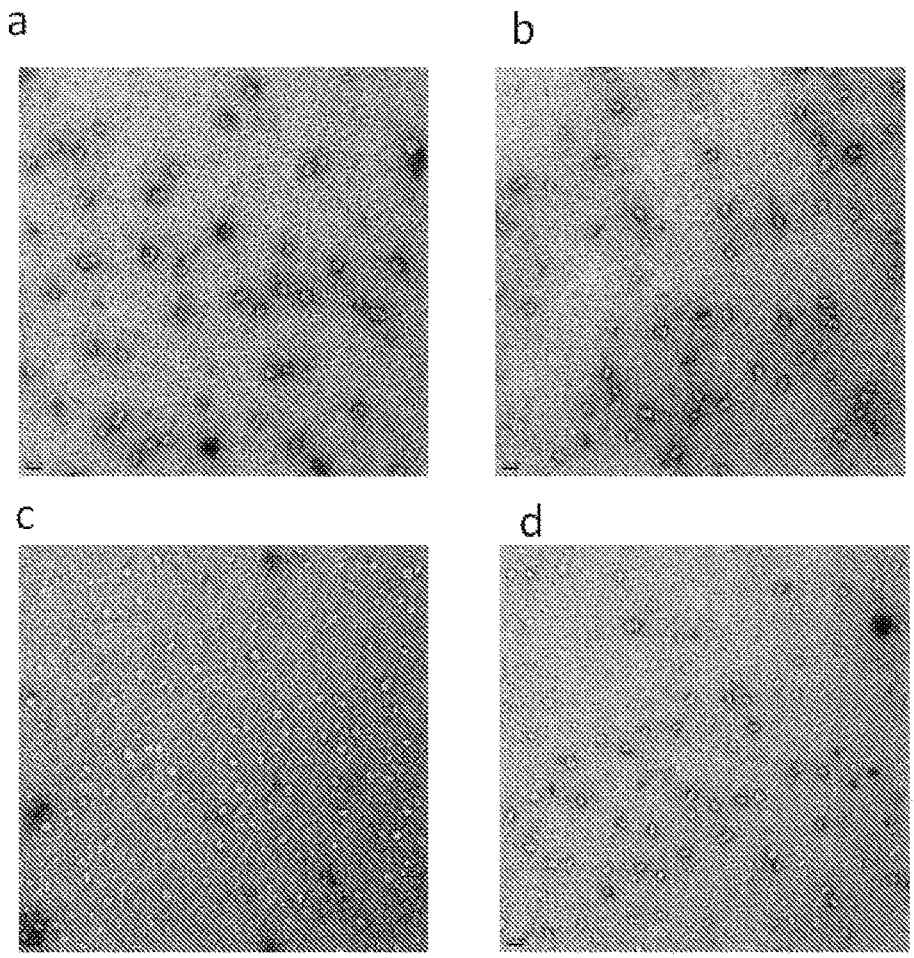
FIG. 25: Transmission electron microscopy of different sHDL nanoparticles. (a) Blank sHDL (DMPC:POPC:22A = 10 mg: 10 mg: 10 mg; (b) TO-loaded sHDL (DMPC:POPC: 22A: TO901317=10 mg: 10 mg: 10 mg:0.45 mg); (c) Blank sHDL (DMPC:22A=20 mg: 10 mg; (d) TO-loaded sHDL (DMPC:22A: TO901317=20 mg: 10 mg:0.45 mg).

FIG. 25: Transmission electron microscopy of different sHDL nanoparticles. (a) Blank sHDL (DMPC:POPC: 22A=10 mg: 10 mg: 10 mg; (b) TO-loaded sHDL (DMPC: POPC:22A: TO901317=10 mg: 10 mg: 10 mg:0.45 mg); (c) Blank sHDL (DMPC:22A=20 mg: 10 mg; (d) TO-loaded sHDL (DMPC:22A: TO901317=20 mg: 10 mg:0.45 mg).

Figure 26:
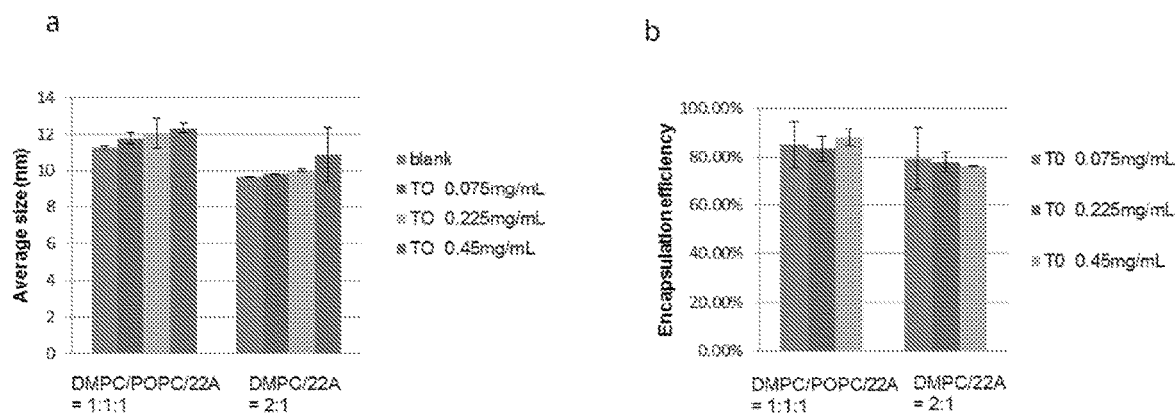
FIG. 26: Characterization of drug-loaded sHDL nanoparticles. (a) Sizes of different drug-loaded sHDL nanoparticles; (b) Encapsulation efficiency of different drug-loaded sHDL nanoparticles
Figure 27:
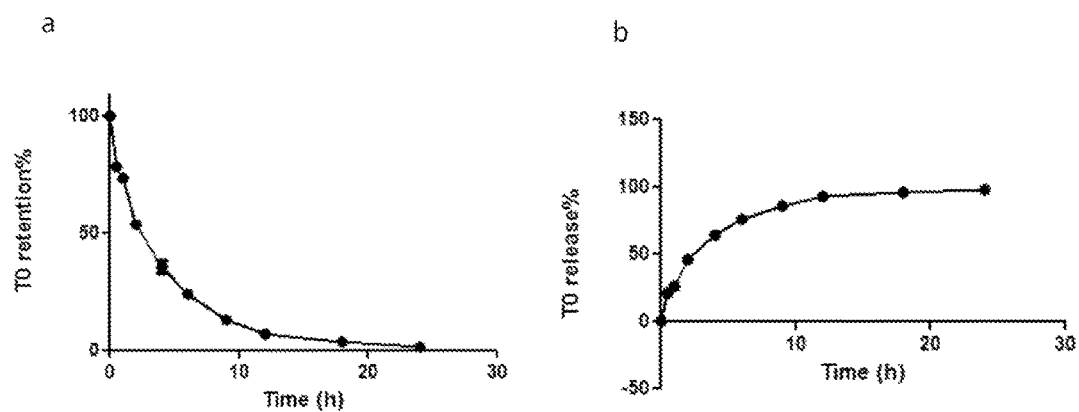
FIG. 27: Drug release from sHDL nanoparticles. (a) The percent of drug (TO901317) retained in sHDL nanoparticles over time. (b) The percent of drug (TO901317) released into the release medium over time.

FIG. 26: Characterization of drug-loaded sHDL nanoparticles. (a) Sizes of different drug-loaded sHDL nanoparticles; (b) Encapsulation efficiency of different drug-loaded sHDL nanoparticles FIG. 27: Drug release from sHDL nanoparticles. (a) The percent of drug (TO901317) retained in sHDL nanoparticles over time. (b) The percent of drug (TO901317) released into the release medium over time.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A composition comprising a synthetic high density lipoprotein(HDL)-therapeutic agent nanoparticle (sHDL-TA), wherein the sHDL comprises at least one HDL apolipoprotein and at least one phospholipid, wherein the therapeutic agent is between 0.01-20% by weight of the sHDL-TA, wherein the sHDL is between 80-99.99% by weight of the sHDL-TA, and wherein the HDL apolipoprotein is an apolipoprotein A-I (apo A-I) mimetic having the sequence PVLDLFRELLNELL-EALKQKLK (SEQ ID NO: 4).

2. The composition of claim 1, wherein the therapeutic agent is between 1-10% by weight of the sHDL-TA.

3. The composition of claim 1, wherein the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)- sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N -[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

4. The composition of claim 1, wherein the therapeutic agent is selected from the group consisting of
a liver X receptor (LXR) agonist,
a retinoid X receptor (RXR) agonist,
sphingosine-1-phosphate (S1P),
an angiotensin-converting enzyme (ACE) inhibitor selected from the group consisting of benazepril, enalapril, Lisinopril, perindopril, and Ramipril,
adenosine,
an alpha blocker,
an angtiotensin II receptor blocker (ARB),
an anticoagulant,
an antiplatelet agent,
a beta blocker,
a calcium channel blocker,
a diuretic,
an aldosterone blocker,
a loop diuretic,
a potassium-sparing diuretic,
a thiazide diuretic,
an inoptropic,
a bile acid sequestrant,
a fibrate,
a statin,
a selective cholesterol absorption inhibitor,
a potassium channel blocker,
a sodium channel blocker,
a thrombolytic agent,
a vasoconstrictor, and
a vasodilator.

5. The composition of claim 4,
wherein the liver X receptor agonist is selected from the group consisting of TO901317, ATI-111, LXR-623, XL-652, hypocholamide, GW3965, N,N-dimethyl-3beta -hydroxy-cholenamide (DMHCA), 22(R)-hydroxycholesterol, 24(S)-hydroxycholesterol, (−) anthrabenzoxocinone and (−)bischloroanthrabenzoxocinone ((−)-BABX);
wherein the retinoid X receptor agonist is selected from the group consisting of Bexarotene, CD3254, Docosahexaenoic acid, fluorobexarotene, isotretinoin, retinoic acid, SR11237, fenretinide, HX630, liarozole dihydrochloride, LG100754 and LG101506;

wherein the angiotensin-converting enzyme (ACE) inhibitor is selected from the group consisting of benazepril, enalapril, Lisinopril, perindopril, and Ramipril;

wherein the alpha blocker is selected from the group consisting of clonidine, guanabenz, labetalol, phenoxybenzamine, terazosin, doxazosin, guanfacine, methyldopa, and prazosin;

wherein the ARB is selected from the group consisting of candesartan, irbesartan, olmesartan medoxomil, telmisartan, eprosartan, losartan, tasosartan, and valsartan;

wherein the anticoagulant is selected from the group consisting of heparin fondaparinux, warfarin, ardeparin, enoxaparin, reviparin, dalteparin, nadroparin, and tinzaparin;

wherein the antiplatelet agent is selected from the group consisting of abciximab, clopidogrel, eptifibatide, ticlopidine, cilostazol, dipyridamole, sulfinpyrazone, and tirofiban;

wherein the beta blocker is selected from the group consisting of acebutolol, betaxolol, carteolol, metoprolol, penbutolol, propranolol, atenolol, bisoprolol, esmolol, nadolol, pindolol, and timolol;

wherein the calcium channel blocker is selected from the group consisting of amlopidine, felodipine, isradipine, nifedipine, verapamil, diltiazem, nicardipine, nimodipine, and nisoldipine, wherein the loop diuretic is selected from the group consisting of bumetanide, furosemide, ethacrynic acid, and torsemide;

wherein the thiazide diuretic is selected from the group consisting of chlorothiazide, chlorthalidone, hydrochlorothiazide, hydroflumethiazide, methyclothiazide, metolazone, polythiazide, quinethazone, and trichlormethiazide;

wherein the bile acid sequestrant is selected from the group consisting of cholestyramine, coletipol, and colesevelam;

wherein the fibrate is selected from the group consisting of clofibrate, gemfibrozil, and fenofibrate;

wherein the statin is selected from the group consisting of atorvastatinm, lovastatin, simvastatin. fluvastatin, and pravastatin;

wherein the selective cholesterol absorption inhibitor is ezetimibe;

wherein the potassium channel blocker is selected from the group consisting of amidarone, ibutilide, and dofetilide;

wherein the sodium channel blocker is selected from the group consisting of disopyramide, mexiletine, procainamide, quinidine, flecainide, moricizine, and propafenone;

wherein the thrombolytic agent is selected from the group consisting of alteplase, reteplase, tenecteplase, anistreplase, streptokinase, and urokinase; and wherein the vasodilator is selected from the group consisting of hydralazine, minoxidil, mecamylamine, isorbide dintrate, isorbide mononitrate, and nitroglycerin.

6. The composition of claim 1, wherein the average particle size of the sHDL-TA nanoparticle is between 6-20 nm.

7. A composition comprising a synthetic HDL-therapeutic agent-imaging agent nanoparticle (sHDL-TA/IA), wherein the sHDL comprises at least one HDL apolipoprotein and at least one phospholipid, wherein the HDL apolipoprotein is an apolipoprotein A-I (apo A-I) mimetic having the sequence PVLDLFRELLNELLEALKQKLK (SEQ ID NO: 4), wherein the combined weight of the therapeutic agent-imaging agent is between 0.01-20% by weight of the sHDL-TA/IA, and wherein the sHDL is between 80-99.99% by weight of the sHDL-TA/IA.

8. The composition of claim 7, wherein the therapeutic agent-imaging agent is between 1-10% by weight of the sHDL-TA/IA.

9. The composition of claim 7, wherein the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl) -sn-glycero-3-phosphoethanolamine-N-[4-(p-maleimidophenyl)butyramide], 1,2-di-hexadecanoyl-sn-glycero-3-phosphoethanolamine-N-[4-(p-maleimidophenyl)butyramide], 1,2-dihexadecanoyl-sn-glycero-3-phosphoethanolamine-N -[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

10. The composition of claim 7, wherein the therapeutic agent is selected from the group consisting of
a liver X receptor (LXR) agonist,
a retinoid X receptor (RXR) agonist,
sphingosine-1-phosphate (S1P),
an angiotensin-converting enzyme (ACE) inhibitor selected from the group consisting of benazepril, enalapril, Lisinopril, perindopril, and Ramipril,
adenosine,
an alpha blocker,
an angtiotensin II receptor blocker (ARB),
an anticoagulant,
an antiplatelet agent,
a beta blocker,
a calcium channel blocker,
a diuretic,
an aldosterone blocker,
a loop diuretic,
a potassium-sparing diuretic,
a thiazide diuretic,
an inoptropic,
a bile acid sequestrant,
a fibrate,
a statin,
a selective cholesterol absorption inhibitor,
a potassium channel blocker,
a sodium channel blocker,
a thrombolytic agent,
a vasoconstrictor, and
a vasodilator.

11. The composition of claim 10,
wherein the liver X receptor agonist is selected from the group consisting of TO901317, ATI-111, LXR-623, XL-652, hypocholamide, GW3965, N,N-dimethyl-3beta -hydroxy-cholenamide (DMHCA), 22(R)-hydroxycholesterol, 24(S)-hydroxycholesterol, (−) anthrabenzoxocinone and (−)bischloroanthrabenzoxocinone ((−)-BABX);
wherein the retinoid X receptor agonist is selected from the group consisting of Bexarotene, CD3254, Docosahexaenoic acid, fluorobexarotene, isotretinoin, retinoic acid, SR11237, fenretinide, HX630, liarozole dihydrochloride, LG100754 and LG101506;

wherein the angiotensin-converting enzyme (ACE) inhibitor is selected from the group consisting of benazepril, enalapril, Lisinopril, perindopril, and Ramipril;

wherein the alpha blocker is selected from the group consisting of clonidine, guanabenz, labetalol, phenoxybenzamine, terazosin, doxazosin, guanfacine, methyldopa, and prazosin;

wherein the ARB is selected from the group consisting of candesartan, irbesartan, olmesartan medoxomil, telmisartan, eprosartan, losartan, tasosartan, and valsartan;

wherein the anticoagulant is selected from the group consisting of heparin fondaparinux, warfarin, ardeparin, enoxaparin, reviparin, dalteparin, nadroparin, and tinzaparin;

wherein the antiplatelet agent is selected from the group consisting of abciximab, clopidogrel, eptifibatide, ticlopidine, cilostazol, dipyridamole, sulfinpyrazone, and tirofiban;

wherein the beta blocker is selected from the group consisting of acebutolol, betaxolol, carteolol, metoprolol, penbutolol, propranolol, atenolol, bisoprolol, esmolol, nadolol, pindolol, and timolol;

wherein the calcium channel blocker is selected from the group consisting of amlopidine, felodipine, isradipine, nifedipine, verapamil, diltiazem, nicardipine, nimodipine, and nisoldipine, wherein the loop diuretic is selected from the group consisting of bumetanide, furosemide, ethacrynic acid, and torsemide;

wherein the thiazide diuretic is selected from the group consisting of chlorothiazide, chlorthalidone, hydrochlorothiazide, hydroflumethiazide, methyclothiazide, metolazone, polythiazide, quinethazone, and trichlormethiazide;

wherein the bile acid sequestrant is selected from the group consisting of cholestyramine, coletipol, and colesevelam;

wherein the fibrate is selected from the group consisting of clofibrate, gemfibrozil, and fenofibrate;

wherein the statin is selected from the group consisting of atorvastatinm, lovastatin, simvastatin. fluvastatin, and pravastatin;

wherein the selective cholesterol absorption inhibitor is ezetimibe;

wherein the potassium channel blocker is selected from the group consisting of amidarone, ibutilide, and dofetilide;

wherein the sodium channel blocker is selected from the group consisting of disopyramide, mexiletine, procainamide, quinidine, flecainide, moricizine, and propafenone;

wherein the thrombolytic agent is selected from the group consisting of alteplase, reteplase, tenecteplase, anistreplase, streptokinase, and urokinase; and wherein the vasodilator is selected from the group consisting of hydralazine, minoxidil, mecamylamine, isorbide dintrate, isorbide mononitrate, and nitroglycerin.

12. The composition of claim 7, wherein the average particle size of the sHDL-TA/IA nanoparticle is between 6-20 nm.

13. The composition of claim 7, wherein the imaging agent is a lipophilic near infrared fluorescent dye or a nuclear imaging agent.

* * * * *

SEQUENCE LISTING

```
<160> NUMBER OF SEQ ID NOS: 335

<210> SEQ ID NO 1
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Z = Nal

<400> SEQUENCE: 1

Pro Val Leu Asp Leu Phe Arg Glu Leu Leu Asn Glu Leu Leu Glu Glx
1               5                   10                  15

Leu Lys Gln Lys Leu Lys
            20

<210> SEQ ID NO 2
<211> LENGTH: 23
```

```
<212> TYPE: PRT
<213> ORGANISM: Artificial sequence
<220> FEATURE:
<223> OTHER INFORMATION: synthetic

<400> SEQUENCE: 2

Gly Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 3
<211> LENGTH: 22
<212> TYPE: PRT
<213> ORGANISM: Artificial sequence
<220> FEATURE:
<223> OTHER INFORMATION: synthetic

<400> SEQUENCE: 3

Pro Val Leu Asp Leu Phe Arg Glu Leu Leu Asn Glu Leu Leu Glu Trp
1               5                   10                  15

Leu Lys Gln Lys Leu Lys
            20

<210> SEQ ID NO 4
<211> LENGTH: 22
<212> TYPE: PRT
<213> ORGANISM: Artificial sequence
<220> FEATURE:
<223> OTHER INFORMATION: synthetic

<400> SEQUENCE: 4

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 5
<211> LENGTH: 23
<212> TYPE: PRT
<213> ORGANISM: Artificial sequence
<220> FEATURE:
<223> OTHER INFORMATION: synthetic

<400> SEQUENCE: 5

Pro Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 6
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 6

Pro Val Leu Asp Leu Phe Arg Glu Leu Leu Asn Glu Xaa Leu Glu Ala
```

```
1               5                   10                  15
Leu Lys Gln Lys Leu Lys
            20

<210> SEQ ID NO 7
<211> LENGTH: 22
<212> TYPE: PRT
<213> ORGANISM: Artificial sequence
<220> FEATURE:
<223> OTHER INFORMATION: synthetic

<400> SEQUENCE: 7

Pro Val Leu Asp Leu Phe Lys Glu Leu Leu Asn Glu Leu Leu Glu Ala
1               5                   10                  15

Leu Lys Gln Lys Leu Lys
            20

<210> SEQ ID NO 8
<211> LENGTH: 22
<212> TYPE: PRT
<213> ORGANISM: Artificial sequence
<220> FEATURE:
<223> OTHER INFORMATION: synthetic

<400> SEQUENCE: 8

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 9
<211> LENGTH: 22
<212> TYPE: PRT
<213> ORGANISM: Artificial sequence
<220> FEATURE:
<223> OTHER INFORMATION: synthetic

<400> SEQUENCE: 9

Pro Val Leu Asp Leu Phe Arg Glu Leu Gly Asn Glu Leu Leu Glu Ala
1               5                   10                  15

Leu Lys Gln Lys Leu Lys
            20

<210> SEQ ID NO 10
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Z = Nal

<400> SEQUENCE: 10

Pro Val Leu Asp Leu Phe Arg Glu Leu Leu Asn Glu Leu Leu Glu Ala
1               5                   10                  15

Glx Lys Gln Lys Leu Lys
            20

<210> SEQ ID NO 11
<211> LENGTH: 22
<212> TYPE: PRT
<213> ORGANISM: Artificial sequence
<220> FEATURE:
<223> OTHER INFORMATION: synthetic
```

<400> SEQUENCE: 11

Pro Val Leu Asp Leu Phe Lys Glu Leu Leu Gln Glu Leu Leu Glu Ala
1               5                   10                  15

Leu Lys Gln Lys Leu Lys
            20

<210> SEQ ID NO 12
<211> LENGTH: 22
<212> TYPE: PRT
<213> ORGANISM: Artificial sequence
<220> FEATURE:
<223> OTHER INFORMATION: synthetic

<400> SEQUENCE: 12

Pro Val Leu Asp Leu Phe Arg Glu Leu Leu Asn Glu Leu Leu Glu Ala
1               5                   10                  15

Gly Lys Gln Lys Leu Lys
            20

<210> SEQ ID NO 13
<211> LENGTH: 22
<212> TYPE: PRT
<213> ORGANISM: Artificial sequence
<220> FEATURE:
<223> OTHER INFORMATION: synthetic

<400> SEQUENCE: 13

Gly Val Leu Asp Leu Phe Arg Glu Leu Leu Asn Glu Gly Leu Glu Ala
1               5                   10                  15

Leu Lys Gln Lys Leu Lys
            20

<210> SEQ ID NO 14
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 14

Pro Val Leu Asp Leu Phe Arg Glu Leu Leu Asn Glu Leu Leu Glu Ala
1               5                   10                  15

Leu Xaa Gln Xaa Leu Xaa
            20

<210> SEQ ID NO 15
<211> LENGTH: 22
<212> TYPE: PRT
<213> ORGANISM: Artificial sequence
<220> FEATURE:
<223> OTHER INFORMATION: synthetic

<400> SEQUENCE: 15

Pro Val Leu Asp Leu Phe Arg Glu Leu Trp Asn Glu Leu Leu Glu Ala
1               5                   10                  15

Leu Lys Gln Lys Leu Lys
            20

<210> SEQ ID NO 16
<211> LENGTH: 22
<212> TYPE: PRT
<213> ORGANISM: Artificial sequence
<220> FEATURE:
<223> OTHER INFORMATION: synthetic

<400> SEQUENCE: 16

Pro Val Leu Asp Leu Leu Arg Glu Leu Leu Asn Glu Leu Leu Glu Ala
1               5                   10                  15

Leu Lys Gln Lys Leu Lys
            20

<210> SEQ ID NO 17
<211> LENGTH: 22
<212> TYPE: PRT
<213> ORGANISM: Artificial sequence
<220> FEATURE:
<223> OTHER INFORMATION: synthetic

<400> SEQUENCE: 17

Pro Val Leu Glu Leu Phe Lys Glu Leu Leu Gln Glu Leu Leu Glu Ala
1               5                   10                  15

Leu Lys Gln Lys Leu Lys
            20

<210> SEQ ID NO 18
<211> LENGTH: 22
<212> TYPE: PRT
<213> ORGANISM: Artificial sequence
<220> FEATURE:
<223> OTHER INFORMATION: synthetic

<400> SEQUENCE: 18

Gly Val Leu Asp Leu Phe Arg Glu Leu Leu Asn Glu Leu Leu Glu Ala
1               5                   10                  15

Leu Lys Gln Lys Leu Lys
            20

<210> SEQ ID NO 19
<211> LENGTH: 22
<212> TYPE: PRT
<213> ORGANISM: Artificial sequence
<220> FEATURE:
<223> OTHER INFORMATION: synthetic

<400> SEQUENCE: 19

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 20
<211> LENGTH: 22
<212> TYPE: PRT
<213> ORGANISM: Artificial sequence
<220> FEATURE:

<223> OTHER INFORMATION: synthetic

<400> SEQUENCE: 20

Pro Val Leu Asp Leu Phe Arg Glu Gly Leu Asn Glu Leu Leu Glu Ala
1               5                   10                  15

Leu Lys Gln Lys Leu Lys
            20

<210> SEQ ID NO 21
<211> LENGTH: 22
<212> TYPE: PRT
<213> ORGANISM: Artificial sequence
<220> FEATURE:
<223> OTHER INFORMATION: synthetic

<400> SEQUENCE: 21

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 22
<211> LENGTH: 22
<212> TYPE: PRT
<213> ORGANISM: Artificial sequence
<220> FEATURE:
<223> OTHER INFORMATION: synthetic

<400> SEQUENCE: 22

Pro Val Leu Asp Leu Phe Arg Glu Leu Leu Asn Glu Leu Leu Glu Gly
1               5                   10                  15

Leu Lys Gln Lys Leu Lys
            20

<210> SEQ ID NO 23
<211> LENGTH: 22
<212> TYPE: PRT
<213> ORGANISM: Artificial sequence
<220> FEATURE:
<223> OTHER INFORMATION: synthetic

<400> SEQUENCE: 23

Pro Leu Leu Glu Leu Phe Lys Glu Leu Leu Gln Glu Leu Leu Glu Ala
1               5                   10                  15

Leu Lys Gln Lys Leu Lys
            20

<210> SEQ ID NO 24
<211> LENGTH: 22
<212> TYPE: PRT
<213> ORGANISM: Artificial sequence
<220> FEATURE:
<223> OTHER INFORMATION: synthetic

<400> SEQUENCE: 24

Pro Val Leu Asp Leu Phe Arg Glu Leu Leu Asn Glu Leu Leu Glu Ala
1               5                   10                  15

Leu Gln Lys Lys Leu Lys
            20

<210> SEQ ID NO 25
<211> LENGTH: 22
<212> TYPE: PRT
<213> ORGANISM: Artificial sequence

```
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 25

Pro Val Leu Asp Phe Phe Arg Glu Leu Leu Asn Glu Xaa Leu Glu Ala
1               5                   10                  15

Leu Lys Gln Lys Leu Lys
            20

<210> SEQ ID NO 26
<211> LENGTH: 22
<212> TYPE: PRT
<213> ORGANISM: Artificial sequence
<220> FEATURE:
<223> OTHER INFORMATION: synthetic

<400> SEQUENCE: 26

Pro Val Leu Asp Leu Phe Arg Glu Leu Leu Asn Glu Leu Leu Glu Leu
1               5                   10                  15

Leu Lys Gln Lys Leu Lys
            20

<210> SEQ ID NO 27
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Z = Nal

<400> SEQUENCE: 27

Pro Val Leu Asp Leu Phe Arg Glu Leu Leu Asn Glu Leu Glx Glu Ala
1               5                   10                  15

Leu Lys Gln Lys Leu Lys
            20

<210> SEQ ID NO 28
<211> LENGTH: 22
<212> TYPE: PRT
<213> ORGANISM: Artificial sequence
<220> FEATURE:
<223> OTHER INFORMATION: synthetic

<400> SEQUENCE: 28

Pro Val Leu Asp Leu Phe Arg Glu Leu Leu Asn Glu Leu Trp Glu Ala
1               5                   10                  15

Leu Lys Gln Lys Leu Lys
            20

<210> SEQ ID NO 29
<211> LENGTH: 22
<212> TYPE: PRT
<213> ORGANISM: Artificial sequence
<220> FEATURE:
<223> OTHER INFORMATION: synthetic

<400> SEQUENCE: 29
```

-continued

Ala Val Leu Asp Leu Phe Arg Glu Leu Leu Asn Glu Leu Leu Glu Ala
1               5                   10                  15

Leu Lys Gln Lys Leu Lys
            20

<210> SEQ ID NO 30
<211> LENGTH: 22
<212> TYPE: PRT
<213> ORGANISM: Artificial sequence
<220> FEATURE:
<223> OTHER INFORMATION: synthetic

<400> SEQUENCE: 30

Pro Val Leu Asp Leu Pro Arg Glu Leu Leu Asn Glu Leu Leu Glu Ala
1               5                   10                  15

Leu Lys Gln Lys Leu Lys
            20

<210> SEQ ID NO 31
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 31

Pro Val Leu Asp Leu Phe Leu Glu Leu Leu Asn Glu Xaa Leu Glu Ala
1               5                   10                  15

Leu Lys Gln Lys Leu Lys
            20

<210> SEQ ID NO 32
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (1)..(1)
<223> OTHER INFORMATION: Xaa can be any naturally occurring amino acid

<400> SEQUENCE: 32

Xaa Val Leu Asp Leu Phe Arg Glu Leu Leu Asn Glu Leu Leu Glu Ala
1               5                   10                  15

Leu Lys Gln Lys Leu Lys
            20

<210> SEQ ID NO 33
<211> LENGTH: 22
<212> TYPE: PRT
<213> ORGANISM: Artificial sequence
<220> FEATURE:
<223> OTHER INFORMATION: synthetic

<400> SEQUENCE: 33

Pro Val Leu Asp Leu Phe Arg Glu Lys Leu Asn Glu Leu Leu Glu Ala

```
1               5                   10                  15
Leu Lys Gln Lys Leu Lys
            20

<210> SEQ ID NO 34
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Z = Nal

<400> SEQUENCE: 34

Pro Val Leu Asp Glx Phe Arg Glu Leu Leu Asn Glu Leu Leu Glu Ala
1               5                   10                  15
Leu Lys Gln Lys Leu Lys
            20

<210> SEQ ID NO 35
<211> LENGTH: 22
<212> TYPE: PRT
<213> ORGANISM: Artificial sequence
<220> FEATURE:
<223> OTHER INFORMATION: synthetic

<400> SEQUENCE: 35

Pro Val Leu Asp Trp Phe Arg Glu Leu Leu Asn Glu Leu Leu Glu Ala
1               5                   10                  15
Leu Lys Gln Lys Leu Lys
            20

<210> SEQ ID NO 36
<211> LENGTH: 22
<212> TYPE: PRT
<213> ORGANISM: Artificial sequence
<220> FEATURE:
<223> OTHER INFORMATION: synthetic

<400> SEQUENCE: 36

Pro Leu Leu Glu Leu Leu Lys Glu Leu Leu Gln Glu Leu Leu Glu Ala
1               5                   10                  15
Leu Lys Gln Lys Leu Lys
            20

<210> SEQ ID NO 37
<211> LENGTH: 22
<212> TYPE: PRT
<213> ORGANISM: Artificial sequence
<220> FEATURE:
<223> OTHER INFORMATION: synthetic

<400> SEQUENCE: 37

Pro Val Leu Asp Leu Phe Arg Glu Trp Leu Asn Glu Leu Leu Glu Ala
1               5                   10                  15
Leu Lys Gln Lys Leu Lys
            20

<210> SEQ ID NO 38
<211> LENGTH: 22
<212> TYPE: PRT
<213> ORGANISM: Artificial sequence
<220> FEATURE:
<223> OTHER INFORMATION: synthetic
```

```
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 38

Pro Val Leu Asp Leu Phe Arg Glu Leu Leu Asn Glu Xaa Leu Glu Ala
1               5                   10                  15

Trp Lys Gln Lys Leu Lys
            20

<210> SEQ ID NO 39
<211> LENGTH: 22
<212> TYPE: PRT
<213> ORGANISM: Artificial sequence
<220> FEATURE:
<223> OTHER INFORMATION: synthetic

<400> SEQUENCE: 39

Pro Val Leu Asp Leu Phe Arg Glu Leu Leu Glu Glu Leu Leu Lys Ala
1               5                   10                  15

Leu Lys Lys Lys Leu Lys
            20

<210> SEQ ID NO 40
<211> LENGTH: 22
<212> TYPE: PRT
<213> ORGANISM: Artificial sequence
<220> FEATURE:
<223> OTHER INFORMATION: synthetic

<400> SEQUENCE: 40

Pro Val Leu Asp Leu Phe Asn Glu Leu Leu Arg Glu Leu Leu Glu Ala
1               5                   10                  15

Leu Gln Lys Lys Leu Lys
            20

<210> SEQ ID NO 41
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 41

Pro Val Leu Asp Leu Trp Arg Glu Leu Leu Asn Glu Xaa Leu Glu Ala
1               5                   10                  15

Leu Lys Gln Lys Leu Lys
            20

<210> SEQ ID NO 42
<211> LENGTH: 22
<212> TYPE: PRT
<213> ORGANISM: Artificial sequence
<220> FEATURE:
<223> OTHER INFORMATION: synthetic
<220> FEATURE:
```

```
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 42

Pro Val Leu Asp Glu Phe Arg Glu Lys Leu Asn Glu Xaa Trp Glu Ala
1               5                   10                  15

Leu Lys Gln Lys Leu Lys
            20

<210> SEQ ID NO 43
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 43

Pro Val Leu Asp Glu Phe Arg Glu Lys Leu Trp Glu Xaa Leu Glu Ala
1               5                   10                  15

Leu Lys Gln Lys Leu Lys
            20

<210> SEQ ID NO 44
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 44

Pro Val Leu Asp Glu Phe Arg Glu Lys Leu Asn Glu Xaa Leu Glu Ala
1               5                   10                  15

Leu Lys Gln Lys Leu Lys
            20

<210> SEQ ID NO 45
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 45

Pro Val Leu Asp Glu Phe Arg Glu Lys Leu Asn Glu Xaa Leu Glu Ala
```

Leu Lys Gln Lys Leu Lys
            20

<210> SEQ ID NO 46
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 46

Pro Val Leu Asp Leu Phe Arg Glu Lys Leu Asn Glu Xaa Leu Glu Ala
1               5                   10                  15

Leu Lys Gln Lys Leu Lys
            20

<210> SEQ ID NO 47
<211> LENGTH: 21
<212> TYPE: PRT
<213> ORGANISM: Artificial sequence
<220> FEATURE:
<223> OTHER INFORMATION: synthetic

<400> SEQUENCE: 47

Val Leu Asp Leu Phe Arg Glu Leu Leu Asn Glu Gly Leu Glu Ala Leu
1               5                   10                  15

Lys Gln Lys Leu Lys
            20

<210> SEQ ID NO 48
<211> LENGTH: 22
<212> TYPE: PRT
<213> ORGANISM: Artificial sequence
<220> FEATURE:
<223> OTHER INFORMATION: synthetic

<400> SEQUENCE: 48

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 49
<211> LENGTH: 22
<212> TYPE: PRT
<213> ORGANISM: Artificial sequence
<220> FEATURE:
<223> OTHER INFORMATION: synthetic

<400> SEQUENCE: 49

Pro Val Leu Asp Leu Phe Arg Asn Leu Leu Glu Lys Leu Leu Glu Ala
1               5                   10                  15

Leu Glu Gln Lys Leu Lys
            20

<210> SEQ ID NO 50
<211> LENGTH: 22

```
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 50

Pro Val Leu Asp Leu Phe Arg Glu Leu Leu Trp Glu Xaa Leu Glu Ala
1               5                   10                  15

Leu Lys Gln Lys Leu Lys
            20

<210> SEQ ID NO 51
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 51

Pro Val Leu Asp Leu Phe Trp Glu Leu Leu Asn Glu Xaa Leu Glu Ala
1               5                   10                  15

Leu Lys Gln Lys Leu Lys
            20

<210> SEQ ID NO 52
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: Xaa can be any naturally occurring amino acid

<400> SEQUENCE: 52

Pro Val Trp Asp Glu Phe Arg Glu Lys Leu Asn Glu Xaa Leu Glu Ala
1               5                   10                  15

Leu Lys Gln Lys Leu Lys
            20

<210> SEQ ID NO 53
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib

<400> SEQUENCE: 53

Val Val Leu Asp Leu Phe Arg Glu Leu Leu Asn Glu Leu Leu Glu Ala
1               5                   10                  15
```

Leu Lys Gln Lys Leu Lys
            20

<210> SEQ ID NO 54
<211> LENGTH: 22
<212> TYPE: PRT
<213> ORGANISM: Artificial sequence
<220> FEATURE:
<223> OTHER INFORMATION: synthetic

<400> SEQUENCE: 54

Pro Val Leu Asp Leu Phe Arg Glu Leu Leu Asn Glu Trp Leu Glu Ala
1               5                   10                  15

Leu Lys Gln Lys Leu Lys
            20

<210> SEQ ID NO 55
<211> LENGTH: 19
<212> TYPE: PRT
<213> ORGANISM: Artificial sequence
<220> FEATURE:
<223> OTHER INFORMATION: synthetic

<400> SEQUENCE: 55

Pro Leu Phe Arg Glu Leu Leu Asn Glu Leu Leu Glu Ala Leu Lys Gln
1               5                   10                  15

Lys Leu Lys

<210> SEQ ID NO 56
<211> LENGTH: 22
<212> TYPE: PRT
<213> ORGANISM: Artificial sequence
<220> FEATURE:
<223> OTHER INFORMATION: synthetic

<400> SEQUENCE: 56

Pro Val Leu Asp Leu Phe Arg Glu Leu Leu Asn Glu Leu Leu Glu Ala
1               5                   10                  15

Leu Lys Gln Lys Lys Lys
            20

<210> SEQ ID NO 57
<211> LENGTH: 22
<212> TYPE: PRT
<213> ORGANISM: Artificial sequence
<220> FEATURE:
<223> OTHER INFORMATION: synthetic

<400> SEQUENCE: 57

Pro Val Leu Asp Leu Phe Arg Asn Leu Leu Glu Glu Leu Leu Lys Ala
1               5                   10                  15

Leu Glu Gln Lys Leu Lys
            20

<210> SEQ ID NO 58
<211> LENGTH: 21
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)

<223> OTHER INFORMATION: Xaa can be any naturally occurring amino acid

<400> SEQUENCE: 58

Pro Val Leu Asp Glu Phe Arg Glu Lys Leu Asn Glu Xaa Leu Glu Ala
1               5                   10                  15

Leu Lys Gln Lys Leu
            20

<210> SEQ ID NO 59
<211> LENGTH: 22
<212> TYPE: PRT
<213> ORGANISM: Artificial sequence
<220> FEATURE:
<223> OTHER INFORMATION: synthetic

<400> SEQUENCE: 59

Leu Val Leu Asp Leu Phe Arg Glu Leu Leu Asn Glu Leu Leu Glu Ala
1               5                   10                  15

Leu Lys Gln Lys Leu Lys
            20

<210> SEQ ID NO 60
<211> LENGTH: 19
<212> TYPE: PRT
<213> ORGANISM: Artificial sequence
<220> FEATURE:
<223> OTHER INFORMATION: synthetic

<400> SEQUENCE: 60

Pro Val Leu Asp Leu Phe Arg Glu Leu Leu Asn Glu Leu Leu Glu Ala
1               5                   10                  15

Leu Lys Gln

<210> SEQ ID NO 61
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 61

Pro Val Leu Asp Glu Phe Arg Trp Lys Leu Asn Glu Xaa Leu Glu Ala
1               5                   10                  15

Leu Lys Gln Lys Leu Lys
            20

<210> SEQ ID NO 62
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

```
<400> SEQUENCE: 62

Pro Val Leu Asp Glu Trp Arg Glu Lys Leu Asn Glu Xaa Leu Glu Ala
1               5                   10                  15

Leu Lys Gln Lys Leu Lys
            20

<210> SEQ ID NO 63
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 63

Pro Val Leu Asp Phe Phe Arg Glu Lys Leu Asn Glu Xaa Leu Glu Ala
1               5                   10                  15

Leu Lys Gln Lys Leu Lys
            20

<210> SEQ ID NO 64
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 64

Pro Trp Leu Asp Glu Phe Arg Glu Lys Leu Asn Glu Xaa Leu Glu Ala
1               5                   10                  15

Leu Lys Gln Lys Leu Lys
            20

<210> SEQ ID NO 65
<211> LENGTH: 21
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (12)..(12)
<223> OTHER INFORMATION: Xaa can be any naturally occurring amino acid

<400> SEQUENCE: 65

Val Leu Asp Glu Phe Arg Glu Lys Leu Asn Glu Xaa Leu Glu Ala Leu
1               5                   10                  15

Lys Gln Lys Leu Lys
            20

<210> SEQ ID NO 66
```

```
<211> LENGTH: 22
<212> TYPE: PRT
<213> ORGANISM: Artificial sequence
<220> FEATURE:
<223> OTHER INFORMATION: synthetic

<400> SEQUENCE: 66

Pro Val Leu Asp Leu Phe Arg Asn Leu Leu Glu Glu Leu Leu Glu Ala
1               5                   10                  15

Leu Gln Lys Lys Leu Lys
            20

<210> SEQ ID NO 67
<211> LENGTH: 21
<212> TYPE: PRT
<213> ORGANISM: Artificial sequence
<220> FEATURE:
<223> OTHER INFORMATION: synthetic

<400> SEQUENCE: 67

Val Leu Asp Leu Phe Arg Glu Leu Leu Asn Glu Leu Leu Glu Ala Leu
1               5                   10                  15

Lys Gln Lys Leu Lys
            20

<210> SEQ ID NO 68
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 68

Pro Val Leu Asp Glu Phe Arg Glu Leu Leu Lys Glu Xaa Leu Glu Ala
1               5                   10                  15

Leu Lys Gln Lys Leu Lys
            20

<210> SEQ ID NO 69
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 69

Pro Val Leu Asp Glu Phe Arg Lys Lys Leu Asn Glu Xaa Leu Glu Ala
1               5                   10                  15

Leu Lys Gln Lys Leu Lys
            20

<210> SEQ ID NO 70
<211> LENGTH: 22
```

```
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 70

Pro Val Leu Asp Glu Phe Arg Glu Leu Leu Tyr Glu Xaa Leu Glu Ala
1               5                   10                  15

Leu Lys Gln Lys Leu Lys
            20

<210> SEQ ID NO 71
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (14)..(14)
<223> OTHER INFORMATION: Xaa can be any naturally occurring amino acid

<400> SEQUENCE: 71

Pro Val Leu Asp Glu Phe Arg Glu Lys Leu Asn Glu Leu Xaa Glu Ala
1               5                   10                  15

Leu Lys Gln Lys Leu Lys
            20

<210> SEQ ID NO 72
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 72

Pro Val Leu Asp Leu Phe Arg Glu Leu Leu Asn Glu Xaa Leu Trp Ala
1               5                   10                  15

Leu Lys Gln Lys Leu Lys
            20

<210> SEQ ID NO 73
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
```

<223> OTHER INFORMATION: Xaa can be any naturally occurring amino acid

<400> SEQUENCE: 73

Pro Val Leu Asp Glu Phe Trp Glu Lys Leu Asn Glu Xaa Leu Glu Ala
1               5                   10                  15

Leu Lys Gln Lys Leu Lys
            20

<210> SEQ ID NO 74
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 74

Pro Val Leu Asp Lys Phe Arg Glu Lys Leu Asn Glu Xaa Leu Glu Ala
1               5                   10                  15

Leu Lys Gln Lys Leu Lys
            20

<210> SEQ ID NO 75
<211> LENGTH: 22
<212> TYPE: PRT
<213> ORGANISM: Artificial sequence
<220> FEATURE:
<223> OTHER INFORMATION: synthetic

<400> SEQUENCE: 75

Pro Val Leu Asp Glu Phe Arg Glu Lys Leu Asn Glu Glu Leu Glu Ala
1               5                   10                  15

Leu Lys Gln Lys Leu Lys
            20

<210> SEQ ID NO 76
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 76

Pro Val Leu Asp Glu Phe Arg Glu Leu Leu Phe Glu Xaa Leu Glu Ala
1               5                   10                  15

Leu Lys Gln Lys Leu Lys
            20

<210> SEQ ID NO 77
<211> LENGTH: 22
<212> TYPE: PRT
<213> ORGANISM: Artificial sequence
<220> FEATURE:
<223> OTHER INFORMATION: synthetic

```
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 77

Pro Val Leu Asp Glu Phe Arg Glu Lys Leu Asn Lys Xaa Leu Glu Ala
1               5                   10                  15

Leu Lys Gln Lys Leu Lys
            20

<210> SEQ ID NO 78
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 78

Pro Val Leu Asp Glu Phe Arg Asp Lys Leu Asn Glu Xaa Leu Glu Ala
1               5                   10                  15

Leu Lys Gln Lys Leu Lys
            20

<210> SEQ ID NO 79
<211> LENGTH: 22
<212> TYPE: PRT
<213> ORGANISM: Artificial sequence
<220> FEATURE:
<223> OTHER INFORMATION: synthetic

<400> SEQUENCE: 79

Pro Val Leu Asp Glu Phe Arg Glu Leu Leu Asn Glu Leu Leu Glu Ala
1               5                   10                  15

Leu Lys Gln Lys Leu Lys
            20

<210> SEQ ID NO 80
<211> LENGTH: 22
<212> TYPE: PRT
<213> ORGANISM: Artificial sequence
<220> FEATURE:
<223> OTHER INFORMATION: synthetic

<400> SEQUENCE: 80

Pro Val Leu Asp Leu Phe Glu Arg Leu Leu Asn Glu Leu Leu Glu Ala
1               5                   10                  15

Leu Gln Lys Lys Leu Lys
            20

<210> SEQ ID NO 81
<211> LENGTH: 22
<212> TYPE: PRT
<213> ORGANISM: Artificial sequence
<220> FEATURE:
<223> OTHER INFORMATION: synthetic
<220> FEATURE:
```

```
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 81

Pro Val Leu Asp Glu Phe Arg Glu Lys Leu Asn Trp Xaa Leu Glu Ala
1               5                   10                  15

Leu Lys Gln Lys Leu Lys
            20

<210> SEQ ID NO 82
<211> LENGTH: 20
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (11)..(11)
<223> OTHER INFORMATION: Xaa can be any naturally occurring amino acid

<400> SEQUENCE: 82

Leu Asp Glu Phe Arg Glu Lys Leu Asn Glu Xaa Leu Glu Ala Leu Lys
1               5                   10                  15

Gln Lys Leu Lys
            20

<210> SEQ ID NO 83
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 83

Pro Val Leu Asp Glu Phe Arg Glu Lys Leu Asn Glu Xaa Leu Glu Ala
1               5                   10                  15

Leu Trp Gln Lys Leu Lys
            20

<210> SEQ ID NO 84
<211> LENGTH: 22
<212> TYPE: PRT
<213> ORGANISM: Artificial sequence
<220> FEATURE:
<223> OTHER INFORMATION: synthetic

<400> SEQUENCE: 84

Pro Val Leu Asp Glu Phe Arg Glu Lys Leu Asn Glu Leu Leu Glu Ala
1               5                   10                  15

Leu Lys Gln Lys Leu Lys
            20

<210> SEQ ID NO 85
```

```
<211> LENGTH: 21
<212> TYPE: PRT
<213> ORGANISM: Artificial sequence
<220> FEATURE:
<223> OTHER INFORMATION: synthetic

<400> SEQUENCE: 85

Pro Leu Asp Leu Phe Arg Glu Leu Leu Asn Glu Leu Leu Glu Ala Leu
1               5                   10                  15

Lys Gln Lys Leu Lys
            20

<210> SEQ ID NO 86
<211> LENGTH: 22
<212> TYPE: PRT
<213> ORGANISM: Artificial sequence
<220> FEATURE:
<223> OTHER INFORMATION: synthetic

<400> SEQUENCE: 86

Pro Val Leu Glu Leu Phe Glu Arg Leu Leu Asp Glu Leu Leu Asn Ala
1               5                   10                  15

Leu Gln Lys Lys Leu Lys
            20

<210> SEQ ID NO 87
<211> LENGTH: 22
<212> TYPE: PRT
<213> ORGANISM: Artificial sequence
<220> FEATURE:
<223> OTHER INFORMATION: synthetic

<400> SEQUENCE: 87

Pro Leu Leu Glu Leu Leu Lys Glu Leu Gln Glu Leu Leu Glu Ala
1               5                   10                  15

Leu Lys Gln Lys Leu Lys
            20

<210> SEQ ID NO 88
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 88

Pro Val Leu Asp Lys Phe Arg Glu Leu Leu Asn Glu Xaa Leu Glu Ala
1               5                   10                  15

Leu Lys Gln Lys Leu Lys
            20

<210> SEQ ID NO 89
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
```

```
<220> FEATURE:
<221> NAME/KEY: misc_feature
<222> LOCATION: (13)..(13)
<223> OTHER INFORMATION: Xaa can be any naturally occurring amino acid

<400> SEQUENCE: 89

Pro Val Leu Asp Glu Phe Arg Glu Lys Leu Asn Glu Xaa Leu Trp Ala
1               5                   10                  15

Leu Lys Gln Lys Leu Lys
            20

<210> SEQ ID NO 90
<211> LENGTH: 19
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (10)..(10)
<223> OTHER INFORMATION: Xaa can be any naturally occurring amino acid

<400> SEQUENCE: 90

Asp Glu Phe Arg Glu Lys Leu Asn Glu Xaa Leu Glu Ala Leu Lys Gln
1               5                   10                  15

Lys Leu Lys

<210> SEQ ID NO 91
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 91

Pro Val Leu Asp Glu Phe Arg Glu Leu Leu Asn Glu Xaa Leu Glu Ala
1               5                   10                  15

Leu Lys Gln Lys Leu Lys
            20

<210> SEQ ID NO 92
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 92

Pro Val Leu Asp Glu Phe Arg Glu Leu Tyr Asn Glu Xaa Leu Glu Ala
1               5                   10                  15

Leu Lys Gln Lys Leu Lys
```

```
<210> SEQ ID NO 93
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 93

Pro Val Leu Asp Glu Phe Arg Glu Lys Leu Asn Glu Xaa Leu Lys Ala
1               5                   10                  15

Leu Lys Gln Lys Leu Lys
            20

<210> SEQ ID NO 94
<211> LENGTH: 22
<212> TYPE: PRT
<213> ORGANISM: Artificial sequence
<220> FEATURE:
<223> OTHER INFORMATION: synthetic

<400> SEQUENCE: 94

Pro Val Leu Asp Glu Phe Arg Glu Lys Leu Asn Glu Ala Leu Glu Ala
1               5                   10                  15

Leu Lys Gln Lys Leu Lys
            20

<210> SEQ ID NO 95
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 95

Pro Val Leu Asp Leu Phe Arg Glu Leu Leu Asn Leu Xaa Leu Glu Ala
1               5                   10                  15

Leu Lys Gln Lys Leu Lys
            20

<210> SEQ ID NO 96
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid
```

```
<400> SEQUENCE: 96

Pro Val Leu Asp Leu Phe Arg Glu Leu Leu Asn Glu Xaa Leu Glu Ala
1               5                   10                  15

Leu Lys Gln Lys Leu Lys
            20

<210> SEQ ID NO 97
<211> LENGTH: 15
<212> TYPE: PRT
<213> ORGANISM: Artificial sequence
<220> FEATURE:
<223> OTHER INFORMATION: synthetic

<400> SEQUENCE: 97

Pro Val Leu Asp Leu Phe Arg Glu Leu Leu Asn Glu Leu Leu Glu
1               5                   10                  15

<210> SEQ ID NO 98
<211> LENGTH: 22
<212> TYPE: PRT
<213> ORGANISM: Artificial sequence
<220> FEATURE:
<223> OTHER INFORMATION: synthetic

<400> SEQUENCE: 98

Pro Val Leu Asp Leu Phe Arg Glu Leu Leu Asn Glu Glu Leu Glu Ala
1               5                   10                  15

Leu Lys Gln Lys Leu Lys
            20

<210> SEQ ID NO 99
<211> LENGTH: 22
<212> TYPE: PRT
<213> ORGANISM: Artificial sequence
<220> FEATURE:
<223> OTHER INFORMATION: synthetic

<400> SEQUENCE: 99

Lys Leu Lys Gln Lys Leu Ala Glu Leu Leu Glu Asn Leu Leu Glu Arg
1               5                   10                  15

Phe Leu Asp Leu Val Pro
            20

<210> SEQ ID NO 100
<211> LENGTH: 22
<212> TYPE: PRT
<213> ORGANISM: Artificial sequence
<220> FEATURE:
<223> OTHER INFORMATION: synthetic

<400> SEQUENCE: 100

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 101
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
```

```
<220> FEATURE:
<221> NAME/KEY: misc_feature
<222> LOCATION: (13)..(13)
<223> OTHER INFORMATION: Xaa can be any naturally occurring amino acid

<400> SEQUENCE: 101

Pro Val Leu Asp Leu Phe Arg Glu Leu Leu Asn Trp Xaa Leu Glu Ala
1               5                   10                  15

Leu Lys Gln Lys Leu Lys
            20

<210> SEQ ID NO 102
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 102

Pro Val Leu Asp Leu Phe Arg Glu Leu Leu Asn Leu Xaa Leu Glu Ala
1               5                   10                  15

Leu Lys Glu Lys Leu Lys
            20

<210> SEQ ID NO 103
<211> LENGTH: 22
<212> TYPE: PRT
<213> ORGANISM: Artificial sequence
<220> FEATURE:
<223> OTHER INFORMATION: synthetic

<400> SEQUENCE: 103

Pro Val Leu Asp Glu Phe Arg Glu Leu Leu Asn Glu Glu Leu Glu Ala
1               5                   10                  15

Leu Lys Gln Lys Leu Lys
            20

<210> SEQ ID NO 104
<211> LENGTH: 15
<212> TYPE: PRT
<213> ORGANISM: Artificial sequence
<220> FEATURE:
<223> OTHER INFORMATION: synthetic

<400> SEQUENCE: 104

Pro Leu Leu Asn Glu Leu Leu Glu Ala Leu Lys Gln Lys Leu Lys
1               5                   10                  15

<210> SEQ ID NO 105
<211> LENGTH: 22
<212> TYPE: PRT
<213> ORGANISM: Artificial sequence
<220> FEATURE:
<223> OTHER INFORMATION: synthetic

<400> SEQUENCE: 105

Pro Ala Ala Asp Ala Phe Arg Glu Ala Ala Asn Glu Ala Ala Glu Ala
1               5                   10                  15

Ala Lys Gln Lys Ala Lys
```

20

<210> SEQ ID NO 106
<211> LENGTH: 22
<212> TYPE: PRT
<213> ORGANISM: Artificial sequence
<220> FEATURE:
<223> OTHER INFORMATION: synthetic

<400> SEQUENCE: 106

Pro Val Leu Asp Leu Phe Arg Glu Lys Leu Asn Glu Glu Leu Glu Ala
1               5                   10                  15

Leu Lys Gln Lys Leu Lys
            20

<210> SEQ ID NO 107
<211> LENGTH: 22
<212> TYPE: PRT
<213> ORGANISM: Artificial sequence
<220> FEATURE:
<223> OTHER INFORMATION: synthetic

<400> SEQUENCE: 107

Lys Leu Lys Gln Lys Leu Ala Glu Leu Leu Glu Asn Leu Leu Glu Arg
1               5                   10                  15

Phe Leu Asp Leu Val Pro
            20

<210> SEQ ID NO 108
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 108

Pro Val Leu Asp Leu Phe Arg Trp Leu Leu Asn Glu Xaa Leu Glu Ala
1               5                   10                  15

Leu Lys Gln Lys Leu Lys
            20

<210> SEQ ID NO 109
<211> LENGTH: 22
<212> TYPE: PRT
<213> ORGANISM: Artificial sequence
<220> FEATURE:
<223> OTHER INFORMATION: synthetic

<400> SEQUENCE: 109

Pro Val Leu Asp Glu Phe Arg Glu Lys Leu Asn Glu Arg Leu Glu Ala
1               5                   10                  15

Leu Lys Gln Lys Leu Lys
            20

<210> SEQ ID NO 110
<211> LENGTH: 22
<212> TYPE: PRT
<213> ORGANISM: Artificial sequence
<220> FEATURE:

<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(14)
<223> OTHER INFORMATION: Xaa can be any naturally occurring amino acid

<400> SEQUENCE: 110

Pro Val Leu Asp Glu Phe Arg Glu Lys Leu Asn Glu Xaa Xaa Glu Ala
1               5                   10                  15

Leu Lys Gln Lys Leu Lys
            20

<210> SEQ ID NO 111
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 111

Pro Val Leu Asp Glu Phe Arg Glu Lys Leu Trp Glu Xaa Trp Glu Ala
1               5                   10                  15

Leu Lys Gln Lys Leu Lys
            20

<210> SEQ ID NO 112
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 112

Pro Val Leu Asp Glu Phe Arg Glu Lys Leu Asn Glu Xaa Ser Glu Ala
1               5                   10                  15

Leu Lys Gln Lys Leu Lys
            20

<210> SEQ ID NO 113
<211> LENGTH: 22
<212> TYPE: PRT
<213> ORGANISM: Artificial sequence
<220> FEATURE:
<223> OTHER INFORMATION: synthetic

<400> SEQUENCE: 113

Pro Val Leu Asp Glu Phe Arg Glu Lys Leu Asn Glu Pro Leu Glu Ala
1               5                   10                  15

Leu Lys Gln Lys Leu Lys
            20

```
<210> SEQ ID NO 114
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 114

Pro Val Leu Asp Glu Phe Arg Glu Lys Leu Asn Glu Xaa Met Glu Ala
1               5                   10                  15

Leu Lys Gln Lys Leu Lys
            20

<210> SEQ ID NO 115
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 115

Pro Lys Leu Asp Glu Phe Arg Glu Lys Leu Asn Glu Xaa Leu Glu Ala
1               5                   10                  15

Leu Lys Gln Lys Leu Lys
            20

<210> SEQ ID NO 116
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 116

Pro His Leu Asp Glu Phe Arg Glu Lys Leu Asn Glu Xaa Leu Glu Ala
1               5                   10                  15

Leu Lys Gln Lys Leu Lys
            20

<210> SEQ ID NO 117
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
```

```
<220> FEATURE:
<221> NAME/KEY: misc_feature
<222> LOCATION: (13)..(13)
<223> OTHER INFORMATION: Xaa can be any naturally occurring amino acid

<400> SEQUENCE: 117

Pro Glu Leu Asp Glu Phe Arg Glu Lys Leu Asn Glu Xaa Leu Glu Ala
1               5                   10                  15

Leu Lys Gln Lys Leu Lys
            20

<210> SEQ ID NO 118
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 118

Pro Val Leu Asp Glu Phe Arg Glu Lys Leu Asn Glu Xaa Leu Glu Ala
1               5                   10                  15

Leu Glu Gln Lys Leu Lys
            20

<210> SEQ ID NO 119
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (17)..(17)
<223> OTHER INFORMATION: Xaa can be any naturally occurring amino acid

<400> SEQUENCE: 119

Pro Val Leu Asp Glu Phe Arg Glu Lys Leu Asn Glu Glu Leu Glu Ala
1               5                   10                  15

Xaa Lys Gln Lys Leu Lys
            20

<210> SEQ ID NO 120
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (16)..(16)
<223> OTHER INFORMATION: Xaa can be any naturally occurring amino acid

<400> SEQUENCE: 120

Pro Val Leu Asp Glu Phe Arg Glu Lys Leu Asn Glu Glu Leu Glu Xaa
1               5                   10                  15
```

Leu Lys Gln Lys Leu Lys
            20

<210> SEQ ID NO 121
<211> LENGTH: 22
<212> TYPE: PRT
<213> ORGANISM: Artificial sequence
<220> FEATURE:
<223> OTHER INFORMATION: synthetic

<400> SEQUENCE: 121

Pro Val Leu Asp Glu Phe Arg Glu Lys Leu Asn Glu Glu Leu Glu Ala
1               5                   10                  15

Leu Trp Gln Lys Leu Lys
            20

<210> SEQ ID NO 122
<211> LENGTH: 22
<212> TYPE: PRT
<213> ORGANISM: Artificial sequence
<220> FEATURE:
<223> OTHER INFORMATION: synthetic

<400> SEQUENCE: 122

Pro Val Leu Asp Glu Phe Arg Glu Lys Leu Asn Glu Glu Leu Glu Trp
1               5                   10                  15

Leu Lys Gln Lys Leu Lys
            20

<210> SEQ ID NO 123
<211> LENGTH: 22
<212> TYPE: PRT
<213> ORGANISM: Artificial sequence
<220> FEATURE:
<223> OTHER INFORMATION: synthetic

<400> SEQUENCE: 123

Gln Val Leu Asp Leu Phe Arg Glu Leu Leu Asn Glu Leu Leu Glu Ala
1               5                   10                  15

Leu Lys Gln Lys Leu Lys
            20

<210> SEQ ID NO 124
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 124

```
Pro Val Leu Asp Leu Phe Xaa Glu Leu Leu Asn Glu Leu Leu Glu Ala
1               5                   10                  15

Leu Xaa Gln Xaa Leu Xaa
            20
```

<210> SEQ ID NO 125
<211> LENGTH: 22
<212> TYPE: PRT
<213> ORGANISM: Artificial sequence
<220> FEATURE:
<223> OTHER INFORMATION: synthetic

<400> SEQUENCE: 125

```
Asn Val Leu Asp Leu Phe Arg Glu Leu Leu Asn Glu Leu Leu Glu Ala
1               5                   10                  15

Leu Lys Gln Lys Leu Lys
            20
```

<210> SEQ ID NO 126
<211> LENGTH: 22
<212> TYPE: PRT
<213> ORGANISM: Artificial sequence
<220> FEATURE:
<223> OTHER INFORMATION: synthetic

<400> SEQUENCE: 126

```
Pro Val Leu Asp Leu Phe Arg Glu Leu Leu Asn Glu Leu Gly Glu Ala
1               5                   10                  15

Leu Lys Gln Lys Leu Lys
            20
```

<210> SEQ ID NO 127
<211> LENGTH: 22
<212> TYPE: PRT
<213> ORGANISM: Artificial sequence
<220> FEATURE:
<223> OTHER INFORMATION: synthetic

<400> SEQUENCE: 127

```
Pro Val Leu Asp Leu Phe Arg Glu Leu Leu Asn Glu Leu Leu Glu Leu
1               5                   10                  15

Leu Lys Gln Lys Leu Lys
            20
```

<210> SEQ ID NO 128
<211> LENGTH: 22
<212> TYPE: PRT
<213> ORGANISM: Artificial sequence
<220> FEATURE:
<223> OTHER INFORMATION: synthetic

<400> SEQUENCE: 128

```
Pro Val Leu Asp Leu Phe Arg Glu Leu Leu Asn Glu Leu Leu Glu Phe
1               5                   10                  15

Leu Lys Gln Lys Leu Lys
            20
```

<210> SEQ ID NO 129
<211> LENGTH: 22
<212> TYPE: PRT
<213> ORGANISM: Artificial sequence
<220> FEATURE:
<223> OTHER INFORMATION: synthetic -continued

```
<400> SEQUENCE: 129

Pro Val Leu Glu Leu Phe Asn Asp Leu Leu Arg Glu Leu Leu Glu Ala
1               5                   10                  15

Leu Gln Lys Lys Leu Lys
            20

<210> SEQ ID NO 130
<211> LENGTH: 22
<212> TYPE: PRT
<213> ORGANISM: Artificial sequence
<220> FEATURE:
<223> OTHER INFORMATION: synthetic

<400> SEQUENCE: 130

Pro Val Leu Glu Leu Phe Asn Asp Leu Leu Arg Glu Leu Leu Glu Ala
1               5                   10                  15

Leu Lys Gln Lys Leu Lys
            20

<210> SEQ ID NO 131
<211> LENGTH: 22
<212> TYPE: PRT
<213> ORGANISM: Artificial sequence
<220> FEATURE:
<223> OTHER INFORMATION: synthetic

<400> SEQUENCE: 131

Pro Val Leu Glu Leu Phe Lys Glu Leu Leu Asn Glu Leu Leu Asp Ala
1               5                   10                  15

Leu Arg Gln Lys Leu Lys
            20

<210> SEQ ID NO 132
<211> LENGTH: 22
<212> TYPE: PRT
<213> ORGANISM: Artificial sequence
<220> FEATURE:
<223> OTHER INFORMATION: synthetic

<400> SEQUENCE: 132

Pro Val Leu Asp Leu Phe Arg Glu Leu Leu Glu Asn Leu Leu Glu Ala
1               5                   10                  15

Leu Gln Lys Lys Leu Lys
            20

<210> SEQ ID NO 133
<211> LENGTH: 22
<212> TYPE: PRT
<213> ORGANISM: Artificial sequence
<220> FEATURE:
<223> OTHER INFORMATION: synthetic

<400> SEQUENCE: 133

Pro Val Leu Glu Leu Phe Glu Arg Leu Leu Glu Asp Leu Leu Gln Ala
1               5                   10                  15

Leu Asn Lys Lys Leu Lys
            20

<210> SEQ ID NO 134
<211> LENGTH: 22
<212> TYPE: PRT
<213> ORGANISM: Artificial sequence
<220> FEATURE:
<223> OTHER INFORMATION: synthetic
```

```
<220> FEATURE:
<221> NAME/KEY: misc_feature
<223> OTHER INFORMATION: Xaa = Orn
<220> FEATURE:
<221> NAME/KEY: misc_feature
<222> LOCATION: (19)..(19)
<223> OTHER INFORMATION: Xaa can be any naturally occurring amino acid

<400> SEQUENCE: 134

Pro Val Leu Glu Leu Phe Glu Arg Leu Leu Glu Asp Leu Leu Lys Ala
1               5                   10                  15

Leu Asn Xaa Lys Leu Lys
            20

<210> SEQ ID NO 135
<211> LENGTH: 22
<212> TYPE: PRT
<213> ORGANISM: Artificial sequence
<220> FEATURE:
<223> OTHER INFORMATION: synthetic

<400> SEQUENCE: 135

Asp Val Leu Asp Leu Phe Arg Glu Leu Leu Asn Glu Leu Leu Glu Ala
1               5                   10                  15

Leu Lys Gln Lys Leu Lys
            20

<210> SEQ ID NO 136
<211> LENGTH: 22
<212> TYPE: PRT
<213> ORGANISM: Artificial sequence
<220> FEATURE:
<223> OTHER INFORMATION: synthetic

<400> SEQUENCE: 136

Pro Ala Leu Glu Leu Phe Lys Asp Leu Leu Gln Glu Leu Leu Glu Ala
1               5                   10                  15

Leu Lys Gln Lys Leu Lys
            20

<210> SEQ ID NO 137
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Z = Nal

<400> SEQUENCE: 137

Pro Val Leu Asp Leu Phe Arg Glu Leu Leu Asn Glu Gly Leu Glu Ala
1               5                   10                  15

Glx Lys Gln Lys Leu Lys
            20

<210> SEQ ID NO 138
<211> LENGTH: 22
<212> TYPE: PRT
<213> ORGANISM: Artificial sequence
<220> FEATURE:
<223> OTHER INFORMATION: synthetic

<400> SEQUENCE: 138

Pro Val Leu Asp Leu Phe Arg Glu Leu Leu Asn Glu Gly Leu Glu Trp
1               5                   10                  15
```

```
-continued

Leu Lys Gln Lys Leu Lys
        20

<210> SEQ ID NO 139
<211> LENGTH: 22
<212> TYPE: PRT
<213> ORGANISM: Artificial sequence
<220> FEATURE:
<223> OTHER INFORMATION: synthetic

<400> SEQUENCE: 139

Pro Val Leu Asp Leu Phe Arg Glu Leu Trp Asn Glu Gly Leu Glu Ala
1               5                   10                  15

Leu Lys Gln Lys Leu Lys
        20

<210> SEQ ID NO 140
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 140

Pro Val Leu Asp Leu Phe Arg Glu Leu Leu Asn Glu Gly Leu Glu Ala
1               5                   10                  15

Leu Xaa Gln Xaa Leu Xaa
        20

<210> SEQ ID NO 141
<211> LENGTH: 22
<212> TYPE: PRT
<213> ORGANISM: Artificial sequence
<220> FEATURE:
<223> OTHER INFORMATION: synthetic

<400> SEQUENCE: 141

Pro Val Leu Asp Phe Phe Arg Glu Leu Leu Asn Glu Gly Leu Glu Ala
1               5                   10                  15

Leu Lys Gln Lys Leu Lys
        20

<210> SEQ ID NO 142
<211> LENGTH: 22
<212> TYPE: PRT
<213> ORGANISM: Artificial sequence
<220> FEATURE:
<223> OTHER INFORMATION: synthetic

<400> SEQUENCE: 142

Pro Val Leu Glu Leu Phe Arg Glu Leu Leu Asn Glu Gly Leu Glu Ala
1               5                   10                  15
```

Leu Lys Gln Lys Leu Lys
            20

<210> SEQ ID NO 143
<211> LENGTH: 22
<212> TYPE: PRT
<213> ORGANISM: Artificial sequence
<220> FEATURE:
<223> OTHER INFORMATION: synthetic

<400> SEQUENCE: 143

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 144
<211> LENGTH: 22
<212> TYPE: PRT
<213> ORGANISM: Artificial sequence
<220> FEATURE:
<223> OTHER INFORMATION: synthetic

<400> SEQUENCE: 144

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 145
<211> LENGTH: 22
<212> TYPE: PRT
<213> ORGANISM: Artificial sequence
<220> FEATURE:
<223> OTHER INFORMATION: synthetic

<400> SEQUENCE: 145

Gly Val Leu Glu Leu Phe Glu Asn Leu Leu Glu Arg Leu Leu Asp Ala
1               5                   10                  15

Leu Gln Lys Lys Leu Lys
            20

<210> SEQ ID NO 146
<211> LENGTH: 22
<212> TYPE: PRT
<213> ORGANISM: Artificial sequence
<220> FEATURE:
<223> OTHER INFORMATION: synthetic

<400> SEQUENCE: 146

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 147
<211> LENGTH: 22
<212> TYPE: PRT
<213> ORGANISM: Artificial sequence
<220> FEATURE:
<223> OTHER INFORMATION: synthetic

<400> SEQUENCE: 147

Pro Val Leu Glu Leu Phe Glu Asn Leu Leu Glu Arg Leu Phe Asp Ala

```
1               5                   10                  15
Leu Gln Lys Lys Leu Lys
            20

<210> SEQ ID NO 148
<211> LENGTH: 22
<212> TYPE: PRT
<213> ORGANISM: Artificial sequence
<220> FEATURE:
<223> OTHER INFORMATION: synthetic

<400> SEQUENCE: 148

Pro Val Leu Glu Leu Phe Glu Asn Leu Leu Glu Arg Leu Gly Asp Ala
1               5                   10                  15

Leu Gln Lys Lys Leu Lys
            20

<210> SEQ ID NO 149
<211> LENGTH: 22
<212> TYPE: PRT
<213> ORGANISM: Artificial sequence
<220> FEATURE:
<223> OTHER INFORMATION: synthetic

<400> SEQUENCE: 149

Pro Val Leu Glu Leu Phe Glu Asn Leu Trp Glu Arg Leu Leu Asp Ala
1               5                   10                  15

Leu Gln Lys Lys Leu Lys
            20

<210> SEQ ID NO 150
<211> LENGTH: 22
<212> TYPE: PRT
<213> ORGANISM: Artificial sequence
<220> FEATURE:
<223> OTHER INFORMATION: synthetic

<400> SEQUENCE: 150

Pro Leu Leu Glu Leu Phe Glu Asn Leu Leu Glu Arg Leu Leu Asp Ala
1               5                   10                  15

Leu Gln Lys Lys Leu Lys
            20

<210> SEQ ID NO 151
<211> LENGTH: 22
<212> TYPE: PRT
<213> ORGANISM: Artificial sequence
<220> FEATURE:
<223> OTHER INFORMATION: synthetic

<400> SEQUENCE: 151

Pro Val Leu Glu Leu Phe Glu Asn Leu Gly Glu Arg Leu Leu Asp Ala
1               5                   10                  15

Leu Gln Lys Lys Leu Lys
            20

<210> SEQ ID NO 152
<211> LENGTH: 22
<212> TYPE: PRT
<213> ORGANISM: Artificial sequence
<220> FEATURE:
<223> OTHER INFORMATION: synthetic

<400> SEQUENCE: 152
```

Pro Val Phe Glu Leu Phe Glu Asn Leu Leu Glu Arg Leu Leu Asp Ala
1               5                   10                  15

Leu Gln Lys Lys Leu Lys
            20

<210> SEQ ID NO 153
<211> LENGTH: 22
<212> TYPE: PRT
<213> ORGANISM: Artificial sequence
<220> FEATURE:
<223> OTHER INFORMATION: synthetic

<400> SEQUENCE: 153

Ala Val Leu Glu Leu Phe Glu Asn Leu Leu Glu Arg Leu Leu Asp Ala
1               5                   10                  15

Leu Gln Lys Lys Leu Lys
            20

<210> SEQ ID NO 154
<211> LENGTH: 22
<212> TYPE: PRT
<213> ORGANISM: Artificial sequence
<220> FEATURE:
<223> OTHER INFORMATION: synthetic

<400> SEQUENCE: 154

Pro Val Leu Glu Leu Phe Glu Asn Leu Leu Glu Arg Gly Leu Asp Ala
1               5                   10                  15

Leu Gln Lys Lys Leu Lys
            20

<210> SEQ ID NO 155
<211> LENGTH: 22
<212> TYPE: PRT
<213> ORGANISM: Artificial sequence
<220> FEATURE:
<223> OTHER INFORMATION: synthetic

<400> SEQUENCE: 155

Pro Val Leu Glu Leu Phe Leu Asn Leu Trp Glu Arg Leu Leu Asp Ala
1               5                   10                  15

Leu Gln Lys Lys Leu Lys
            20

<210> SEQ ID NO 156
<211> LENGTH: 22
<212> TYPE: PRT
<213> ORGANISM: Artificial sequence
<220> FEATURE:
<223> OTHER INFORMATION: synthetic

<400> SEQUENCE: 156

Pro Val Leu Glu Leu Phe Leu Asn Leu Leu Glu Arg Leu Leu Asp Ala
1               5                   10                  15

Leu Gln Lys Lys Leu Lys
            20

<210> SEQ ID NO 157
<211> LENGTH: 22
<212> TYPE: PRT
<213> ORGANISM: Artificial sequence
<220> FEATURE:
<223> OTHER INFORMATION: synthetic

<400> SEQUENCE: 157

Pro Val Leu Glu Phe Phe Glu Asn Leu Leu Glu Arg Leu Leu Asp Ala
1               5                   10                  15

Leu Gln Lys Lys Leu Lys
            20

<210> SEQ ID NO 158
<211> LENGTH: 22
<212> TYPE: PRT
<213> ORGANISM: Artificial sequence
<220> FEATURE:
<223> OTHER INFORMATION: synthetic

<400> SEQUENCE: 158

Pro Val Leu Glu Leu Phe Leu Asn Leu Leu Glu Arg Leu Leu Asp Trp
1               5                   10                  15

Leu Gln Lys Lys Leu Lys
            20

<210> SEQ ID NO 159
<211> LENGTH: 22
<212> TYPE: PRT
<213> ORGANISM: Artificial sequence
<220> FEATURE:
<223> OTHER INFORMATION: synthetic

<400> SEQUENCE: 159

Pro Val Leu Asp Leu Phe Glu Asn Leu Leu Glu Arg Leu Leu Asp Ala
1               5                   10                  15

Leu Gln Lys Lys Leu Lys
            20

<210> SEQ ID NO 160
<211> LENGTH: 22
<212> TYPE: PRT
<213> ORGANISM: Artificial sequence
<220> FEATURE:
<223> OTHER INFORMATION: synthetic

<400> SEQUENCE: 160

Pro Val Leu Glu Leu Phe Glu Asn Leu Leu Glu Arg Leu Leu Asp Trp
1               5                   10                  15

Leu Gln Lys Lys Leu Lys
            20

<210> SEQ ID NO 161
<211> LENGTH: 22
<212> TYPE: PRT
<213> ORGANISM: Artificial sequence
<220> FEATURE:
<223> OTHER INFORMATION: synthetic

<400> SEQUENCE: 161

Pro Val Leu Glu Leu Phe Glu Asn Leu Leu Glu Arg Leu Leu Glu Ala
1               5                   10                  15

Leu Gln Lys Lys Leu Lys
            20

<210> SEQ ID NO 162
<211> LENGTH: 22
<212> TYPE: PRT
<213> ORGANISM: Artificial sequence
<220> FEATURE:
<223> OTHER INFORMATION: synthetic

<400> SEQUENCE: 162

Pro Val Leu Glu Leu Phe Glu Asn Trp Leu Glu Arg Leu Leu Asp Ala
1               5                   10                  15

Leu Gln Lys Lys Leu Lys
            20

<210> SEQ ID NO 163
<211> LENGTH: 22
<212> TYPE: PRT
<213> ORGANISM: Artificial sequence
<220> FEATURE:
<223> OTHER INFORMATION: synthetic

<400> SEQUENCE: 163

Pro Val Leu Glu Leu Phe Glu Asn Leu Leu Glu Arg Leu Trp Asp Ala
1               5                   10                  15

Leu Gln Lys Lys Leu Lys
            20

<210> SEQ ID NO 164
<211> LENGTH: 22
<212> TYPE: PRT
<213> ORGANISM: Artificial sequence
<220> FEATURE:
<223> OTHER INFORMATION: synthetic

<400> SEQUENCE: 164

Pro Val Leu Glu Leu Phe Glu Asn Leu Leu Glu Arg Leu Leu Asp Ala
1               5                   10                  15

Trp Gln Lys Lys Leu Lys
            20

<210> SEQ ID NO 165
<211> LENGTH: 22
<212> TYPE: PRT
<213> ORGANISM: Artificial sequence
<220> FEATURE:
<223> OTHER INFORMATION: synthetic

<400> SEQUENCE: 165

Pro Val Leu Glu Leu Phe Glu Asn Leu Leu Glu Arg Leu Leu Asp Leu
1               5                   10                  15

Leu Gln Lys Lys Leu Lys
            20

<210> SEQ ID NO 166
<211> LENGTH: 22
<212> TYPE: PRT
<213> ORGANISM: Artificial sequence
<220> FEATURE:
<223> OTHER INFORMATION: synthetic

<400> SEQUENCE: 166

Pro Val Leu Glu Leu Phe Leu Asn Leu Leu Glu Lys Leu Leu Asp Ala
1               5                   10                  15

Leu Gln Lys Lys Leu Lys
            20

<210> SEQ ID NO 167
<211> LENGTH: 22
<212> TYPE: PRT
<213> ORGANISM: Artificial sequence
<220> FEATURE:
<223> OTHER INFORMATION: synthetic

<400> SEQUENCE: 167

Pro Val Leu Glu Leu Phe Glu Asn Gly Leu Glu Arg Leu Leu Asp Ala
1               5                   10                  15

Leu Gln Lys Lys Leu Lys
            20

<210> SEQ ID NO 168
<211> LENGTH: 22
<212> TYPE: PRT
<213> ORGANISM: Artificial sequence
<220> FEATURE:
<223> OTHER INFORMATION: synthetic

<400> SEQUENCE: 168

Pro Val Leu Glu Leu Phe Glu Gln Leu Leu Glu Lys Leu Leu Asp Ala
1               5                   10                  15

Leu Gln Lys Lys Leu Lys
            20

<210> SEQ ID NO 169
<211> LENGTH: 22
<212> TYPE: PRT
<213> ORGANISM: Artificial sequence
<220> FEATURE:
<223> OTHER INFORMATION: synthetic

<400> SEQUENCE: 169

Pro Val Leu Glu Leu Phe Glu Asn Leu Leu Glu Lys Leu Leu Asp Ala
1               5                   10                  15

Leu Gln Lys Lys Leu Lys
            20

<210> SEQ ID NO 170
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 170

Pro Val Leu Glu Leu Phe Glu Asn Leu Leu Glu Xaa Leu Leu Asp Ala
1               5                   10                  15

Leu Gln Xaa Xaa Leu Xaa
            20

<210> SEQ ID NO 171
<211> LENGTH: 22
<212> TYPE: PRT
<213> ORGANISM: Artificial sequence
<220> FEATURE:
<223> OTHER INFORMATION: synthetic

```
<400> SEQUENCE: 171

Pro Val Leu Glu Leu Phe Glu Asn Leu Leu Glu Lys Leu Leu Asp Leu
1               5                   10                  15

Leu Gln Lys Lys Leu Lys
            20

<210> SEQ ID NO 172
<211> LENGTH: 22
<212> TYPE: PRT
<213> ORGANISM: Artificial sequence
<220> FEATURE:
<223> OTHER INFORMATION: synthetic

<400> SEQUENCE: 172

Pro Val Leu Glu Leu Phe Leu Asn Leu Leu Glu Arg Leu Gly Asp Ala
1               5                   10                  15

Leu Gln Lys Lys Leu Lys
            20

<210> SEQ ID NO 173
<211> LENGTH: 22
<212> TYPE: PRT
<213> ORGANISM: Artificial sequence
<220> FEATURE:
<223> OTHER INFORMATION: synthetic

<400> SEQUENCE: 173

Pro Val Leu Asp Leu Phe Asp Asn Leu Leu Asp Arg Leu Leu Asp Leu
1               5                   10                  15

Leu Asn Lys Lys Leu Lys
            20

<210> SEQ ID NO 174
<211> LENGTH: 22
<212> TYPE: PRT
<213> ORGANISM: Artificial sequence
<220> FEATURE:
<223> OTHER INFORMATION: synthetic

<400> SEQUENCE: 174

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 175
<211> LENGTH: 22
<212> TYPE: PRT
<213> ORGANISM: Artificial sequence
<220> FEATURE:
<223> OTHER INFORMATION: synthetic

<400> SEQUENCE: 175

Pro Val Leu Glu Leu Phe Glu Asn Leu Leu Glu Arg Leu Leu Glu Leu
1               5                   10                  15

Leu Asn Lys Lys Leu Lys
            20

<210> SEQ ID NO 176
<211> LENGTH: 22
<212> TYPE: PRT
<213> ORGANISM: Artificial sequence
<220> FEATURE:
```

<223> OTHER INFORMATION: synthetic

<400> SEQUENCE: 176

Pro Val Leu Glu Leu Trp Glu Asn Leu Leu Glu Arg Leu Leu Asp Ala
1               5                   10                  15

Leu Gln Lys Lys Leu Lys
            20

<210> SEQ ID NO 177
<211> LENGTH: 22
<212> TYPE: PRT
<213> ORGANISM: Artificial sequence
<220> FEATURE:
<223> OTHER INFORMATION: synthetic

<400> SEQUENCE: 177

Gly Val Leu Glu Leu Phe Leu Asn Leu Leu Glu Arg Leu Leu Asp Ala
1               5                   10                  15

Leu Gln Lys Lys Leu Lys
            20

<210> SEQ ID NO 178
<211> LENGTH: 22
<212> TYPE: PRT
<213> ORGANISM: Artificial sequence
<220> FEATURE:
<223> OTHER INFORMATION: synthetic

<400> SEQUENCE: 178

Pro Val Leu Glu Leu Phe Asp Asn Leu Leu Glu Lys Leu Leu Glu Ala
1               5                   10                  15

Leu Gln Lys Lys Leu Arg
            20

<210> SEQ ID NO 179
<211> LENGTH: 22
<212> TYPE: PRT
<213> ORGANISM: Artificial sequence
<220> FEATURE:
<223> OTHER INFORMATION: synthetic

<400> SEQUENCE: 179

Pro Val Leu Glu Leu Phe Asp Asn Leu Leu Glu Arg Leu Leu Asp Ala
1               5                   10                  15

Leu Gln Lys Lys Leu Lys
            20

<210> SEQ ID NO 180
<211> LENGTH: 22
<212> TYPE: PRT
<213> ORGANISM: Artificial sequence
<220> FEATURE:
<223> OTHER INFORMATION: synthetic

<400> SEQUENCE: 180

Pro Val Leu Glu Leu Phe Asp Asn Leu Leu Asp Lys Leu Leu Asp Ala
1               5                   10                  15

Leu Gln Lys Lys Leu Arg
            20

<210> SEQ ID NO 181
<211> LENGTH: 22
<212> TYPE: PRT
<213> ORGANISM: Artificial sequence

```
<220> FEATURE:
<223> OTHER INFORMATION: synthetic

<400> SEQUENCE: 181

Pro Val Leu Glu Leu Phe Glu Asn Leu Leu Glu Arg Trp Leu Asp Ala
1               5                   10                  15

Leu Gln Lys Lys Leu Lys
            20

<210> SEQ ID NO 182
<211> LENGTH: 22
<212> TYPE: PRT
<213> ORGANISM: Artificial sequence
<220> FEATURE:
<223> OTHER INFORMATION: synthetic

<400> SEQUENCE: 182

Pro Val Leu Glu Leu Phe Glu Asn Leu Leu Glu Lys Leu Leu Glu Ala
1               5                   10                  15

Leu Gln Lys Lys Leu Lys
            20

<210> SEQ ID NO 183
<211> LENGTH: 22
<212> TYPE: PRT
<213> ORGANISM: Artificial sequence
<220> FEATURE:
<223> OTHER INFORMATION: synthetic

<400> SEQUENCE: 183

Pro Leu Leu Glu Leu Phe Glu Asn Leu Leu Glu Lys Leu Leu Asp Ala
1               5                   10                  15

Leu Gln Lys Lys Leu Lys
            20

<210> SEQ ID NO 184
<211> LENGTH: 22
<212> TYPE: PRT
<213> ORGANISM: Artificial sequence
<220> FEATURE:
<223> OTHER INFORMATION: synthetic

<400> SEQUENCE: 184

Pro Val Leu Glu Leu Phe Leu Asn Leu Leu Glu Arg Leu Leu Asp Ala
1               5                   10                  15

Trp Gln Lys Lys Leu Lys
            20

<210> SEQ ID NO 185
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 185
```

```
Pro Val Leu Glu Leu Phe Glu Asn Leu Leu Glu Arg Leu Leu Asp Ala
1               5                   10                  15

Leu Gln Xaa Xaa Leu Xaa
            20
```

<210> SEQ ID NO 186
<211> LENGTH: 22
<212> TYPE: PRT
<213> ORGANISM: Artificial sequence
<220> FEATURE:
<223> OTHER INFORMATION: synthetic

<400> SEQUENCE: 186

```
Pro Val Leu Glu Leu Phe Glu Gln Leu Leu Glu Arg Leu Leu Asp Ala
1               5                   10                  15

Leu Gln Lys Lys Leu Lys
            20
```

<210> SEQ ID NO 187
<211> LENGTH: 22
<212> TYPE: PRT
<213> ORGANISM: Artificial sequence
<220> FEATURE:
<223> OTHER INFORMATION: synthetic

<400> SEQUENCE: 187

```
Pro Val Leu Glu Leu Phe Glu Asn Leu Leu Glu Arg Leu Leu Asp Ala
1               5                   10                  15

Leu Asn Lys Lys Leu Lys
            20
```

<210> SEQ ID NO 188
<211> LENGTH: 22
<212> TYPE: PRT
<213> ORGANISM: Artificial sequence
<220> FEATURE:
<223> OTHER INFORMATION: synthetic

<400> SEQUENCE: 188

```
Pro Val Leu Glu Leu Phe Glu Asn Leu Leu Asp Arg Leu Leu Asp Ala
1               5                   10                  15

Leu Gln Lys Lys Leu Lys
            20
```

<210> SEQ ID NO 189
<211> LENGTH: 22
<212> TYPE: PRT
<213> ORGANISM: Artificial sequence
<220> FEATURE:
<223> OTHER INFORMATION: synthetic

<400> SEQUENCE: 189

```
Asp Val Leu Glu Leu Phe Glu Asn Leu Leu Glu Arg Leu Leu Asp Ala
1               5                   10                  15

Leu Gln Lys Lys Leu Lys
            20
```

<210> SEQ ID NO 190
<211> LENGTH: 22
<212> TYPE: PRT
<213> ORGANISM: Artificial sequence
<220> FEATURE:
<223> OTHER INFORMATION: synthetic -continued

```
<400> SEQUENCE: 190

Pro Val Leu Glu Phe Trp Asp Asn Leu Leu Asp Lys Leu Leu Asp Ala
1               5                   10                  15
Leu Gln Lys Lys Leu Arg
            20

<210> SEQ ID NO 191
<211> LENGTH: 18
<212> TYPE: PRT
<213> ORGANISM: Artificial sequence
<220> FEATURE:
<223> OTHER INFORMATION: synthetic

<400> SEQUENCE: 191

Pro Val Leu Asp Leu Leu Arg Glu Leu Leu Glu Glu Leu Lys Gln Lys
1               5                   10                  15
Leu Lys

<210> SEQ ID NO 192
<211> LENGTH: 18
<212> TYPE: PRT
<213> ORGANISM: Artificial sequence
<220> FEATURE:
<223> OTHER INFORMATION: synthetic

<400> SEQUENCE: 192

Pro Val Leu Asp Leu Phe Lys Glu Leu Leu Glu Glu Leu Lys Gln Lys
1               5                   10                  15
Leu Lys

<210> SEQ ID NO 193
<211> LENGTH: 18
<212> TYPE: PRT
<213> ORGANISM: Artificial sequence
<220> FEATURE:
<223> OTHER INFORMATION: synthetic

<400> SEQUENCE: 193

Pro Val Leu Asp Leu Phe Arg Glu Leu Leu Glu Glu Leu Lys Gln Lys
1               5                   10                  15
Leu Lys

<210> SEQ ID NO 194
<211> LENGTH: 18
<212> TYPE: PRT
<213> ORGANISM: Artificial sequence
<220> FEATURE:
<223> OTHER INFORMATION: synthetic

<400> SEQUENCE: 194

Pro Val Leu Glu Leu Phe Arg Glu Leu Leu Glu Glu Leu Lys Gln Lys
1               5                   10                  15
Leu Lys

<210> SEQ ID NO 195
<211> LENGTH: 18
<212> TYPE: PRT
<213> ORGANISM: Artificial sequence
<220> FEATURE:
<223> OTHER INFORMATION: synthetic

<400> SEQUENCE: 195

Pro Val Leu Glu Leu Phe Lys Glu Leu Leu Glu Glu Leu Lys Gln Lys
```

```
1               5                  10                 15

Leu Lys

<210> SEQ ID NO 196
<211> LENGTH: 18
<212> TYPE: PRT
<213> ORGANISM: Artificial sequence
<220> FEATURE:
<223> OTHER INFORMATION: synthetic

<400> SEQUENCE: 196

Pro Val Leu Asp Leu Phe Arg Glu Leu Leu Glu Glu Leu Lys Asn Lys
1               5                  10                 15

Leu Lys

<210> SEQ ID NO 197
<211> LENGTH: 18
<212> TYPE: PRT
<213> ORGANISM: Artificial sequence
<220> FEATURE:
<223> OTHER INFORMATION: synthetic

<400> SEQUENCE: 197

Pro Leu Leu Asp Leu Phe Arg Glu Leu Leu Glu Glu Leu Lys Gln Lys
1               5                  10                 15

Leu Lys

<210> SEQ ID NO 198
<211> LENGTH: 18
<212> TYPE: PRT
<213> ORGANISM: Artificial sequence
<220> FEATURE:
<223> OTHER INFORMATION: synthetic

<400> SEQUENCE: 198

Gly Val Leu Asp Leu Phe Arg Glu Leu Leu Glu Glu Leu Lys Gln Lys
1               5                  10                 15

Leu Lys

<210> SEQ ID NO 199
<211> LENGTH: 18
<212> TYPE: PRT
<213> ORGANISM: Artificial sequence
<220> FEATURE:
<223> OTHER INFORMATION: synthetic

<400> SEQUENCE: 199

Pro Val Leu Asp Leu Phe Arg Glu Leu Trp Glu Glu Leu Lys Gln Lys
1               5                  10                 15

Leu Lys

<210> SEQ ID NO 200
<211> LENGTH: 18
<212> TYPE: PRT
<213> ORGANISM: Artificial sequence
<220> FEATURE:
<223> OTHER INFORMATION: synthetic

<400> SEQUENCE: 200

Asn Val Leu Asp Leu Phe Arg Glu Leu Leu Glu Glu Leu Lys Gln Lys
1               5                  10                 15

Leu Lys
```

<210> SEQ ID NO 201
<211> LENGTH: 18
<212> TYPE: PRT
<213> ORGANISM: Artificial sequence
<220> FEATURE:
<223> OTHER INFORMATION: synthetic

<400> SEQUENCE: 201

Pro Leu Leu Asp Leu Phe Lys Glu Leu Leu Glu Glu Leu Lys Gln Lys
1               5                   10                  15

Leu Lys

<210> SEQ ID NO 202
<211> LENGTH: 18
<212> TYPE: PRT
<213> ORGANISM: Artificial sequence
<220> FEATURE:
<223> OTHER INFORMATION: synthetic

<400> SEQUENCE: 202

Pro Ala Leu Glu Leu Phe Lys Asp Leu Leu Glu Glu Leu Arg Gln Lys
1               5                   10                  15

Leu Arg

<210> SEQ ID NO 203
<211> LENGTH: 18
<212> TYPE: PRT
<213> ORGANISM: Artificial sequence
<220> FEATURE:
<223> OTHER INFORMATION: synthetic

<400> SEQUENCE: 203

Ala Val Leu Asp Leu Phe Arg Glu Leu Leu Glu Glu Leu Lys Gln Lys
1               5                   10                  15

Leu Lys

<210> SEQ ID NO 204
<211> LENGTH: 18
<212> TYPE: PRT
<213> ORGANISM: Artificial sequence
<220> FEATURE:
<223> OTHER INFORMATION: synthetic

<400> SEQUENCE: 204

Pro Val Leu Asp Phe Phe Arg Glu Leu Leu Glu Glu Leu Lys Gln Lys
1               5                   10                  15

Leu Lys

<210> SEQ ID NO 205
<211> LENGTH: 18
<212> TYPE: PRT
<213> ORGANISM: Artificial sequence
<220> FEATURE:
<223> OTHER INFORMATION: synthetic

<400> SEQUENCE: 205

Pro Val Leu Asp Leu Phe Arg Glu Trp Leu Glu Glu Leu Lys Gln Lys
1               5                   10                  15

Leu Lys

<210> SEQ ID NO 206
<211> LENGTH: 18
<212> TYPE: PRT

<210> SEQ ID NO 206
<211> LENGTH: 18
<212> TYPE: PRT
<213> ORGANISM: Artificial sequence
<220> FEATURE:
<223> OTHER INFORMATION: synthetic

<400> SEQUENCE: 206

Pro Leu Leu Glu Leu Leu Lys Glu Leu Leu Glu Glu Leu Lys Gln Lys
1               5                   10                  15

Leu Lys

<210> SEQ ID NO 207
<211> LENGTH: 18
<212> TYPE: PRT
<213> ORGANISM: Artificial sequence
<220> FEATURE:
<223> OTHER INFORMATION: synthetic

<400> SEQUENCE: 207

Pro Val Leu Glu Leu Leu Lys Glu Leu Leu Glu Glu Leu Lys Gln Lys
1               5                   10                  15

Leu Lys

<210> SEQ ID NO 208
<211> LENGTH: 18
<212> TYPE: PRT
<213> ORGANISM: Artificial sequence
<220> FEATURE:
<223> OTHER INFORMATION: synthetic

<400> SEQUENCE: 208

Pro Ala Leu Glu Leu Phe Lys Asp Leu Leu Glu Glu Leu Arg Gln Arg
1               5                   10                  15

Leu Lys

<210> SEQ ID NO 209
<211> LENGTH: 18
<212> TYPE: PRT
<213> ORGANISM: Artificial sequence
<220> FEATURE:
<223> OTHER INFORMATION: synthetic

<400> SEQUENCE: 209

Pro Val Leu Asp Leu Phe Arg Glu Leu Leu Asn Glu Leu Leu Gln Lys
1               5                   10                  15

Leu Lys

<210> SEQ ID NO 210
<211> LENGTH: 18
<212> TYPE: PRT
<213> ORGANISM: Artificial sequence
<220> FEATURE:
<223> OTHER INFORMATION: synthetic

<400> SEQUENCE: 210

Pro Val Leu Asp Leu Phe Arg Glu Leu Leu Glu Glu Leu Lys Gln Lys
1               5                   10                  15

Leu Lys

<210> SEQ ID NO 211
<211> LENGTH: 18
<212> TYPE: PRT
<213> ORGANISM: Artificial sequence
<220> FEATURE:
<223> OTHER INFORMATION: synthetic
<220> FEATURE:

```
<221> NAME/KEY: misc_feature
<223> OTHER INFORMATION: Xaa = Orn
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 211

Pro Val Leu Asp Leu Phe Arg Glu Leu Leu Glu Glu Leu Xaa Gln Xaa
1               5                   10                  15

Leu Xaa

<210> SEQ ID NO 212
<211> LENGTH: 18
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 212

Pro Val Leu Asp Leu Phe Xaa Glu Leu Leu Glu Glu Leu Xaa Gln Xaa
1               5                   10                  15

Leu Lys

<210> SEQ ID NO 213
<211> LENGTH: 18
<212> TYPE: PRT
<213> ORGANISM: Artificial sequence
<220> FEATURE:
<223> OTHER INFORMATION: synthetic

<400> SEQUENCE: 213

Pro Ala Leu Glu Leu Phe Lys Asp Leu Leu Glu Glu Phe Arg Gln Arg
1               5                   10                  15

Leu Lys

<210> SEQ ID NO 214
<211> LENGTH: 18
<212> TYPE: PRT
<213> ORGANISM: Artificial sequence
<220> FEATURE:
<223> OTHER INFORMATION: synthetic

<400> SEQUENCE: 214

Pro Val Leu Asp Leu Phe Arg Glu Leu Leu Glu Glu Leu Lys Gln Lys
1               5                   10                  15
```

Leu Lys

<210> SEQ ID NO 215
<211> LENGTH: 18
<212> TYPE: PRT
<213> ORGANISM: Artificial sequence
<220> FEATURE:
<223> OTHER INFORMATION: synthetic

<400> SEQUENCE: 215

Pro Val Leu Asp Leu Phe Arg Glu Leu Leu Glu Glu Trp Lys Gln Lys
1               5                   10                  15

Leu Lys

<210> SEQ ID NO 216
<211> LENGTH: 18
<212> TYPE: PRT
<213> ORGANISM: Artificial sequence
<220> FEATURE:
<223> OTHER INFORMATION: synthetic

<400> SEQUENCE: 216

Pro Val Leu Glu Leu Phe Lys Glu Leu Leu Glu Glu Leu Lys Gln Lys
1               5                   10                  15

Leu Lys

<210> SEQ ID NO 217
<211> LENGTH: 18
<212> TYPE: PRT
<213> ORGANISM: Artificial sequence
<220> FEATURE:
<223> OTHER INFORMATION: synthetic

<400> SEQUENCE: 217

Pro Val Leu Asp Leu Phe Arg Glu Leu Leu Glu Leu Leu Lys Gln Lys
1               5                   10                  15

Leu Lys

<210> SEQ ID NO 218
<211> LENGTH: 18
<212> TYPE: PRT
<213> ORGANISM: Artificial sequence
<220> FEATURE:
<223> OTHER INFORMATION: synthetic

<400> SEQUENCE: 218

Pro Val Leu Asp Leu Phe Arg Glu Leu Leu Asn Glu Leu Leu Gln Lys
1               5                   10                  15

Leu Lys

<210> SEQ ID NO 219
<211> LENGTH: 18
<212> TYPE: PRT
<213> ORGANISM: Artificial sequence
<220> FEATURE:
<223> OTHER INFORMATION: synthetic

<400> SEQUENCE: 219

Pro Val Leu Asp Leu Phe Arg Glu Leu Leu Asn Glu Leu Trp Gln Lys
1               5                   10                  15

Leu Lys

```
<210> SEQ ID NO 220
<211> LENGTH: 18
<212> TYPE: PRT
<213> ORGANISM: Artificial sequence
<220> FEATURE:
<223> OTHER INFORMATION: synthetic

<400> SEQUENCE: 220

Pro Val Leu Asp Leu Phe Arg Glu Leu Leu Glu Glu Leu Gln Lys Lys
1               5                   10                  15

Leu Lys

<210> SEQ ID NO 221
<211> LENGTH: 18
<212> TYPE: PRT
<213> ORGANISM: Artificial sequence
<220> FEATURE:
<223> OTHER INFORMATION: synthetic

<400> SEQUENCE: 221

Asp Val Leu Asp Leu Phe Arg Glu Leu Leu Glu Glu Leu Lys Gln Lys
1               5                   10                  15

Leu Lys

<210> SEQ ID NO 222
<211> LENGTH: 18
<212> TYPE: PRT
<213> ORGANISM: Artificial sequence
<220> FEATURE:
<223> OTHER INFORMATION: synthetic

<400> SEQUENCE: 222

Pro Val Leu Asp Ala Phe Arg Glu Leu Leu Glu Ala Leu Leu Gln Leu
1               5                   10                  15

Lys Lys

<210> SEQ ID NO 223
<211> LENGTH: 18
<212> TYPE: PRT
<213> ORGANISM: Artificial sequence
<220> FEATURE:
<223> OTHER INFORMATION: synthetic

<400> SEQUENCE: 223

Pro Val Leu Asp Ala Phe Arg Glu Leu Leu Glu Ala Leu Ala Gln Leu
1               5                   10                  15

Lys Lys

<210> SEQ ID NO 224
<211> LENGTH: 18
<212> TYPE: PRT
<213> ORGANISM: Artificial sequence
<220> FEATURE:
<223> OTHER INFORMATION: synthetic

<400> SEQUENCE: 224

Pro Val Leu Asp Leu Phe Arg Glu Gly Trp Glu Glu Leu Lys Gln Lys
1               5                   10                  15

Leu Lys

<210> SEQ ID NO 225
<211> LENGTH: 18
<212> TYPE: PRT
<213> ORGANISM: Artificial sequence
```

-continued

<220> FEATURE:
<223> OTHER INFORMATION: synthetic

<400> SEQUENCE: 225

Pro Val Leu Asp Ala Phe Arg Glu Leu Ala Glu Ala Leu Ala Gln Leu
1               5                   10                  15

Lys Lys

<210> SEQ ID NO 226
<211> LENGTH: 18
<212> TYPE: PRT
<213> ORGANISM: Artificial sequence
<220> FEATURE:
<223> OTHER INFORMATION: synthetic

<400> SEQUENCE: 226

Pro Val Leu Asp Ala Phe Arg Glu Leu Gly Glu Ala Leu Leu Gln Leu
1               5                   10                  15

Lys Lys

<210> SEQ ID NO 227
<211> LENGTH: 18
<212> TYPE: PRT
<213> ORGANISM: Artificial sequence
<220> FEATURE:
<223> OTHER INFORMATION: synthetic

<400> SEQUENCE: 227

Pro Val Leu Asp Leu Phe Arg Glu Leu Gly Glu Glu Leu Lys Gln Lys
1               5                   10                  15

Leu Lys

<210> SEQ ID NO 228
<211> LENGTH: 18
<212> TYPE: PRT
<213> ORGANISM: Artificial sequence
<220> FEATURE:
<223> OTHER INFORMATION: synthetic

<400> SEQUENCE: 228

Pro Val Leu Asp Leu Phe Arg Glu Gly Leu Glu Glu Leu Lys Gln Lys
1               5                   10                  15

Leu Lys

<210> SEQ ID NO 229
<211> LENGTH: 18
<212> TYPE: PRT
<213> ORGANISM: Artificial sequence
<220> FEATURE:
<223> OTHER INFORMATION: synthetic

<400> SEQUENCE: 229

Pro Val Leu Asp Leu Phe Arg Glu Leu Leu Glu Glu Gly Lys Gln Lys
1               5                   10                  15

Leu Lys

<210> SEQ ID NO 230
<211> LENGTH: 18
<212> TYPE: PRT
<213> ORGANISM: Artificial sequence
<220> FEATURE:
<223> OTHER INFORMATION: synthetic

<400> SEQUENCE: 230

```
Pro Val Leu Glu Leu Phe Glu Arg Leu Leu Glu Asp Leu Gln Lys Lys
1               5                   10                  15

Leu Lys

<210> SEQ ID NO 231
<211> LENGTH: 18
<212> TYPE: PRT
<213> ORGANISM: Artificial sequence
<220> FEATURE:
<223> OTHER INFORMATION: synthetic

<400> SEQUENCE: 231

Pro Val Leu Asp Leu Phe Arg Glu Leu Leu Glu Lys Leu Glu Gln Lys
1               5                   10                  15

Leu Lys

<210> SEQ ID NO 232
<211> LENGTH: 18
<212> TYPE: PRT
<213> ORGANISM: Artificial sequence
<220> FEATURE:
<223> OTHER INFORMATION: synthetic

<400> SEQUENCE: 232

Pro Leu Leu Glu Leu Phe Lys Glu Leu Leu Glu Glu Leu Lys Gln Lys
1               5                   10                  15

Leu Lys

<210> SEQ ID NO 233
<211> LENGTH: 18
<212> TYPE: PRT
<213> ORGANISM: Artificial sequence
<220> FEATURE:
<223> OTHER INFORMATION: synthetic

<400> SEQUENCE: 233

Leu Asp Asp Leu Leu Gln Lys Trp Ala Glu Ala Phe Asn Gln Leu Leu
1               5                   10                  15

Lys Lys

<210> SEQ ID NO 234
<211> LENGTH: 18
<212> TYPE: PRT
<213> ORGANISM: Artificial sequence
<220> FEATURE:
<223> OTHER INFORMATION: synthetic

<400> SEQUENCE: 234

Glu Trp Leu Lys Ala Phe Tyr Glu Lys Val Leu Glu Lys Leu Lys Glu
1               5                   10                  15

Leu Phe

<210> SEQ ID NO 235
<211> LENGTH: 18
<212> TYPE: PRT
<213> ORGANISM: Artificial sequence
<220> FEATURE:
<223> OTHER INFORMATION: synthetic

<400> SEQUENCE: 235

Glu Trp Leu Glu Ala Phe Tyr Lys Lys Val Leu Glu Lys Leu Lys Glu
1               5                   10                  15
```

Leu Phe

<210> SEQ ID NO 236
<211> LENGTH: 18
<212> TYPE: PRT
<213> ORGANISM: Artificial sequence
<220> FEATURE:
<223> OTHER INFORMATION: synthetic

<400> SEQUENCE: 236

Asp Trp Leu Lys Ala Phe Tyr Asp Lys Val Ala Glu Lys Leu Lys Glu
1               5                   10                  15

Ala Phe

<210> SEQ ID NO 237
<211> LENGTH: 18
<212> TYPE: PRT
<213> ORGANISM: Artificial sequence
<220> FEATURE:
<223> OTHER INFORMATION: synthetic

<400> SEQUENCE: 237

Asp Trp Phe Lys Ala Phe Tyr Asp Lys Val Phe Glu Lys Phe Lys Glu
1               5                   10                  15

Phe Phe

<210> SEQ ID NO 238
<211> LENGTH: 18
<212> TYPE: PRT
<213> ORGANISM: Artificial sequence
<220> FEATURE:
<223> OTHER INFORMATION: synthetic

<400> SEQUENCE: 238

Gly Ile Lys Lys Phe Leu Gly Ser Ile Trp Lys Phe Ile Lys Ala Phe
1               5                   10                  15

Val Gly

<210> SEQ ID NO 239
<211> LENGTH: 18
<212> TYPE: PRT
<213> ORGANISM: Artificial sequence
<220> FEATURE:
<223> OTHER INFORMATION: synthetic

<400> SEQUENCE: 239

Asp Trp Phe Lys Ala Phe Tyr Asp Lys Val Ala Glu Lys Phe Lys Glu
1               5                   10                  15

Ala Phe

<210> SEQ ID NO 240
<211> LENGTH: 18
<212> TYPE: PRT
<213> ORGANISM: Artificial sequence
<220> FEATURE:
<223> OTHER INFORMATION: synthetic

<400> SEQUENCE: 240

Asp Trp Leu Lys Ala Phe Tyr Asp Lys Val Ala Glu Lys Leu Lys Glu
1               5                   10                  15

Ala Phe

<210> SEQ ID NO 241

```
<211> LENGTH: 18
<212> TYPE: PRT
<213> ORGANISM: Artificial sequence
<220> FEATURE:
<223> OTHER INFORMATION: synthetic

<400> SEQUENCE: 241

Asp Trp Leu Lys Ala Phe Tyr Asp Lys Val Phe Glu Lys Phe Lys Glu
1               5                   10                  15

Phe Phe

<210> SEQ ID NO 242
<211> LENGTH: 18
<212> TYPE: PRT
<213> ORGANISM: Artificial sequence
<220> FEATURE:
<223> OTHER INFORMATION: synthetic

<400> SEQUENCE: 242

Glu Trp Leu Glu Ala Phe Tyr Lys Lys Val Leu Glu Lys Leu Lys Glu
1               5                   10                  15

Leu Pro

<210> SEQ ID NO 243
<211> LENGTH: 18
<212> TYPE: PRT
<213> ORGANISM: Artificial sequence
<220> FEATURE:
<223> OTHER INFORMATION: synthetic

<400> SEQUENCE: 243

Asp Trp Phe Lys Ala Phe Tyr Asp Lys Phe Phe Glu Lys Phe Lys Glu
1               5                   10                  15

Phe Phe

<210> SEQ ID NO 244
<211> LENGTH: 18
<212> TYPE: PRT
<213> ORGANISM: Artificial sequence
<220> FEATURE:
<223> OTHER INFORMATION: synthetic

<400> SEQUENCE: 244

Glu Trp Leu Lys Ala Phe Tyr Glu Lys Val Leu Glu Lys Leu Lys Glu
1               5                   10                  15

Leu Phe

<210> SEQ ID NO 245
<211> LENGTH: 18
<212> TYPE: PRT
<213> ORGANISM: Artificial sequence
<220> FEATURE:
<223> OTHER INFORMATION: synthetic

<400> SEQUENCE: 245

Glu Trp Leu Lys Ala Glu Tyr Glu Lys Val Glu Glu Lys Leu Lys Glu
1               5                   10                  15

Leu Phe

<210> SEQ ID NO 246
<211> LENGTH: 18
<212> TYPE: PRT
<213> ORGANISM: Artificial sequence
<220> FEATURE:
```

<223> OTHER INFORMATION: synthetic

<400> SEQUENCE: 246

Glu Trp Leu Lys Ala Glu Tyr Glu Lys Val Leu Glu Lys Leu Lys Glu
1               5                   10                  15
Leu Phe

<210> SEQ ID NO 247
<211> LENGTH: 18
<212> TYPE: PRT
<213> ORGANISM: Artificial sequence
<220> FEATURE:
<223> OTHER INFORMATION: synthetic

<400> SEQUENCE: 247

Glu Trp Leu Lys Ala Phe Tyr Lys Lys Val Leu Glu Lys Leu Lys Glu
1               5                   10                  15
Leu Phe

<210> SEQ ID NO 248
<211> LENGTH: 15
<212> TYPE: PRT
<213> ORGANISM: Artificial sequence
<220> FEATURE:
<223> OTHER INFORMATION: synthetic

<400> SEQUENCE: 248

Pro Val Leu Asp Leu Phe Arg Glu Leu Leu Glu Gln Lys Leu Lys
1               5                   10                  15

<210> SEQ ID NO 249
<211> LENGTH: 16
<212> TYPE: PRT
<213> ORGANISM: Artificial sequence
<220> FEATURE:
<223> OTHER INFORMATION: synthetic

<400> SEQUENCE: 249

Pro Val Leu Asp Leu Phe Arg Glu Leu Leu Glu Glu Leu Lys Gln Lys
1               5                   10                  15

<210> SEQ ID NO 250
<211> LENGTH: 16
<212> TYPE: PRT
<213> ORGANISM: Artificial sequence
<220> FEATURE:
<223> OTHER INFORMATION: synthetic

<400> SEQUENCE: 250

Pro Val Leu Asp Leu Phe Arg Glu Leu Leu Glu Lys Leu Lys Gln Lys
1               5                   10                  15

<210> SEQ ID NO 251
<211> LENGTH: 15
<212> TYPE: PRT
<213> ORGANISM: Artificial sequence
<220> FEATURE:
<223> OTHER INFORMATION: synthetic

<400> SEQUENCE: 251

Pro Val Leu Asp Leu Phe Arg Glu Leu Leu Glu Lys Leu Gln Lys
1               5                   10                  15

<210> SEQ ID NO 252
<211> LENGTH: 16

```
<212> TYPE: PRT
<213> ORGANISM: Artificial sequence
<220> FEATURE:
<223> OTHER INFORMATION: synthetic

<400> SEQUENCE: 252

Pro Val Leu Asp Leu Phe Arg Glu Leu Leu Glu Ala Leu Lys Gln Lys
1               5                   10                  15

<210> SEQ ID NO 253
<211> LENGTH: 16
<212> TYPE: PRT
<213> ORGANISM: Artificial sequence
<220> FEATURE:
<223> OTHER INFORMATION: synthetic

<400> SEQUENCE: 253

Pro Val Leu Asp Leu Phe Glu Asn Leu Leu Glu Arg Leu Lys Gln Lys
1               5                   10                  15

<210> SEQ ID NO 254
<211> LENGTH: 16
<212> TYPE: PRT
<213> ORGANISM: Artificial sequence
<220> FEATURE:
<223> OTHER INFORMATION: synthetic

<400> SEQUENCE: 254

Pro Val Leu Asp Leu Phe Arg Glu Leu Leu Asn Glu Leu Lys Gln Lys
1               5                   10                  15

<210> SEQ ID NO 255
<211> LENGTH: 18
<212> TYPE: PRT
<213> ORGANISM: Artificial sequence
<220> FEATURE:
<223> OTHER INFORMATION: synthetic

<400> SEQUENCE: 255

Asp Trp Leu Lys Ala Phe Tyr Asp Lys Val Ala Glu Lys Leu Lys Glu
1               5                   10                  15

Ala Phe

<210> SEQ ID NO 256
<211> LENGTH: 18
<212> TYPE: PRT
<213> ORGANISM: Artificial sequence
<220> FEATURE:
<223> OTHER INFORMATION: synthetic

<400> SEQUENCE: 256

Asp Trp Leu Lys Ala Phe Tyr Asp Lys Val Ala Glu Lys Leu Lys Glu
1               5                   10                  15

Ala Phe

<210> SEQ ID NO 257
<211> LENGTH: 18
<212> TYPE: PRT
<213> ORGANISM: Artificial sequence
<220> FEATURE:
<223> OTHER INFORMATION: synthetic

<400> SEQUENCE: 257

Asp Trp Phe Lys Ala Phe Tyr Asp Lys Val Ala Glu Lys Leu Lys Glu
1               5                   10                  15
```

Ala Phe

<210> SEQ ID NO 258
<211> LENGTH: 18
<212> TYPE: PRT
<213> ORGANISM: Artificial sequence
<220> FEATURE:
<223> OTHER INFORMATION: synthetic

<400> SEQUENCE: 258

Asp Trp Leu Lys Ala Phe Tyr Asp Lys Val Ala Glu Lys Phe Lys Glu
1               5                   10                  15

Ala Phe

<210> SEQ ID NO 259
<211> LENGTH: 18
<212> TYPE: PRT
<213> ORGANISM: Artificial sequence
<220> FEATURE:
<223> OTHER INFORMATION: synthetic

<400> SEQUENCE: 259

Asp Trp Phe Lys Ala Phe Tyr Asp Lys Val Ala Glu Lys Phe Lys Glu
1               5                   10                  15

Ala Phe

<210> SEQ ID NO 260
<211> LENGTH: 18
<212> TYPE: PRT
<213> ORGANISM: Artificial sequence
<220> FEATURE:
<223> OTHER INFORMATION: synthetic

<400> SEQUENCE: 260

Asp Trp Leu Lys Ala Phe Tyr Asp Lys Val Phe Glu Lys Phe Lys Glu
1               5                   10                  15

Phe Phe

<210> SEQ ID NO 261
<211> LENGTH: 18
<212> TYPE: PRT
<213> ORGANISM: Artificial sequence
<220> FEATURE:
<223> OTHER INFORMATION: synthetic

<400> SEQUENCE: 261

Asp Trp Leu Lys Ala Phe Tyr Asp Lys Phe Phe Glu Lys Phe Lys Glu
1               5                   10                  15

Phe Phe

<210> SEQ ID NO 262
<211> LENGTH: 18
<212> TYPE: PRT
<213> ORGANISM: Artificial sequence
<220> FEATURE:
<223> OTHER INFORMATION: synthetic

<400> SEQUENCE: 262

Asp Trp Phe Lys Ala Phe Tyr Asp Lys Phe Phe Glu Lys Phe Lys Glu
1               5                   10                  15

Phe Phe

<210> SEQ ID NO 263

-continued

```
<211> LENGTH: 18
<212> TYPE: PRT
<213> ORGANISM: Artificial sequence
<220> FEATURE:
<223> OTHER INFORMATION: synthetic

<400> SEQUENCE: 263

Asp Trp Leu Lys Ala Phe Tyr Asp Lys Val Ala Glu Lys Leu Lys Glu
1               5                   10                  15

Phe Phe

<210> SEQ ID NO 264
<211> LENGTH: 18
<212> TYPE: PRT
<213> ORGANISM: Artificial sequence
<220> FEATURE:
<223> OTHER INFORMATION: synthetic

<400> SEQUENCE: 264

Asp Trp Leu Lys Ala Phe Tyr Asp Lys Val Phe Glu Lys Phe Lys Glu
1               5                   10                  15

Ala Phe

<210> SEQ ID NO 265
<211> LENGTH: 18
<212> TYPE: PRT
<213> ORGANISM: Artificial sequence
<220> FEATURE:
<223> OTHER INFORMATION: synthetic

<400> SEQUENCE: 265

Asp Trp Leu Lys Ala Phe Tyr Asp Lys Val Phe Glu Lys Leu Lys Glu
1               5                   10                  15

Phe Phe

<210> SEQ ID NO 266
<211> LENGTH: 18
<212> TYPE: PRT
<213> ORGANISM: Artificial sequence
<220> FEATURE:
<223> OTHER INFORMATION: synthetic

<400> SEQUENCE: 266

Asp Trp Leu Lys Ala Phe Tyr Asp Lys Val Ala Glu Lys Phe Lys Glu
1               5                   10                  15

Phe Phe

<210> SEQ ID NO 267
<211> LENGTH: 18
<212> TYPE: PRT
<213> ORGANISM: Artificial sequence
<220> FEATURE:
<223> OTHER INFORMATION: synthetic

<400> SEQUENCE: 267

Asp Trp Leu Lys Ala Phe Tyr Asp Lys Val Phe Glu Lys Phe Lys Glu
1               5                   10                  15

Phe Phe

<210> SEQ ID NO 268
<211> LENGTH: 18
<212> TYPE: PRT
<213> ORGANISM: Artificial sequence
<220> FEATURE:
```

<223> OTHER INFORMATION: synthetic

<400> SEQUENCE: 268

Glu Trp Leu Lys Leu Phe Tyr Glu Lys Val Leu Glu Lys Phe Lys Glu
1               5                   10                  15

Ala Phe

<210> SEQ ID NO 269
<211> LENGTH: 18
<212> TYPE: PRT
<213> ORGANISM: Artificial sequence
<220> FEATURE:
<223> OTHER INFORMATION: synthetic

<400> SEQUENCE: 269

Glu Trp Leu Lys Ala Phe Tyr Asp Lys Val Ala Glu Lys Phe Lys Glu
1               5                   10                  15

Ala Phe

<210> SEQ ID NO 270
<211> LENGTH: 18
<212> TYPE: PRT
<213> ORGANISM: Artificial sequence
<220> FEATURE:
<223> OTHER INFORMATION: synthetic

<400> SEQUENCE: 270

Glu Trp Leu Lys Ala Phe Tyr Asp Lys Val Ala Glu Lys Leu Lys Glu
1               5                   10                  15

Phe Phe

<210> SEQ ID NO 271
<211> LENGTH: 18
<212> TYPE: PRT
<213> ORGANISM: Artificial sequence
<220> FEATURE:
<223> OTHER INFORMATION: synthetic

<400> SEQUENCE: 271

Glu Trp Leu Lys Ala Phe Tyr Asp Lys Val Phe Glu Lys Phe Lys Glu
1               5                   10                  15

Ala Phe

<210> SEQ ID NO 272
<211> LENGTH: 18
<212> TYPE: PRT
<213> ORGANISM: Artificial sequence
<220> FEATURE:
<223> OTHER INFORMATION: synthetic

<400> SEQUENCE: 272

Glu Trp Leu Lys Ala Phe Tyr Asp Lys Val Phe Glu Lys Leu Lys Glu
1               5                   10                  15

Phe Phe

<210> SEQ ID NO 273
<211> LENGTH: 18
<212> TYPE: PRT
<213> ORGANISM: Artificial sequence
<220> FEATURE:
<223> OTHER INFORMATION: synthetic

<400> SEQUENCE: 273

Glu Trp Leu Lys Ala Phe Tyr Asp Lys Val Ala Glu Lys Phe Lys Glu
1               5                   10                  15

Phe Phe

<210> SEQ ID NO 274
<211> LENGTH: 18
<212> TYPE: PRT
<213> ORGANISM: Artificial sequence
<220> FEATURE:
<223> OTHER INFORMATION: synthetic

<400> SEQUENCE: 274

Glu Trp Leu Lys Ala Phe Tyr Asp Lys Val Phe Glu Lys Phe Lys Glu
1               5                   10                  15

Phe Phe

<210> SEQ ID NO 275
<211> LENGTH: 14
<212> TYPE: PRT
<213> ORGANISM: Artificial sequence
<220> FEATURE:
<223> OTHER INFORMATION: synthetic

<400> SEQUENCE: 275

Ala Phe Tyr Asp Lys Val Ala Glu Lys Leu Lys Glu Ala Phe
1               5                   10

<210> SEQ ID NO 276
<211> LENGTH: 14
<212> TYPE: PRT
<213> ORGANISM: Artificial sequence
<220> FEATURE:
<223> OTHER INFORMATION: synthetic

<400> SEQUENCE: 276

Ala Phe Tyr Asp Lys Val Ala Glu Lys Phe Lys Glu Ala Phe
1               5                   10

<210> SEQ ID NO 277
<211> LENGTH: 14
<212> TYPE: PRT
<213> ORGANISM: Artificial sequence
<220> FEATURE:
<223> OTHER INFORMATION: synthetic

<400> SEQUENCE: 277

Ala Phe Tyr Asp Lys Val Ala Glu Lys Phe Lys Glu Ala Phe
1               5                   10

<210> SEQ ID NO 278
<211> LENGTH: 14
<212> TYPE: PRT
<213> ORGANISM: Artificial sequence
<220> FEATURE:
<223> OTHER INFORMATION: synthetic

<400> SEQUENCE: 278

Ala Phe Tyr Asp Lys Phe Phe Glu Lys Phe Lys Glu Phe Phe
1               5                   10

<210> SEQ ID NO 279
<211> LENGTH: 14
<212> TYPE: PRT
<213> ORGANISM: Artificial sequence
<220> FEATURE:
<223> OTHER INFORMATION: synthetic

<400> SEQUENCE: 279

Ala Phe Tyr Asp Lys Phe Phe Glu Lys Phe Lys Glu Phe Phe
1               5                   10

<210> SEQ ID NO 280
<211> LENGTH: 14
<212> TYPE: PRT
<213> ORGANISM: Artificial sequence
<220> FEATURE:
<223> OTHER INFORMATION: synthetic

<400> SEQUENCE: 280

Ala Phe Tyr Asp Lys Val Ala Glu Lys Phe Lys Glu Ala Phe
1               5                   10

<210> SEQ ID NO 281
<211> LENGTH: 14
<212> TYPE: PRT
<213> ORGANISM: Artificial sequence
<220> FEATURE:
<223> OTHER INFORMATION: synthetic

<400> SEQUENCE: 281

Ala Phe Tyr Asp Lys Val Ala Glu Lys Leu Lys Glu Phe Phe
1               5                   10

<210> SEQ ID NO 282
<211> LENGTH: 14
<212> TYPE: PRT
<213> ORGANISM: Artificial sequence
<220> FEATURE:
<223> OTHER INFORMATION: synthetic

<400> SEQUENCE: 282

Ala Phe Tyr Asp Lys Val Phe Glu Lys Phe Lys Glu Ala Phe
1               5                   10

<210> SEQ ID NO 283
<211> LENGTH: 14
<212> TYPE: PRT
<213> ORGANISM: Artificial sequence
<220> FEATURE:
<223> OTHER INFORMATION: synthetic

<400> SEQUENCE: 283

Ala Phe Tyr Asp Lys Val Phe Glu Lys Leu Lys Glu Phe Phe
1               5                   10

<210> SEQ ID NO 284
<211> LENGTH: 14
<212> TYPE: PRT
<213> ORGANISM: Artificial sequence
<220> FEATURE:
<223> OTHER INFORMATION: synthetic

<400> SEQUENCE: 284

Ala Phe Tyr Asp Lys Val Ala Glu Lys Phe Lys Glu Phe Phe
1               5                   10

<210> SEQ ID NO 285
<211> LENGTH: 14
<212> TYPE: PRT
<213> ORGANISM: Artificial sequence
<220> FEATURE:
<223> OTHER INFORMATION: synthetic

<400> SEQUENCE: 285

Lys Ala Phe Tyr Asp Lys Val Phe Glu Lys Phe Lys Glu Phe
1               5                   10

<210> SEQ ID NO 286
<211> LENGTH: 14
<212> TYPE: PRT
<213> ORGANISM: Artificial sequence
<220> FEATURE:
<223> OTHER INFORMATION: synthetic

<400> SEQUENCE: 286

Leu Phe Tyr Glu Lys Val Leu Glu Lys Phe Lys Glu Ala Phe
1               5                   10

<210> SEQ ID NO 287
<211> LENGTH: 14
<212> TYPE: PRT
<213> ORGANISM: Artificial sequence
<220> FEATURE:
<223> OTHER INFORMATION: synthetic

<400> SEQUENCE: 287

Ala Phe Tyr Asp Lys Val Ala Glu Lys Phe Lys Glu Ala Phe
1               5                   10

<210> SEQ ID NO 288
<211> LENGTH: 14
<212> TYPE: PRT
<213> ORGANISM: Artificial sequence
<220> FEATURE:
<223> OTHER INFORMATION: synthetic

<400> SEQUENCE: 288

Ala Phe Tyr Asp Lys Val Ala Glu Lys Leu Lys Glu Phe Phe
1               5                   10

<210> SEQ ID NO 289
<211> LENGTH: 14
<212> TYPE: PRT
<213> ORGANISM: Artificial sequence
<220> FEATURE:
<223> OTHER INFORMATION: synthetic

<400> SEQUENCE: 289

Ala Phe Tyr Asp Lys Val Phe Glu Lys Phe Lys Glu Ala Phe
1               5                   10

<210> SEQ ID NO 290
<211> LENGTH: 14
<212> TYPE: PRT
<213> ORGANISM: Artificial sequence
<220> FEATURE:
<223> OTHER INFORMATION: synthetic

<400> SEQUENCE: 290

Ala Phe Tyr Asp Lys Val Phe Glu Lys Leu Lys Glu Phe Phe
1               5                   10

<210> SEQ ID NO 291
<211> LENGTH: 14
<212> TYPE: PRT
<213> ORGANISM: Artificial sequence
<220> FEATURE:
<223> OTHER INFORMATION: synthetic

<400> SEQUENCE: 291

```
Ala Phe Tyr Asp Lys Val Ala Glu Lys Phe Lys Glu Phe Phe
1               5                   10
```

<210> SEQ ID NO 292
<211> LENGTH: 14
<212> TYPE: PRT
<213> ORGANISM: Artificial sequence
<220> FEATURE:
<223> OTHER INFORMATION: synthetic

<400> SEQUENCE: 292

```
Ala Phe Tyr Asp Lys Val Phe Glu Lys Phe Lys Glu Phe Phe
1               5                   10
```

<210> SEQ ID NO 293
<211> LENGTH: 18
<212> TYPE: PRT
<213> ORGANISM: Artificial sequence
<220> FEATURE:
<223> OTHER INFORMATION: synthetic

<400> SEQUENCE: 293

```
Asp Trp Leu Lys Ala Leu Tyr Asp Lys Val Ala Glu Lys Leu Lys Glu
1               5                   10                  15

Ala Leu
```

<210> SEQ ID NO 294
<211> LENGTH: 18
<212> TYPE: PRT
<213> ORGANISM: Artificial sequence
<220> FEATURE:
<223> OTHER INFORMATION: synthetic

<400> SEQUENCE: 294

```
Asp Trp Phe Lys Ala Phe Tyr Glu Lys Val Ala Glu Lys Leu Lys Glu
1               5                   10                  15

Phe Phe
```

<210> SEQ ID NO 295
<211> LENGTH: 18
<212> TYPE: PRT
<213> ORGANISM: Artificial sequence
<220> FEATURE:
<223> OTHER INFORMATION: synthetic

<400> SEQUENCE: 295

```
Asp Trp Phe Lys Ala Phe Tyr Glu Lys Phe Phe Glu Lys Phe Lys Glu
1               5                   10                  15

Phe Phe
```

<210> SEQ ID NO 296
<211> LENGTH: 18
<212> TYPE: PRT
<213> ORGANISM: Artificial sequence
<220> FEATURE:
<223> OTHER INFORMATION: synthetic

<400> SEQUENCE: 296

```
Glu Trp Leu Lys Ala Leu Tyr Glu Lys Val Ala Glu Lys Leu Lys Glu
1               5                   10                  15

Ala Leu
```

<210> SEQ ID NO 297

<211> LENGTH: 18
<212> TYPE: PRT
<213> ORGANISM: Artificial sequence
<220> FEATURE:
<223> OTHER INFORMATION: synthetic

<400> SEQUENCE: 297

Glu Trp Leu Lys Ala Phe Tyr Glu Lys Val Ala Glu Lys Leu Lys Glu
1               5                   10                  15

Ala Phe

<210> SEQ ID NO 298
<211> LENGTH: 18
<212> TYPE: PRT
<213> ORGANISM: Artificial sequence
<220> FEATURE:
<223> OTHER INFORMATION: synthetic

<400> SEQUENCE: 298

Glu Trp Phe Lys Ala Phe Tyr Glu Lys Val Ala Glu Lys Leu Lys Glu
1               5                   10                  15

Phe Phe

<210> SEQ ID NO 299
<211> LENGTH: 18
<212> TYPE: PRT
<213> ORGANISM: Artificial sequence
<220> FEATURE:
<223> OTHER INFORMATION: synthetic

<400> SEQUENCE: 299

Glu Trp Leu Lys Ala Phe Tyr Glu Lys Val Phe Glu Lys Phe Lys Glu
1               5                   10                  15

Phe Phe

<210> SEQ ID NO 300
<211> LENGTH: 18
<212> TYPE: PRT
<213> ORGANISM: Artificial sequence
<220> FEATURE:
<223> OTHER INFORMATION: synthetic

<400> SEQUENCE: 300

Glu Trp Leu Lys Ala Phe Tyr Glu Lys Phe Phe Glu Lys Phe Lys Glu
1               5                   10                  15

Phe Phe

<210> SEQ ID NO 301
<211> LENGTH: 18
<212> TYPE: PRT
<213> ORGANISM: Artificial sequence
<220> FEATURE:
<223> OTHER INFORMATION: synthetic

<400> SEQUENCE: 301

Glu Trp Phe Lys Ala Phe Tyr Glu Lys Phe Phe Glu Lys Phe Lys Glu
1               5                   10                  15

Phe Phe

<210> SEQ ID NO 302
<211> LENGTH: 18
<212> TYPE: PRT
<213> ORGANISM: Artificial sequence
<220> FEATURE:

<223> OTHER INFORMATION: synthetic

<400> SEQUENCE: 302

Asp Phe Leu Lys Ala Trp Tyr Asp Lys Val Ala Glu Lys Leu Lys Glu
1               5                   10                  15

Ala Trp

<210> SEQ ID NO 303
<211> LENGTH: 18
<212> TYPE: PRT
<213> ORGANISM: Artificial sequence
<220> FEATURE:
<223> OTHER INFORMATION: synthetic

<400> SEQUENCE: 303

Glu Phe Leu Lys Ala Trp Tyr Glu Lys Val Ala Glu Lys Leu Lys Glu
1               5                   10                  15

Ala Trp

<210> SEQ ID NO 304
<211> LENGTH: 18
<212> TYPE: PRT
<213> ORGANISM: Artificial sequence
<220> FEATURE:
<223> OTHER INFORMATION: synthetic

<400> SEQUENCE: 304

Asp Phe Trp Lys Ala Trp Tyr Asp Lys Val Ala Glu Lys Leu Lys Glu
1               5                   10                  15

Trp Trp

<210> SEQ ID NO 305
<211> LENGTH: 18
<212> TYPE: PRT
<213> ORGANISM: Artificial sequence
<220> FEATURE:
<223> OTHER INFORMATION: synthetic

<400> SEQUENCE: 305

Glu Phe Trp Lys Ala Trp Tyr Glu Lys Val Ala Glu Lys Leu Lys Glu
1               5                   10                  15

Trp Trp

<210> SEQ ID NO 306
<211> LENGTH: 18
<212> TYPE: PRT
<213> ORGANISM: Artificial sequence
<220> FEATURE:
<223> OTHER INFORMATION: synthetic

<400> SEQUENCE: 306

Asp Lys Leu Lys Ala Phe Tyr Asp Lys Val Phe Glu Trp Ala Lys Glu
1               5                   10                  15

Ala Phe

<210> SEQ ID NO 307
<211> LENGTH: 18
<212> TYPE: PRT
<213> ORGANISM: Artificial sequence
<220> FEATURE:
<223> OTHER INFORMATION: synthetic

<400> SEQUENCE: 307

```
Asp Lys Trp Lys Ala Val Tyr Asp Lys Phe Ala Glu Ala Phe Lys Glu
1               5                   10                  15

Phe Leu

<210> SEQ ID NO 308
<211> LENGTH: 18
<212> TYPE: PRT
<213> ORGANISM: Artificial sequence
<220> FEATURE:
<223> OTHER INFORMATION: synthetic

<400> SEQUENCE: 308

Glu Lys Leu Lys Ala Phe Tyr Glu Lys Val Phe Glu Trp Ala Lys Glu
1               5                   10                  15

Ala Phe

<210> SEQ ID NO 309
<211> LENGTH: 18
<212> TYPE: PRT
<213> ORGANISM: Artificial sequence
<220> FEATURE:
<223> OTHER INFORMATION: synthetic

<400> SEQUENCE: 309

Glu Lys Trp Lys Ala Val Tyr Glu Lys Phe Ala Glu Ala Phe Lys Glu
1               5                   10                  15

Phe Leu

<210> SEQ ID NO 310
<211> LENGTH: 18
<212> TYPE: PRT
<213> ORGANISM: Artificial sequence
<220> FEATURE:
<223> OTHER INFORMATION: synthetic

<400> SEQUENCE: 310

Asp Trp Leu Lys Ala Phe Val Asp Lys Phe Ala Glu Lys Phe Lys Glu
1               5                   10                  15

Ala Tyr

<210> SEQ ID NO 311
<211> LENGTH: 18
<212> TYPE: PRT
<213> ORGANISM: Artificial sequence
<220> FEATURE:
<223> OTHER INFORMATION: synthetic

<400> SEQUENCE: 311

Glu Lys Trp Lys Ala Val Tyr Glu Lys Phe Ala Glu Ala Phe Lys Glu
1               5                   10                  15

Phe Leu

<210> SEQ ID NO 312
<211> LENGTH: 18
<212> TYPE: PRT
<213> ORGANISM: Artificial sequence
<220> FEATURE:
<223> OTHER INFORMATION: synthetic

<400> SEQUENCE: 312

Asp Trp Leu Lys Ala Phe Val Tyr Asp Lys Val Phe Lys Leu Lys Glu
1               5                   10                  15

Phe Phe
```

```
<210> SEQ ID NO 313
<211> LENGTH: 18
<212> TYPE: PRT
<213> ORGANISM: Artificial sequence
<220> FEATURE:
<223> OTHER INFORMATION: synthetic

<400> SEQUENCE: 313

Glu Trp Leu Lys Ala Phe Val Tyr Glu Lys Val Phe Lys Leu Lys Glu
1               5                   10                  15

Phe Phe

<210> SEQ ID NO 314
<211> LENGTH: 18
<212> TYPE: PRT
<213> ORGANISM: Artificial sequence
<220> FEATURE:
<223> OTHER INFORMATION: synthetic

<400> SEQUENCE: 314

Asp Trp Leu Arg Ala Phe Tyr Asp Lys Val Ala Glu Lys Leu Lys Glu
1               5                   10                  15

Ala Phe

<210> SEQ ID NO 315
<211> LENGTH: 18
<212> TYPE: PRT
<213> ORGANISM: Artificial sequence
<220> FEATURE:
<223> OTHER INFORMATION: synthetic

<400> SEQUENCE: 315

Glu Trp Leu Arg Ala Phe Tyr Glu Lys Val Ala Glu Lys Leu Lys Glu
1               5                   10                  15

Ala Phe

<210> SEQ ID NO 316
<211> LENGTH: 18
<212> TYPE: PRT
<213> ORGANISM: Artificial sequence
<220> FEATURE:
<223> OTHER INFORMATION: synthetic

<400> SEQUENCE: 316

Asp Trp Leu Lys Ala Phe Tyr Asp Arg Val Ala Glu Lys Leu Lys Glu
1               5                   10                  15

Ala Phe

<210> SEQ ID NO 317
<211> LENGTH: 18
<212> TYPE: PRT
<213> ORGANISM: Artificial sequence
<220> FEATURE:
<223> OTHER INFORMATION: synthetic

<400> SEQUENCE: 317

Glu Trp Leu Lys Ala Phe Tyr Glu Arg Val Ala Glu Lys Leu Lys Glu
1               5                   10                  15

Ala Phe

<210> SEQ ID NO 318
<211> LENGTH: 18
```

```
<212> TYPE: PRT
<213> ORGANISM: Artificial sequence
<220> FEATURE:
<223> OTHER INFORMATION: synthetic

<400> SEQUENCE: 318

Asp Trp Leu Lys Ala Phe Tyr Asp Lys Val Ala Glu Arg Leu Lys Glu
1               5                   10                  15

Ala Phe

<210> SEQ ID NO 319
<211> LENGTH: 18
<212> TYPE: PRT
<213> ORGANISM: Artificial sequence
<220> FEATURE:
<223> OTHER INFORMATION: synthetic

<400> SEQUENCE: 319

Glu Trp Leu Lys Ala Phe Tyr Glu Lys Val Ala Glu Arg Leu Lys Glu
1               5                   10                  15

Ala Phe

<210> SEQ ID NO 320
<211> LENGTH: 18
<212> TYPE: PRT
<213> ORGANISM: Artificial sequence
<220> FEATURE:
<223> OTHER INFORMATION: synthetic

<400> SEQUENCE: 320

Asp Trp Leu Lys Ala Phe Tyr Asp Lys Val Ala Glu Lys Leu Arg Glu
1               5                   10                  15

Ala Phe

<210> SEQ ID NO 321
<211> LENGTH: 18
<212> TYPE: PRT
<213> ORGANISM: Artificial sequence
<220> FEATURE:
<223> OTHER INFORMATION: synthetic

<400> SEQUENCE: 321

Glu Trp Leu Lys Ala Phe Tyr Glu Lys Val Ala Glu Lys Leu Arg Glu
1               5                   10                  15

Ala Phe

<210> SEQ ID NO 322
<211> LENGTH: 18
<212> TYPE: PRT
<213> ORGANISM: Artificial sequence
<220> FEATURE:
<223> OTHER INFORMATION: synthetic

<400> SEQUENCE: 322

Asp Trp Leu Lys Ala Phe Tyr Asp Arg Val Ala Glu Arg Leu Lys Glu
1               5                   10                  15

Ala Phe

<210> SEQ ID NO 323
<211> LENGTH: 18
<212> TYPE: PRT
<213> ORGANISM: Artificial sequence
<220> FEATURE:
<223> OTHER INFORMATION: synthetic
```

```
<400> SEQUENCE: 323

Glu Trp Leu Lys Ala Phe Tyr Glu Arg Val Ala Glu Arg Leu Lys Glu
1               5                   10                  15

Ala Phe

<210> SEQ ID NO 324
<211> LENGTH: 18
<212> TYPE: PRT
<213> ORGANISM: Artificial sequence
<220> FEATURE:
<223> OTHER INFORMATION: synthetic

<400> SEQUENCE: 324

Asp Trp Leu Arg Ala Phe Tyr Asp Lys Val Ala Glu Lys Leu Arg Glu
1               5                   10                  15

Ala Phe

<210> SEQ ID NO 325
<211> LENGTH: 18
<212> TYPE: PRT
<213> ORGANISM: Artificial sequence
<220> FEATURE:
<223> OTHER INFORMATION: synthetic

<400> SEQUENCE: 325

Glu Trp Leu Arg Ala Phe Tyr Glu Lys Val Ala Glu Lys Leu Arg Glu
1               5                   10                  15

Ala Phe

<210> SEQ ID NO 326
<211> LENGTH: 18
<212> TYPE: PRT
<213> ORGANISM: Artificial sequence
<220> FEATURE:
<223> OTHER INFORMATION: synthetic

<400> SEQUENCE: 326

Asp Trp Leu Arg Ala Phe Tyr Asp Arg Val Ala Glu Lys Leu Lys Glu
1               5                   10                  15

Ala Phe

<210> SEQ ID NO 327
<211> LENGTH: 18
<212> TYPE: PRT
<213> ORGANISM: Artificial sequence
<220> FEATURE:
<223> OTHER INFORMATION: synthetic

<400> SEQUENCE: 327

Glu Trp Leu Arg Ala Phe Tyr Glu Arg Val Ala Glu Lys Leu Lys Glu
1               5                   10                  15

Ala Phe

<210> SEQ ID NO 328
<211> LENGTH: 18
<212> TYPE: PRT
<213> ORGANISM: Artificial sequence
<220> FEATURE:
<223> OTHER INFORMATION: synthetic

<400> SEQUENCE: 328

Asp Trp Leu Lys Ala Phe Tyr Asp Lys Val Ala Glu Arg Leu Arg Glu
```

-continued

```
1               5                   10                  15

Ala Phe

<210> SEQ ID NO 329
<211> LENGTH: 18
<212> TYPE: PRT
<213> ORGANISM: Artificial sequence
<220> FEATURE:
<223> OTHER INFORMATION: synthetic

<400> SEQUENCE: 329

Glu Trp Leu Lys Ala Phe Tyr Glu Lys Val Ala Glu Arg Leu Arg Glu
1               5                   10                  15

Ala Phe

<210> SEQ ID NO 330
<211> LENGTH: 18
<212> TYPE: PRT
<213> ORGANISM: Artificial sequence
<220> FEATURE:
<223> OTHER INFORMATION: synthetic

<400> SEQUENCE: 330

Asp Trp Leu Arg Ala Phe Tyr Asp Lys Val Ala Glu Arg Leu Lys Glu
1               5                   10                  15

Ala Phe

<210> SEQ ID NO 331
<211> LENGTH: 18
<212> TYPE: PRT
<213> ORGANISM: Artificial sequence
<220> FEATURE:
<223> OTHER INFORMATION: synthetic

<400> SEQUENCE: 331

Glu Trp Leu Arg Ala Phe Tyr Glu Lys Val Ala Glu Arg Leu Lys Glu
1               5                   10                  15

Ala Phe

<210> SEQ ID NO 332
<211> LENGTH: 18
<212> TYPE: PRT
<213> ORGANISM: Artificial sequence
<220> FEATURE:
<223> OTHER INFORMATION: synthetic

<400> SEQUENCE: 332

Phe Ala Glu Lys Phe Lys Glu Ala Val Lys Asp Tyr Phe Ala Lys Phe
1               5                   10                  15

Trp Asp

<210> SEQ ID NO 333
<211> LENGTH: 18
<212> TYPE: PRT
<213> ORGANISM: Artificial sequence
<220> FEATURE:
<223> OTHER INFORMATION: synthetic

<400> SEQUENCE: 333

Asp Trp Phe Lys Ala Phe Tyr Asp Lys Val Ala Glu Lys Phe Lys Glu
1               5                   10                  15

Ala Phe
```

```
<210> SEQ ID NO 334
<211> LENGTH: 18
<212> TYPE: PRT
<213> ORGANISM: Artificial sequence
<220> FEATURE:
<223> OTHER INFORMATION: synthetic

<400> SEQUENCE: 334

Asp Trp Leu Lys Ala Phe Tyr Asp Lys Val Ala Glu Lys Leu Lys Glu
1               5                   10                  15

Ala Phe

<210> SEQ ID NO 335
<211> LENGTH: 34
<212> TYPE: PRT
<213> ORGANISM: Artificial sequence
<220> FEATURE:
<223> OTHER INFORMATION: synthetic

<400> SEQUENCE: 335

Pro Ala Leu Glu Asp Leu Arg Gln Gly Leu Leu Pro Val Leu Glu Ser
1               5                   10                  15

Phe Lys Val Phe Leu Ser Ala Leu Glu Glu Tyr Thr Lys Lys Leu Asn
            20                  25                  30

Thr Gln
```